(12) United States Patent
Robertson

(10) Patent No.: US 8,057,498 B2
(45) Date of Patent: Nov. 15, 2011

(54) ULTRASONIC SURGICAL INSTRUMENT BLADES

(75) Inventor: Galen C. Robertson, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 254 days.

(21) Appl. No.: 11/998,543

(22) Filed: Nov. 30, 2007

(65) Prior Publication Data

US 2009/0143795 A1   Jun. 4, 2009

(51) Int. Cl.
*A61B 17/32* (2006.01)
(52) U.S. Cl. .......... 606/169; 30/344.55; 30/344.57; 30/353; 83/956
(58) Field of Classification Search .......... 606/37, 606/39, 45, 169, 170, 171; 30/346.55, 346.57, 30/353, 357; 83/956
See application file for complete search history.

(56) References Cited

U.S. PATENT DOCUMENTS

| | | | |
|---|---|---|---|
| 2,736,960 A | 3/1956 | Armstrong | |
| 2,849,788 A | 9/1958 | Creek | |
| 3,015,961 A | 1/1962 | Roney | |
| 3,526,219 A | 9/1970 | Balamuth | |
| 3,636,943 A | 1/1972 | Balamuth | |
| 3,776,238 A | 12/1973 | Peyman et al. | |
| 3,805,787 A | 4/1974 | Banko | |
| 3,862,630 A | 1/1975 | Balamuth | |
| 3,918,442 A | 11/1975 | Nikolaev et al. | |
| 3,956,826 A | 5/1976 | Perdreaux, Jr. | |
| 4,156,187 A | 5/1979 | Murry et al. | |
| 4,200,106 A | 4/1980 | Douvas et al. | |
| 4,445,063 A | 4/1984 | Smith | |
| 4,491,132 A | 1/1985 | Aikins | |
| 4,634,420 A | 1/1987 | Spinosa et al. | |
| 4,640,279 A | 2/1987 | Beard | |
| 4,708,127 A | 11/1987 | Abdelghani | |
| 4,832,683 A | 5/1989 | Idemoto et al. | |
| 4,838,853 A | 6/1989 | Parisi | |
| 4,850,354 A | 7/1989 | McGurk-Burleson et al. | |
| 4,865,159 A | 9/1989 | Jamison | |
| 4,896,009 A | 1/1990 | Pawlowski | |
| 4,981,756 A | 1/1991 | Rhandhawa | |

(Continued)

FOREIGN PATENT DOCUMENTS

EP         0443256 A1     8/1991

(Continued)

OTHER PUBLICATIONS

Technology Overview, printed from www.harmonicscalpel.com, Internet site, website accessed on Jun. 13, 2007, (3 pages).

(Continued)

*Primary Examiner* — S. Thomas Hughes
*Assistant Examiner* — Jonathan W Miles

(57) ABSTRACT

An ultrasonic surgical instrument including an ultrasonically actuated blade or end effector having a treatment portion. The blade can define a central axis and at least one axis which is transverse to the central axis, wherein the transverse axis can lie within a plane which is perpendicular, or normal, to the longitudinal axis and can define a cross-section of the treatment portion. Such a cross-section can include a central portion and a step extending from the central portion, wherein the central portion can comprise a width, and wherein the step can comprise a cutting edge. In at least one embodiment, the cutting edge can be defined by first and second surfaces which define an angle therebetween. In various embodiments, the position of the cutting edge and/or the angle between the cutting edge surfaces can be selected in order to balance the blade with respect to the transverse axis.

15 Claims, 37 Drawing Sheets

U.S. PATENT DOCUMENTS

| | | |
|---|---|---|
| 5,026,387 A | 6/1991 | Thomas |
| 5,112,300 A | 5/1992 | Ureche |
| 5,123,903 A | 6/1992 | Quaid et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,213,569 A | 5/1993 | Davis |
| 5,221,282 A | 6/1993 | Wuchinich |
| 5,226,910 A | 7/1993 | Kajiyama et al. |
| 5,241,236 A | 8/1993 | Sasaki et al. |
| 5,257,988 A | 11/1993 | L'Esperance, Jr. |
| 5,261,922 A | 11/1993 | Hood |
| 5,263,957 A | 11/1993 | Davison |
| 5,282,800 A | 2/1994 | Foshee et al. |
| D347,474 S | 5/1994 | Olson |
| 5,322,055 A | 6/1994 | Davison et al. |
| 5,324,299 A | 6/1994 | Davison et al. |
| 5,346,502 A | 9/1994 | Estabrook et al. |
| 5,366,466 A | 11/1994 | Christian et al. |
| D354,564 S | 1/1995 | Medema |
| 5,411,481 A | 5/1995 | Allen et al. |
| 5,419,761 A | 5/1995 | Narayanan et al. |
| 5,421,829 A | 6/1995 | Olichney et al. |
| 5,449,370 A | 9/1995 | Vaitekunas |
| 5,486,162 A | 1/1996 | Brumbach |
| 5,500,216 A | 3/1996 | Julian et al. |
| 5,501,654 A | 3/1996 | Failla et al. |
| 5,505,693 A | 4/1996 | Mackool |
| 5,562,609 A | 10/1996 | Brumbach |
| 5,562,610 A | 10/1996 | Brumbach |
| 5,601,601 A | 2/1997 | Tal et al. |
| 5,607,436 A | 3/1997 | Pratt et al. |
| 5,618,492 A | 4/1997 | Auten et al. |
| 5,628,760 A | 5/1997 | Knoepfler |
| 5,630,420 A | 5/1997 | Vaitekunas |
| D381,077 S | 7/1997 | Hunt |
| 5,653,713 A | 8/1997 | Michelson |
| 5,669,922 A | 9/1997 | Hood |
| 5,674,235 A | 10/1997 | Parisi |
| 5,690,269 A | 11/1997 | Bolanos et al. |
| 5,694,936 A | 12/1997 | Fujimoto et al. |
| 5,713,896 A | 2/1998 | Nardella |
| 5,741,226 A | 4/1998 | Strukel et al. |
| 5,810,859 A | 9/1998 | DiMatteo et al. |
| 5,827,323 A | 10/1998 | Klieman et al. |
| 5,828,160 A | 10/1998 | Sugishita |
| 5,843,109 A | 12/1998 | Mehta et al. |
| 5,879,364 A | 3/1999 | Bromfield et al. |
| 5,893,835 A | 4/1999 | Witt et al. |
| 5,897,569 A | 4/1999 | Kellogg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,989,274 A | 11/1999 | Davison et al. |
| 5,989,275 A | 11/1999 | Estabrook et al. |
| 6,033,375 A | 3/2000 | Brumbach |
| 6,063,098 A | 5/2000 | Houser et al. |
| 6,066,132 A | 5/2000 | Chen et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,109,500 A | 8/2000 | Alli et al. |
| 6,113,594 A | 9/2000 | Savage |
| 6,139,320 A | 10/2000 | Hahn |
| 6,152,902 A | 11/2000 | Christian et al. |
| 6,159,160 A | 12/2000 | Hsei et al. |
| 6,159,175 A | 12/2000 | Strukel et al. |
| 6,206,844 B1 | 3/2001 | Reichel et al. |
| 6,210,403 B1 | 4/2001 | Klicek |
| 6,214,023 B1 | 4/2001 | Whipple et al. |
| 6,238,366 B1 | 5/2001 | Savage et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |
| 6,325,811 B1 | 12/2001 | Messerly |
| 6,328,751 B1 | 12/2001 | Beaupre |
| 6,352,532 B1 | 3/2002 | Kramer et al. |
| 6,383,194 B1 | 5/2002 | Pothula |
| 6,387,109 B1 | 5/2002 | Davison et al. |
| 6,391,042 B1 | 5/2002 | Cimino |
| 6,416,486 B1 | 7/2002 | Wampler |
| 6,423,073 B2 | 7/2002 | Bowman |
| 6,423,082 B1 | 7/2002 | Houser et al. |
| 6,432,118 B1 | 8/2002 | Messerly |
| 6,436,114 B1 | 8/2002 | Novak et al. |
| 6,436,115 B1 | 8/2002 | Beaupre |
| 6,443,969 B1 | 9/2002 | Novak et al. |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,188 B2 | 12/2002 | Harper et al. |
| 6,524,316 B1 | 2/2003 | Nicholson et al. |
| 6,537,291 B2 | 3/2003 | Friedman et al. |
| 6,543,456 B2 | 4/2003 | Freeman |
| 6,544,260 B1 | 4/2003 | Markel et al. |
| 6,561,983 B2 | 5/2003 | Cronin et al. |
| 6,582,451 B1 | 6/2003 | Marucci et al. |
| 6,589,200 B1 | 7/2003 | Schwemberger et al. |
| 6,589,239 B2 | 7/2003 | Khandkar et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,662,127 B2 | 12/2003 | Wiener et al. |
| 6,663,941 B2 | 12/2003 | Brown et al. |
| 6,676,660 B2 | 1/2004 | Wampler et al. |
| 6,678,621 B2 | 1/2004 | Wiener et al. |
| 6,679,899 B2 | 1/2004 | Wiener et al. |
| 6,682,544 B2 | 1/2004 | Mastri et al. |
| 6,716,215 B1 | 4/2004 | David et al. |
| 6,733,506 B1 | 5/2004 | McDevitt et al. |
| 6,773,444 B2 | 8/2004 | Messerly |
| 6,786,383 B2 | 9/2004 | Stegelmann |
| 6,790,216 B1 | 9/2004 | Ishikawa |
| 6,869,439 B2 | 3/2005 | White et al. |
| 6,875,220 B2 | 4/2005 | Du et al. |
| 6,908,472 B2 | 6/2005 | Wiener et al. |
| 6,929,632 B2 | 8/2005 | Nita et al. |
| D509,589 S | 9/2005 | Wells |
| 6,945,981 B2 | 9/2005 | Donofrio et al. |
| D511,145 S | 11/2005 | Donofrio et al. |
| 6,976,969 B2 | 12/2005 | Messerly |
| 6,977,495 B2 | 12/2005 | Donofrio |
| 6,984,220 B2 | 1/2006 | Wuchinich |
| 7,041,088 B2 | 5/2006 | Nawrocki et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,108,695 B2 | 9/2006 | Witt et al. |
| 7,118,564 B2 | 10/2006 | Ritchie et al. |
| 7,135,018 B2 | 11/2006 | Ryan et al. |
| 7,135,030 B2 | 11/2006 | Schwemberger et al. |
| 7,153,315 B2 | 12/2006 | Miller |
| 7,156,189 B1 | 1/2007 | Bar-Cohen et al. |
| 7,156,853 B2 | 1/2007 | Muratsu |

| Patent No. | Date | Inventor |
|---|---|---|
| 7,157,058 B2 | 1/2007 | Marhasin et al. |
| 7,159,750 B2 | 1/2007 | Racenet et al. |
| 7,163,548 B2 | 1/2007 | Stulen et al. |
| 7,179,271 B2 | 2/2007 | Friedman et al. |
| 7,204,820 B2 | 4/2007 | Akahoshi |
| 7,223,229 B2 | 5/2007 | Inman et al. |
| 7,229,455 B2 | 6/2007 | Sakurai et al. |
| 7,273,483 B2 | 9/2007 | Wiener et al. |
| 7,331,410 B2 | 2/2008 | Yong et al. |
| 7,380,695 B2 | 6/2008 | Doll et al. |
| 7,390,317 B2 | 6/2008 | Taylor et al. |
| D576,725 S | 9/2008 | Shumer et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,472,815 B2 | 1/2009 | Shelton, IV et al. |
| 7,479,148 B2 | 1/2009 | Beaupre |
| 7,479,160 B2 | 1/2009 | Branch et al. |
| 7,503,893 B2 | 3/2009 | Kucklick |
| 7,534,243 B1 | 5/2009 | Chin et al. |
| D594,983 S | 6/2009 | Price et al. |
| D618,797 S | 6/2010 | Price et al. |
| 7,770,774 B2 | 8/2010 | Mastri et al. |
| 7,780,659 B2 | 8/2010 | Okada et al. |
| D631,965 S | 2/2011 | Price et al. |
| 2001/0025184 A1 | 9/2001 | Messerly |
| 2001/0039419 A1 | 11/2001 | Francischelli et al. |
| 2002/0019649 A1 | 2/2002 | Sikora et al. |
| 2002/0022836 A1 | 2/2002 | Goble et al. |
| 2002/0077550 A1 | 6/2002 | Rabiner et al. |
| 2002/0156493 A1 | 10/2002 | Houser et al. |
| 2003/0055443 A1 | 3/2003 | Spotnitz |
| 2003/0204199 A1 | 10/2003 | Novak et al. |
| 2003/0212332 A1 | 11/2003 | Fenton et al. |
| 2004/0030254 A1 | 2/2004 | Babaev |
| 2004/0047485 A1 | 3/2004 | Sherrit et al. |
| 2004/0092921 A1 | 5/2004 | Kadziauskas et al. |
| 2004/0097919 A1 | 5/2004 | Wellman et al. |
| 2004/0097996 A1 | 5/2004 | Rabiner et al. |
| 2004/0199193 A1 | 10/2004 | Hayashi et al. |
| 2004/0204728 A1 | 10/2004 | Haefner |
| 2004/0260300 A1 | 12/2004 | Gorensek et al. |
| 2005/0049546 A1 | 3/2005 | Messerly et al. |
| 2005/0143769 A1 | 6/2005 | White et al. |
| 2005/0165345 A1 | 7/2005 | Laufer et al. |
| 2005/0177184 A1 | 8/2005 | Easley |
| 2005/0192610 A1 | 9/2005 | Houser et al. |
| 2005/0209620 A1 | 9/2005 | Du et al. |
| 2005/0261581 A1 | 11/2005 | Hughes et al. |
| 2005/0261588 A1 | 11/2005 | Makin et al. |
| 2005/0288659 A1 | 12/2005 | Kimura et al. |
| 2006/0030797 A1 | 2/2006 | Zhou et al. |
| 2006/0063130 A1 | 3/2006 | Hayman et al. |
| 2006/0079878 A1 | 4/2006 | Houser |
| 2006/0084963 A1 | 4/2006 | Messerly |
| 2006/0190034 A1 | 8/2006 | Nishizawa et al. |
| 2006/0211943 A1 | 9/2006 | Beaupre |
| 2006/0235306 A1 | 10/2006 | Cotter et al. |
| 2006/0253050 A1 | 11/2006 | Yoshimine et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0060915 A1 | 3/2007 | Kucklick |
| 2007/0063618 A1 | 3/2007 | Bromfield |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0173872 A1 | 7/2007 | Neuenfeldt |
| 2007/0185380 A1 | 8/2007 | Kucklick |
| 2007/0219481 A1 | 9/2007 | Babaev |
| 2007/0249941 A1 | 10/2007 | Salehi et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0082039 A1 | 4/2008 | Babaev |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208231 A1 | 8/2008 | Ota et al. |
| 2008/0234708 A1 | 9/2008 | Houser et al. |
| 2008/0234709 A1 | 9/2008 | Houser |
| 2008/0234710 A1 | 9/2008 | Neurohr et al. |
| 2008/0234711 A1 | 9/2008 | Houser et al. |
| 2008/0262490 A1 | 10/2008 | Williams |
| 2008/0287948 A1 | 11/2008 | Newton et al. |
| 2009/0030311 A1 | 1/2009 | Stulen et al. |
| 2009/0030351 A1 | 1/2009 | Wiener et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036911 A1 | 2/2009 | Stulen |
| 2009/0036912 A1 | 2/2009 | Wiener et al. |
| 2009/0036913 A1 | 2/2009 | Wiener et al. |
| 2009/0036914 A1 | 2/2009 | Houser |
| 2009/0082716 A1 | 3/2009 | Akahoshi |
| 2009/0105750 A1 | 4/2009 | Price et al. |
| 2009/0143796 A1 | 6/2009 | Stulen et al. |
| 2009/0143806 A1 | 6/2009 | Witt et al. |
| 2010/0036405 A1 | 2/2010 | Giordano et al. |
| 2010/0179577 A1 | 7/2010 | Houser |
| 2010/0187283 A1 | 7/2010 | Crainich et al. |
| 2010/0298743 A1 | 11/2010 | Nield et al. |
| 2010/0298851 A1 | 11/2010 | Nield |
| 2010/0331869 A1 | 12/2010 | Voegele et al. |
| 2010/0331870 A1 | 12/2010 | Wan et al. |
| 2010/0331871 A1 | 12/2010 | Nield et al. |
| 2010/0331872 A1 | 12/2010 | Houser et al. |
| 2011/0015627 A1 | 1/2011 | DiNardo et al. |
| 2011/0015631 A1 | 1/2011 | Wiener et al. |
| 2011/0015660 A1 | 1/2011 | Wiener et al. |

FOREIGN PATENT DOCUMENTS

| | | |
|---|---|---|
| EP | 0456470 A1 | 11/1991 |
| EP | 0482195 B1 | 4/1992 |
| EP | 0612570 B1 | 6/1997 |
| EP | 0908148 B1 | 1/2002 |
| EP | 1199044 B1 | 12/2005 |
| EP | 1844720 A1 | 10/2007 |
| EP | 1862133 A1 | 12/2007 |
| EP | 1974771 A1 | 10/2008 |
| EP | 1832259 B1 | 6/2009 |
| EP | 2074959 A1 | 7/2009 |
| WO | WO 92/22259 A2 | 12/1992 |
| WO | WO 98/37815 A1 | 9/1998 |
| WO | WO 01/54590 A1 | 8/2001 |
| WO | WO 2005/122917 | 12/2005 |
| WO | WO 2006/042210 A2 | 4/2006 |
| WO | WO 2006/129465 A1 | 12/2006 |
| WO | WO 2007/047531 A2 | 4/2007 |
| WO | WO 2007/143665 A2 | 12/2007 |
| WO | WO 2009/027065 | 3/2009 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

AST Products, Inc., "Principles of Video Contact Angle Analysis," 20 pages, (date unknown).

Lim et al., "A Review of Mechanism Used in Laparoscopic Surgical Instruments," Mechanism and Machine Theory, vol. 38, pp. 1133-1147, (2003).

International Search Report for PCT/US08/57443, Sep. 4, 2008 (4 pages).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

U.S. Appl. No. 12/181,816, filed Jul. 29, 2008.
U.S. Appl. No. 11/881,602, filed Jul. 27, 2007.
U.S. Appl. No. 11/888,081, filed Jul. 31, 2007.
U.S. Appl. No. 11/881,636, filed Jul. 27, 2007.
U.S. Appl. No. 11/881,645, filed Jul. 27, 2007.
U.S. Appl. No. 11/881,654, filed Jul. 27, 2007.
U.S. Appl. No. 11/888,171, filed Jul. 31, 2007.
U.S. Appl. No. 11/998,758, filed Nov. 30, 2007.
U.S. Appl. No. 11/881,662, filed Jul. 27, 2007.
U.S. Appl. No. 11/888,222, filed Jul. 31, 2007.
U.S. Appl. No. 12/245,158, filed Oct. 3, 2008.
U.S. Appl. No. 29/292,295, filed Oct. 5, 2007.
U.S. Appl. No. 11/726,625, filed Mar. 22, 2007.
AST Products, Inc., "Principles of Video Contact Angle Analysis," 20 pages, (2006).
U.S. Appl. No. 29/327,737, filed Nov. 12, 2008.
U.S. Appl. No. 12/469,293, filed May 20, 2009.
U.S. Appl. No. 12/469,308, filed May 20, 2009.
U.S. Appl. No. 12/503,769, filed Jul. 15, 2009.
U.S. Appl. No. 12/503,770, filed Jul. 15, 2009.
U.S. Appl. No. 12/503,766, filed Jul. 15, 2009.
U.S. Appl. No. 12/490,906, filed Jun. 24, 2009.
U.S. Appl. No. 12/490,922, filed Jun. 24, 2009.
U.S. Appl. No. 12/490,933, filed Jun. 24, 2009.
U.S. Appl. No. 12/490,948, filed Jun. 24, 2009.
U.S. Appl. No. 12/703,860, filed Feb. 11, 2010.
U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,877, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,893, filed Feb. 11, 2010.
U.S. Appl. No. 12/703,899, filed Feb. 11, 2010.
U.S. Appl. No. 12/732,702, filed Mar. 26, 2010.
U.S. Appl. No. 29/361,917, filed May 17, 2010.
U.S. Appl. No. 12/896,351, filed Oct. 1, 2010.
U.S. Appl. No. 12/896,479, filed Oct. 1, 2010.
U.S. Appl. No. 12/896,360, filed Oct. 1, 2010.
U.S. Appl. No. 12/896,345, filed Oct. 1, 2010.
U.S. Appl. No. 12/896,384, filed Oct. 1, 2010.
U.S. Appl. No. 12/896,467, filed Oct. 1, 2010.
U.S. Appl. No. 12/896,451, filed Oct. 1, 2010.
U.S. Appl. No. 12/896,470, filed Oct. 1, 2010.
U.S. Appl. No. 12/896,411, filed Oct. 1, 2010.
U.S. Appl. No. 12/896,420, filed Oct. 1, 2010.

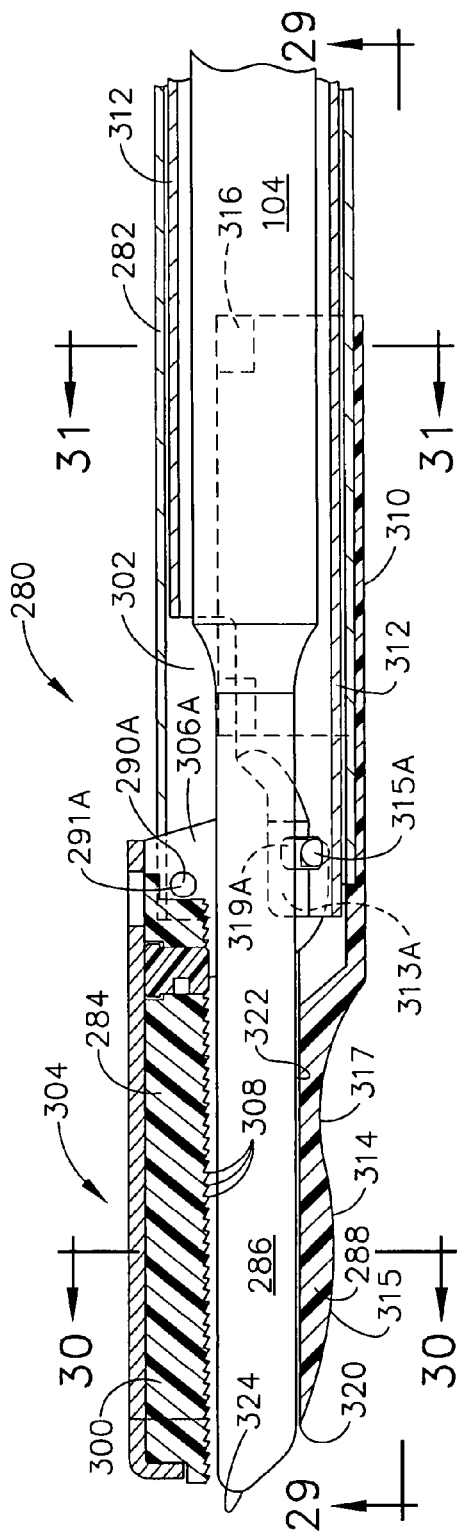
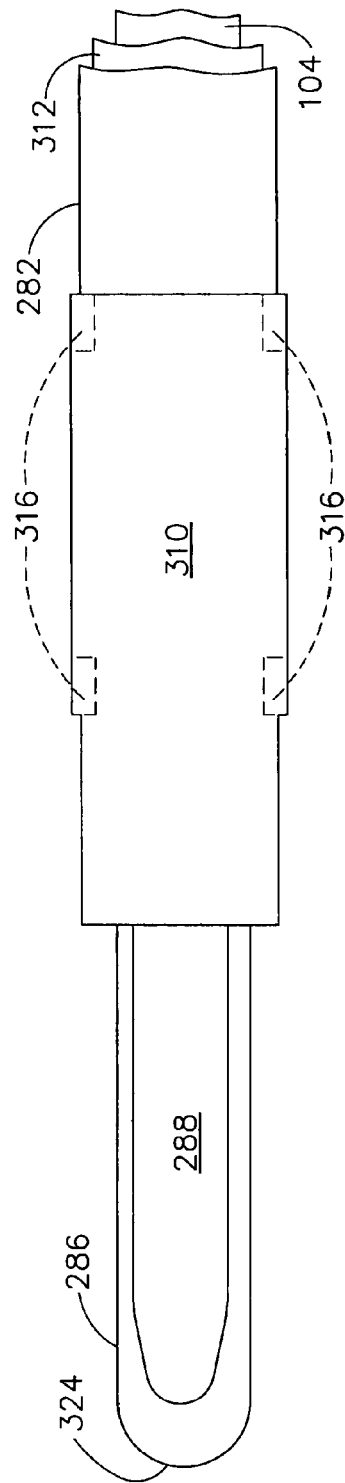
FIG. 28
FIG. 29

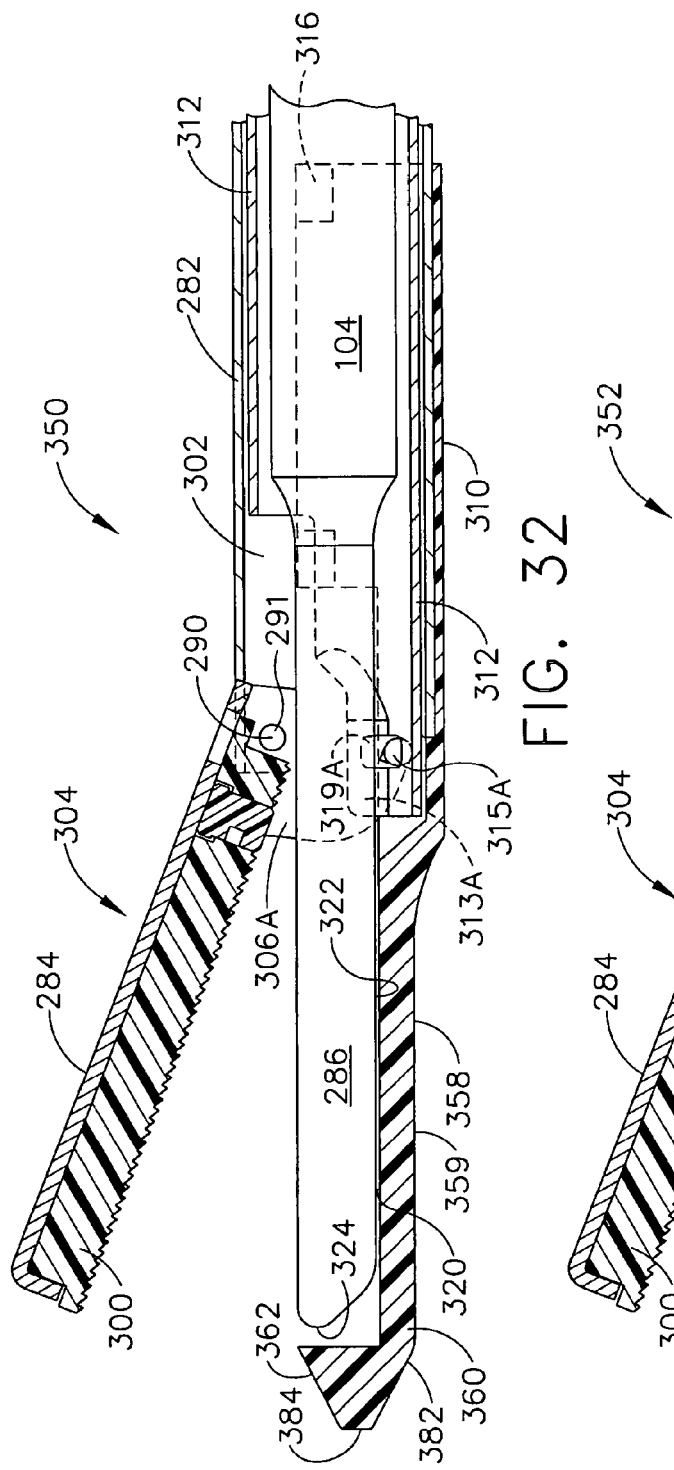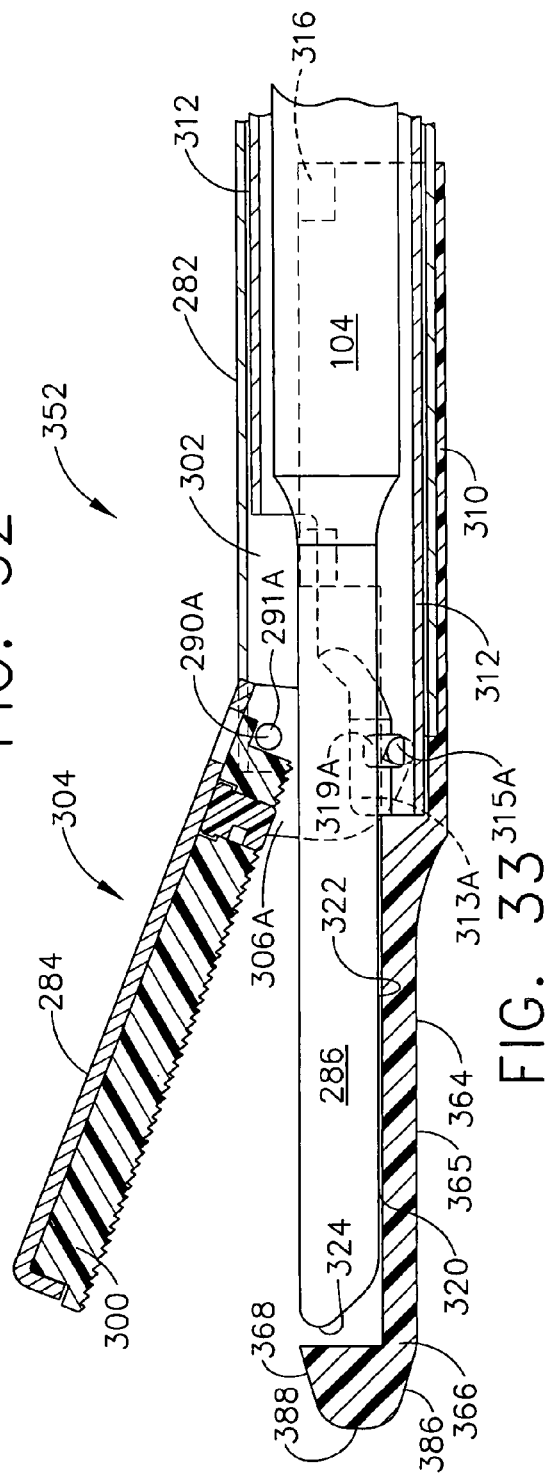

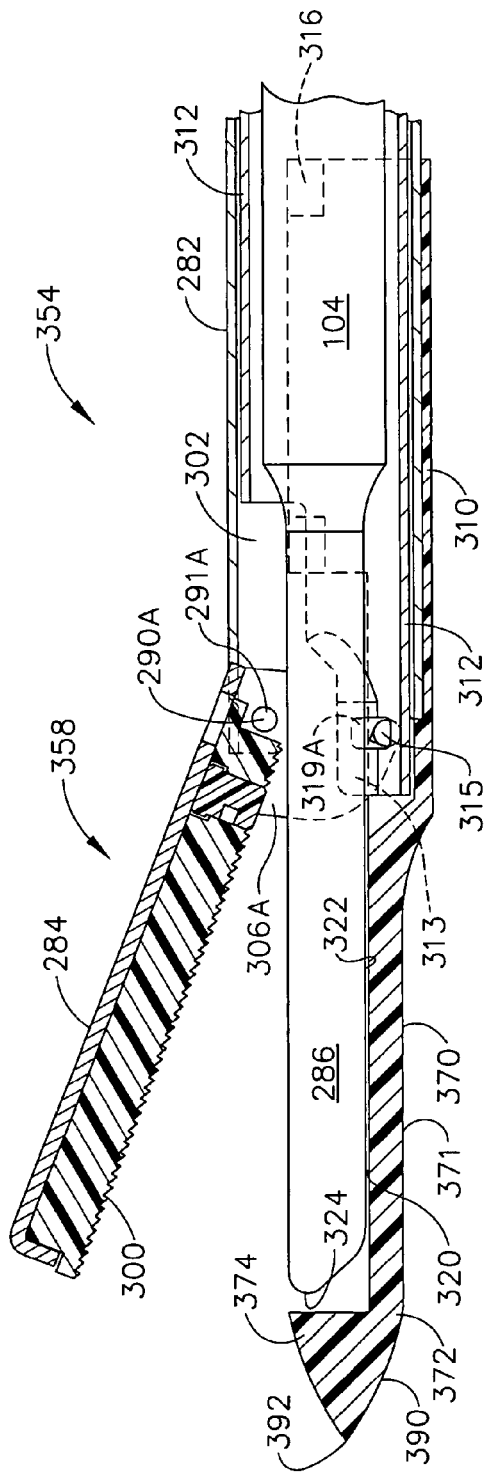
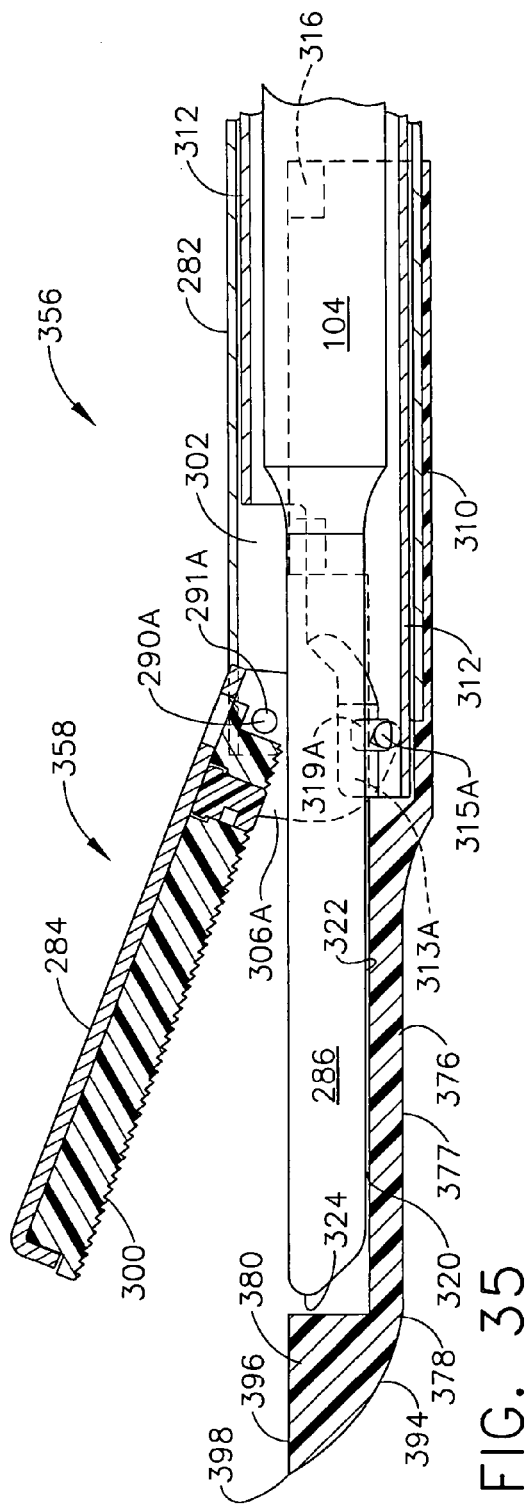
FIG. 34
FIG. 35

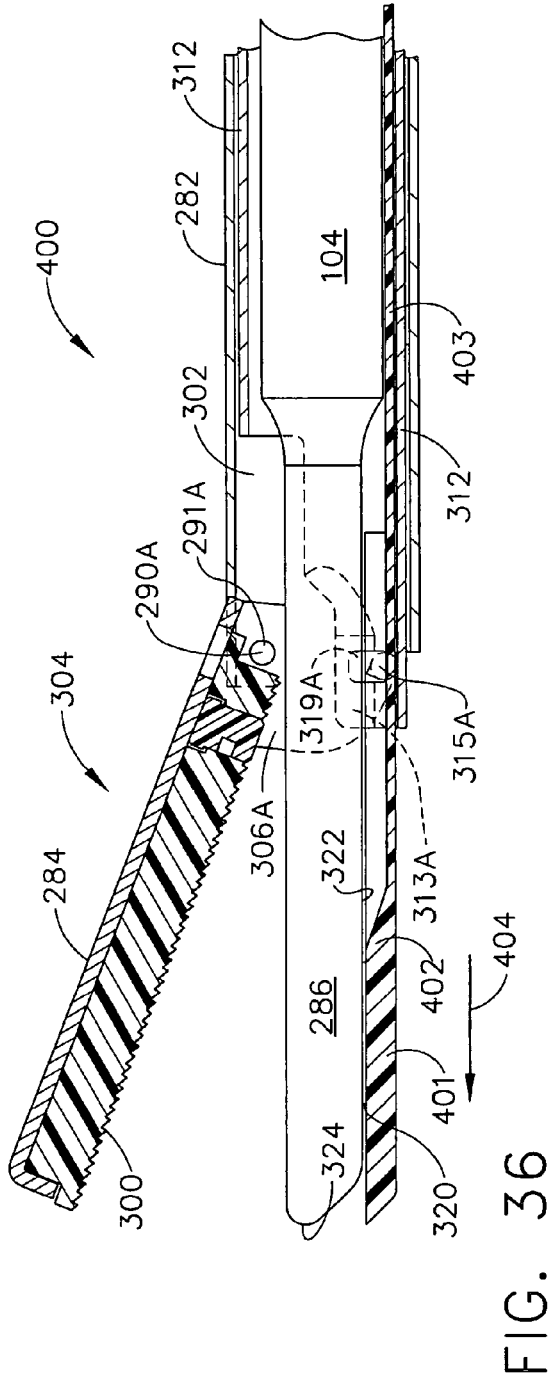
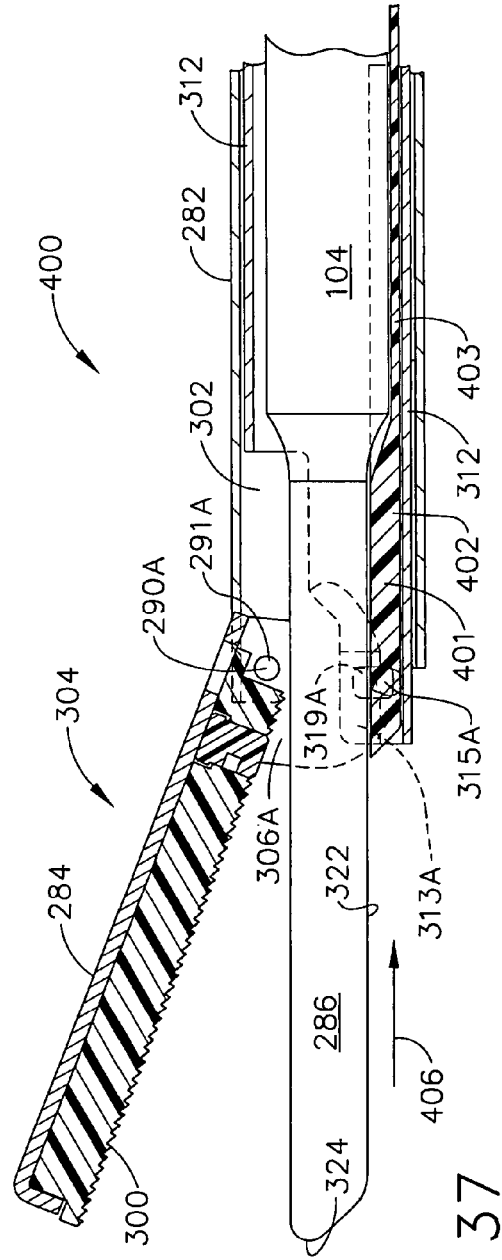
FIG. 36
FIG. 37

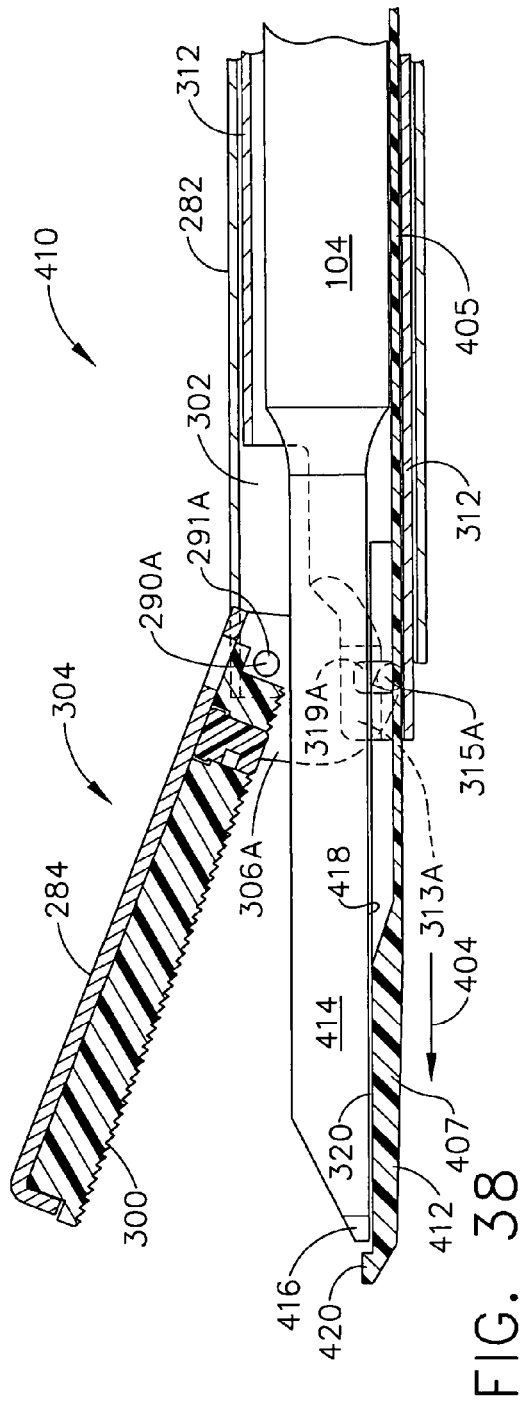
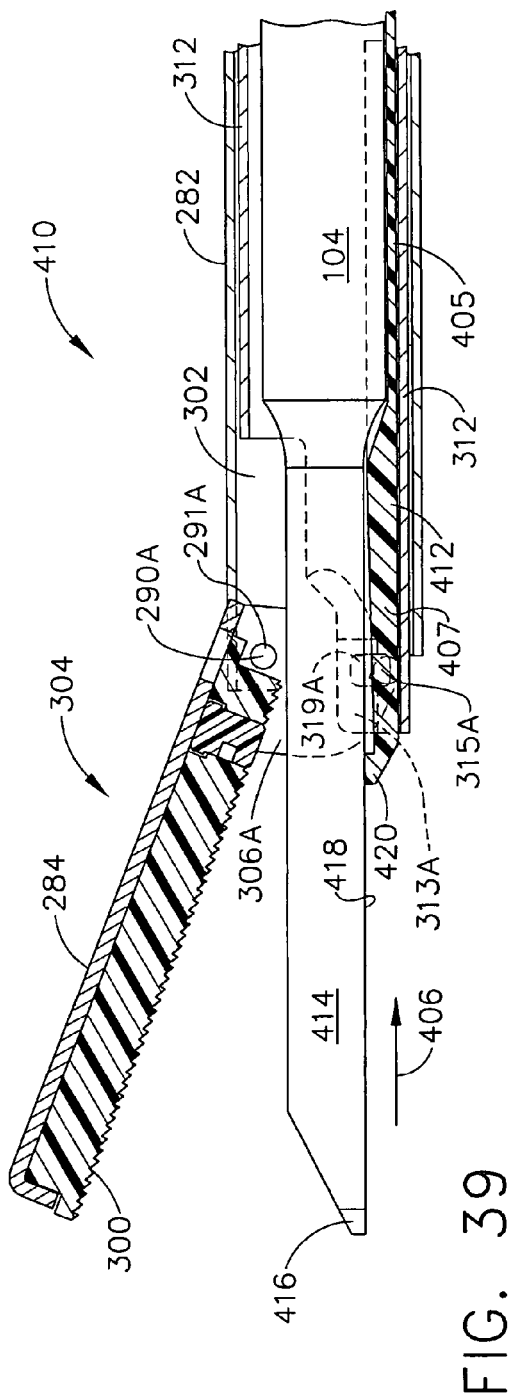

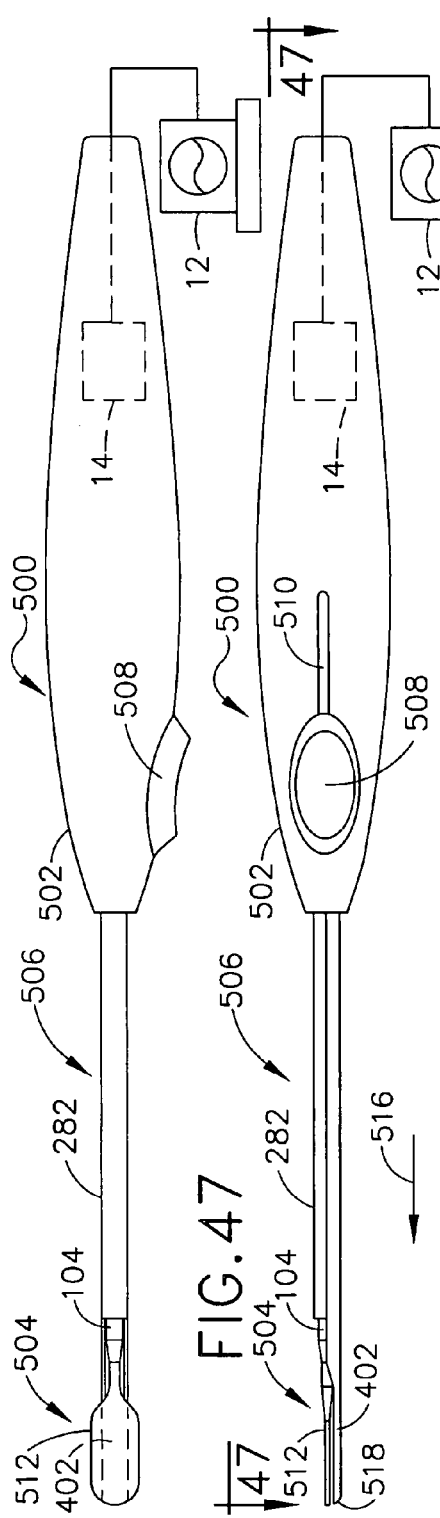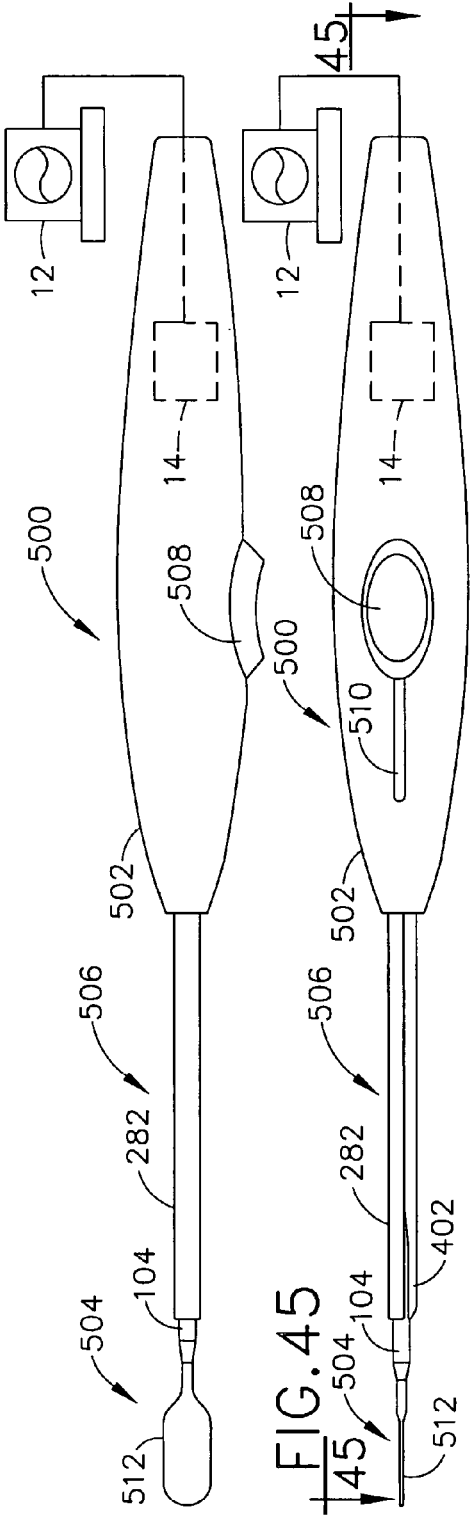

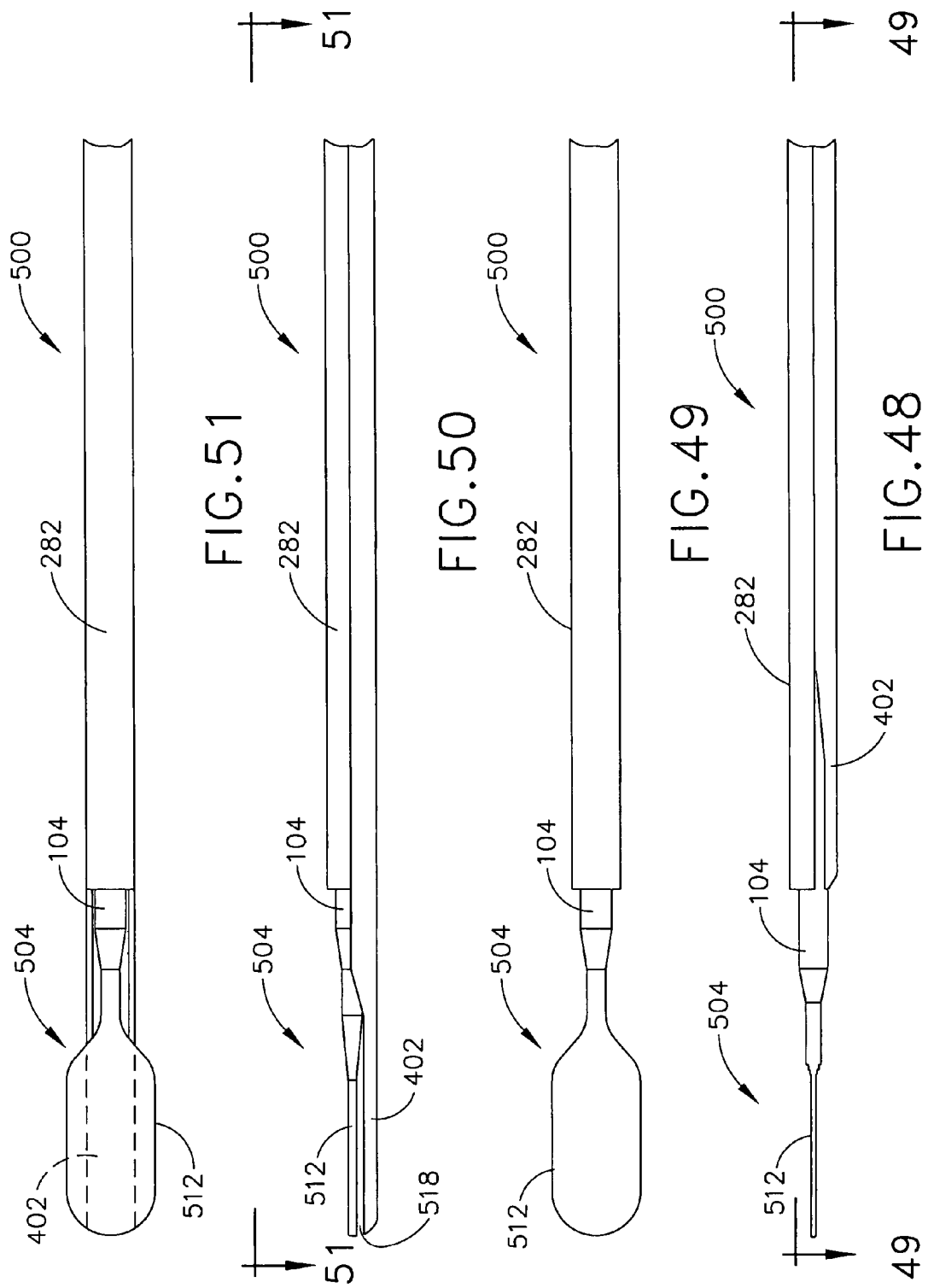

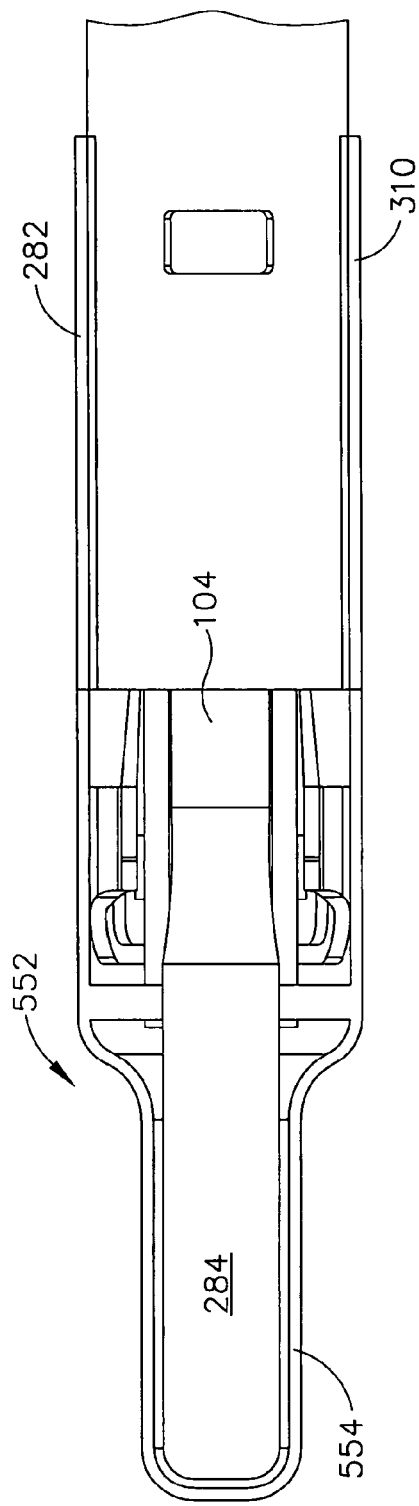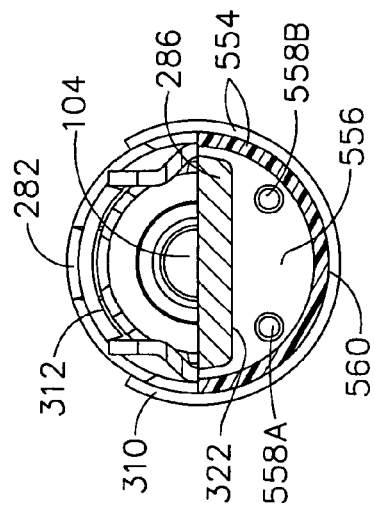
FIG. 55
FIG. 54

ULTRASONIC SURGICAL INSTRUMENT BLADES

BACKGROUND

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, elevate or cauterize tissue or to separate muscle tissue off bone. Ultrasonic instruments utilizing solid core technology are particularly advantageous because of the amount of ultrasonic energy that may be transmitted from the ultrasonic transducer, through a waveguide, to the surgical end effector. Such instruments may be used for open procedures or minimally invasive procedures, such as endoscopic or laparoscopic procedures, wherein the end effector is passed through a trocar to reach the surgical site.

Activating or exciting the end effector (e.g., cutting blade) of such instruments at ultrasonic frequencies induces longitudinal vibratory movement that generates localized heat within adjacent tissue, facilitating both cutting and coagulation. Because of the nature of ultrasonic instruments, a particular ultrasonically actuated end effector may be designed to perform numerous functions, including, for example, cutting and coagulation.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end effector via an ultrasonic waveguide extending from the transducer section to the surgical end effector. The waveguides and end effectors are designed to resonate at the same frequency as the transducer. Therefore, when an end effector is attached to a transducer the overall system frequency is the same frequency as the transducer itself.

The amplitude of the longitudinal ultrasonic vibration at the tip, d, of the end effector behaves as a simple sinusoid at the resonant frequency as given by:

$$d = A\sin(\omega t)$$

where:
$\omega$=the radian frequency which equals $2\pi$ times the cyclic frequency, f, and
A=the zero-to-peak amplitude.
The longitudinal excursion is defined as the peak-to-peak (p-t-p) amplitude, which is just twice the amplitude of the sine wave or 2A.

The shape of an ultrasonic surgical blade or end-effector used in an ultrasonic surgical instrument can define at least four important aspects of the instrument. These are: (1) the visibility of the end-effector and its relative position in the surgical field, (2) the ability of the end-effector to access or approach targeted tissue, (3) the manner in which ultrasonic energy is coupled to tissue for cutting and coagulation, and (4) the manner in which tissue can be manipulated with the ultrasonically inactive end-effector. It would be advantageous to provide an improved ultrasonic surgical instrument blade or end-effector optimizing at least these four aspects of the instrument.

However, as features are added to an ultrasonic surgical instrument blade to achieve the above-listed aspects, the shape of the blade is typically altered which creates asymmetries therein and causes the blade to become unbalanced, meaning that the blade can have the tendency to vibrate in directions other than the longitudinal direction along the length of the instrument, such as transverse directions. Substantial transverse motion in the blade and/or waveguide may lead to excess heat generation and/or premature stress failure therein. Long, thin ultrasonic waveguides, such as those used in instruments for minimally invasive surgery, are particularly susceptible to transverse vibrations introduced by imbalances, or asymmetries, in the end effector.

U.S. Pat. No. 6,283,981, which issued on Sep. 4, 2001 and is entitled METHOD OF BALANCING ASYMMETRIC ULTRASONIC SURGICAL BLADES, U.S. Pat. No. 6,309,400, which issued on Oct. 30, 2001 and is entitled CURVED ULTRASONIC BLADE HAVING A TRAPEZOIDAL CROSS SECTION, and U.S. Pat. No. 6,436,115, which issued on Aug. 20, 2002 and is entitled BALANCED ULTRASONIC BLADE INCLUDING A PLURALITY OF BALANCE ASYMMETRIES, the disclosures of which are hereby incorporated by reference herein, address balancing blades having asymmetries within a treatment portion of the blade by utilizing asymmetries within an adjacent balance portion. While such approaches have proven eminently successful, there are some applications where balancing may be desirable within the treatment, or functional, portion of a blade.

Solid core ultrasonic surgical instruments may be divided into two types, single element end effector devices and multiple-element end effector. Single element end effector devices include instruments such as scalpels, and ball coagulators. Single-element end effector instruments have limited ability to apply blade-to-tissue pressure when the tissue is soft and loosely supported. Substantial pressure may be necessary to effectively couple ultrasonic energy to the tissue. This inability to grasp the tissue results in a further inability to fully coat tissue surfaces while applying ultrasonic energy, leading to less-than-desired hemostasis and tissue joining. The use of multiple-element end effectors such as clamping coagulators includes a mechanism to press tissue against an ultrasonic blade that can overcome these deficiencies.

Ultrasonic clamp coagulators provide an improved ultrasonic surgical instrument for cutting/coagulating tissue, particularly loose and unsupported tissue, wherein the ultrasonic blade is employed in conjunction with a clamp for applying a compressive or biasing force to the tissue, whereby faster coagulation and cutting of the tissue, with less attenuation of blade motion, are achieved.

Surgical elevators are instruments used to help facilitate the elevation and removal of soft tissue during surgery. Surgical elevators are generally employed to separate muscle from bone. Cobb or curette type surgical elevators and used in spine surgery, especially to assist in posterior access in removing muscle tissue from bone. To remove muscle tissue from bone using conventional surgical elevators, the surgeon must exert a significant amount of force. This may cause premature fatigue. Also, using significant force on a conventional surgical elevator during this technique may increase the likelihood of error and unwanted tissue damage.

It would be desirable to provide an ultrasonic instrument comprising a surgical elevator blade to remove soft tissue such as muscle from bone and to perform additional surgical functions as well. Also, because ultrasonic frequencies induce longitudinal vibratory movements and generate localized heat within adjacent tissue it would be desirable to provide a protective material for the surgical elevator of such ultrasonic instrument. The protective material may reduce the possibility of blade breakage when in contact with bone or metal retractors and may decrease thermal spread from the back edge of the blade.

SUMMARY

In one general aspect, the various embodiments are directed to an ultrasonic surgical instrument that comprises a transducer configured to produce vibrations at a predetermined frequency. The transducer is configured to produce vibrations along a longitudinal axis at a predetermined frequency. An ultrasonic blade extends along the longitudinal axis and is coupled to the transducer. The ultrasonic blade includes a body having a proximal end and a distal end. The distal end is movable relative to the longitudinal axis by the vibrations produced by the transducer. The body includes a treatment region that extends from the proximal end to the distal end. The body includes a substantially flat broad top surface, a bottom surface, and a neck portion protruding from the proximal end adapted to couple to the transducer.

In at least one form of the invention, an ultrasonic surgical instrument can include an ultrasonically actuated blade or end effector having a treatment portion. In various embodiments, the blade can define a longitudinal axis and at least one axis which is transverse to the longitudinal axis. In at least one such embodiment, the transverse axis can lie within a plane which is perpendicular, or normal, to the longitudinal axis and can define a cross-section of the treatment portion. In various embodiments, such a cross-section can include a central portion and a step, wherein the step can extend from the central portion, wherein the central portion can comprise a width, and wherein the step can comprise a cutting edge. In at least one embodiment, the cutting edge can be defined by first and second surfaces which define an angle therebetween. In various embodiments, the position of the cutting edge and/or the angle between the cutting edge surfaces, for example, can be selected in order to balance the blade with respect to the transverse axis.

FIGURES

The novel features of the various embodiments are set forth with particularity in the appended claims. The various embodiments, however, both as to organization and methods of operation, together with further objects and advantages thereof, may best be understood by reference to the following description, taken in conjunction with the accompanying drawings as follows.

FIG. 4 is a side view of one embodiment of an ultrasonic blade;

FIG. 5 is a top view of the ultrasonic blade shown in FIG. 4;

FIG. 6 is a cross-sectional view of the ultrasonic blade taken along line 6-6 in FIG. 4; and FIG. 7 is a top perspective view of the ultrasonic blade shown in FIG. 4.

FIG. 8 is a side view of one embodiment of an ultrasonic blade;

FIG. 9 is a top view of the ultrasonic blade shown in FIG. 8;

FIG. 10 is a cross-sectional view of the ultrasonic blade taken along line 10-10 in FIG. 8; and FIG. 11 is a top perspective view of the ultrasonic blade shown in FIG. 8.

FIG. 12 is a side view of one embodiment of an ultrasonic blade;

FIG. 13 is a top view of the ultrasonic blade shown in FIG. 12;

FIG. 14 is a cross-sectional view of the ultrasonic blade taken along line 14-14 in FIG. 12; and FIG. 15 is a top perspective view of the ultrasonic blade shown in FIG. 12.

FIG. 16 is a side view of one embodiment of an ultrasonic blade;

FIG. 17 is a top view of the ultrasonic blade shown in FIG. 16;

FIG. 18 is an end-sectional view of the ultrasonic blade taken along line 18-18 in FIG. 16; and FIG. 19 is a top perspective view of the ultrasonic blade shown in FIG. 16.

FIG. 22 illustrates a partial cross-sectional view of one embodiment of an ultrasonic blade comprising a protective sheath taken along the longitudinal axis;

FIG. 23 is a bottom view of the ultrasonic blade taken along line 23-23 in FIG. 22; and FIG. 24 is a cross-sectional view of the ultrasonic blade and the protective sheath shown in FIG. 22.

FIGS. 27-31 illustrate one embodiment of an ultrasonic surgical instrument comprising an end effector, where:

FIG. 27 is a top perspective view of one embodiment of an ultrasonic surgical instrument;

FIG. 28 is a cross-sectional view of the ultrasonic surgical instrument shown in FIG. 27 taken along the longitudinal axis of the ultrasonic surgical instrument shown in FIG. 27;

FIG. 29 is a bottom view of the ultrasonic surgical instrument taken along lines 29-29 in FIG. 28;

FIG. 30 is a cross-sectional view of the ultrasonic surgical instrument taken along lines 30-30 in FIG. 28; and FIG. 31 is cross-sectional view of the ultrasonic surgical instrument taken along lines 31-31 in FIG. 28.

FIGS. 32-35 are cross-sectional views of various embodiments of ultrasonic surgical instruments taken along the longitudinal axis.

FIGS. 36-37 are cross-sectional views of one embodiment of an ultrasonic surgical instrument taken along the longitudinal axis.

FIGS. 38-39 are cross-sectional views of one embodiment of an ultrasonic surgical instrument taken along the longitudinal axis.

FIG. 41 is a side view of one embodiment of the ultrasonic system;

FIG. 42 is a cross-sectional side view of the ultrasonic system shown in FIG. 41 and a cross-sectional view of various tube assemblies to couple the hand piece housing with an end effector;

FIG. 43 is a bottom cross-sectional view of the ultrasonic instrument shown in FIG. 41.

FIGS. 44-51 illustrate one embodiment of an ultrasonic system, where:

FIG. 44 is a side view of one embodiment of a ultrasonic instrument with a deployable protective sheath in a stowed or retracted position;

FIG. 45 is a top view of the ultrasonic instrument with the deployable protective sheath in the stowed or retracted position taken along line 45-45 in FIG. 44;

FIG. 46 is a side view of the ultrasonic instrument shown in FIG. 44 with the deployable protective sheath in a deployed position;

FIG. 47 is a top view of the ultrasonic instrument in the deployed position taken along line 47-47 in FIG. 46;

FIG. 48 is a more detailed side view of the ultrasonic instrument shown in FIG. 44 with the deployable protective sheath in a stowed or retracted position;

FIG. 49 is a more detailed top view of the ultrasonic instrument shown in FIG. 45 with the protective sheath in the stowed or retracted position taken along line 49-49 in FIG. 48;

FIG. 50 is a more detailed side view of the ultrasonic instrument shown in FIG. 46 with the deployable protective sheath in a deployed position; and FIG. 51 is a more detailed top view of the ultrasonic instrument shown in FIG. 47 in the deployed position taken along line 51-51 in FIG. 50.

FIGS. 52-55 illustrate one embodiment of an ultrasonic surgical instrument comprising an end effector, where:

FIG. 52 is a top perspective view of one embodiment of an ultrasonic surgical instrument;

FIG. 53 is a partial cross-sectional view of the ultrasonic surgical instrument shown in FIG. 52 taken along the longitudinal axis of the ultrasonic surgical instrument;

FIG. 54 is a cross-sectional view of the ultrasonic surgical instrument taken along lines 54-54 shown in FIG. 53; and FIG. 55 is a top view of the ultrasonic surgical instrument.

FIG. 56 is a side view of one embodiment of an ultrasonic blade;

FIG. 57 is a top view of the ultrasonic blade shown in FIG. 56;

FIG. 58 is a cross-sectional view of the ultrasonic blade taken along line 58-58 in FIG. 57; and FIG. 59 is a top perspective view of the ultrasonic blade shown in FIG. 56.

DESCRIPTION

Figure 1:
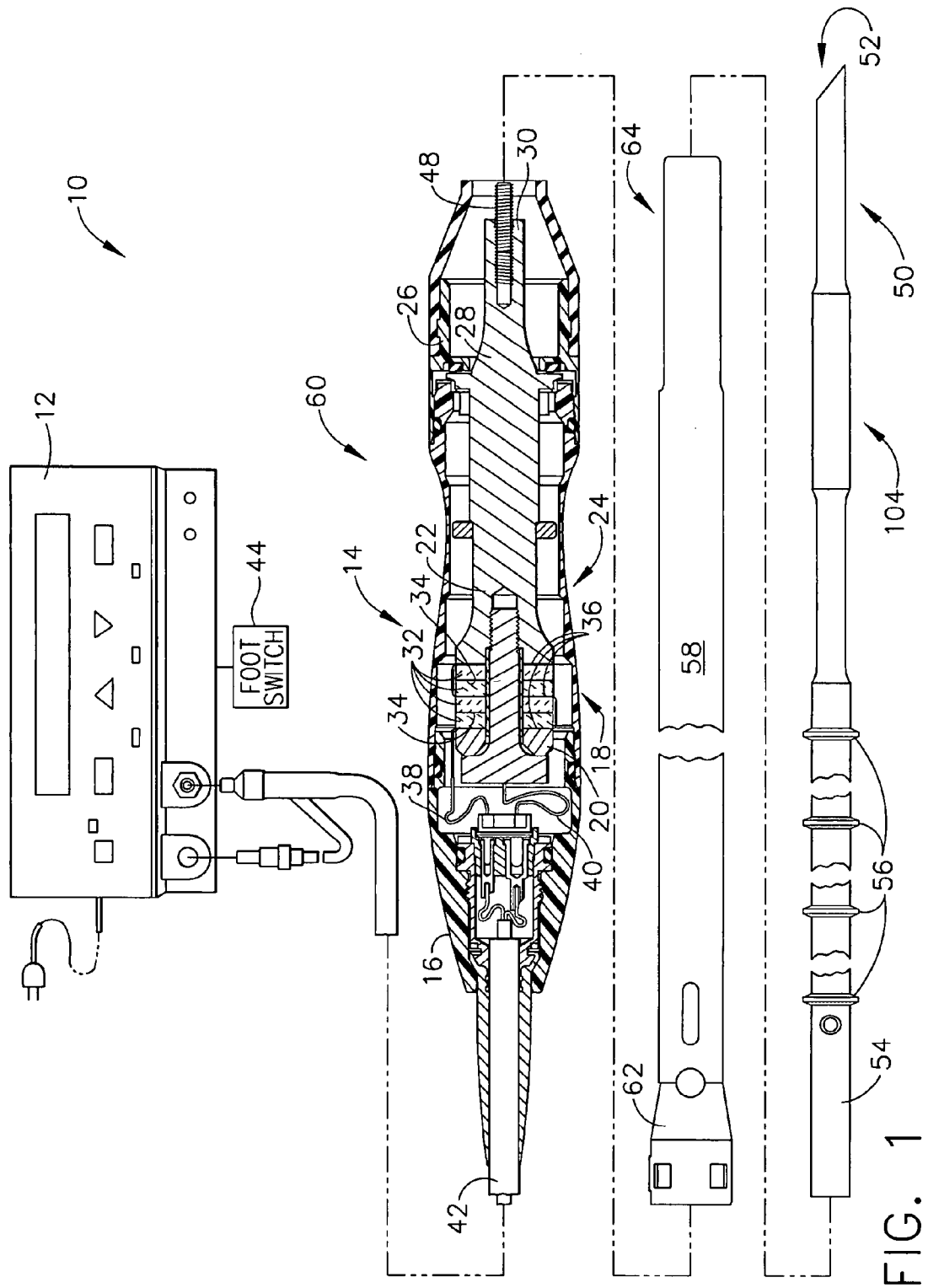
FIG. 1 illustrates one embodiment of an ultrasonic system.

Before explaining the various embodiments in detail, it should be noted that the embodiments are not limited in its application or use to the details of construction and arrangement of parts illustrated in the accompanying drawings and description. The illustrative embodiments may be implemented or incorporated in other embodiments, variations and modifications, and may be practiced or carried out in various ways. For example, the surgical instruments and blade configurations disclosed below are illustrative only and not meant to limit the scope or application thereof. Furthermore, unless otherwise indicated, the terms and expressions employed herein have been chosen for the purpose of describing the illustrative embodiments for the convenience of the reader and are not to limit the scope thereof.

The various embodiments relate, in general, to ultrasonic surgical blades for use in surgical instruments and, more particularly, to an ultrasonic surgical blade with improved elevator, cutting and coagulation features and to an ultrasonic blade comprising a protective sheath on a portion thereof. The various embodiments relate, in general, to ultrasonic surgical blades and instruments for improved bone and tissue removal, aspiration, and coagulation features. A blade according to various embodiments is of particular benefit, among others, in orthopedic procedures wherein it is desirable to remove cortical bone and/or tissue while controlling bleeding for removing muscle tissue from bone, due to its cutting and coagulation characteristics. The blade, however, may be useful for general soft tissue cutting and coagulation. The blade may be straight or curved, and useful for either open or laparoscopic applications. A blade according to various embodiments may be useful in spine surgery, especially to assist in posterior access in removing muscle from bone. A blade according to the various embodiments may reduce the user force required to remove muscle from bone and, in one embodiment, may be useful to simultaneously hemostatically seal or cauterize the tissue. Reducing the force to operate the surgical instrument may reduce user fatigue, improve precision and reduce unwanted tissue damage. A variety of different blade configurations are disclosed which may be useful for both open and laparoscopic applications.

Examples of ultrasonic surgical instruments are disclosed in U.S. Pat. Nos. 5,322,055 and 5,954,736 and in combination with ultrasonic blades and surgical instruments disclosed in U.S. Pat. Nos. 6,309,400 B2, 6,278,218B1, 6,283,981 B1, and 6,325,811 B1, for example, are incorporated herein by reference in their entirety. Also incorporated by reference in its entirety is commonly-owned, co-pending U.S. patent application Ser. No. 11/726,625, entitled ULTRASONIC SURGICAL INSTRUMENTS, filed on Mar. 22, 2007. Some of these references disclose ultrasonic surgical instrument design and blade designs where a longitudinal node of the blade is excited. Because of asymmetry or asymmetries, these blades exhibit transverse and/or torsional motion where the characteristic "wavelength" of this non-longitudinal motion is less than that of the general longitudinal motion of the blade and its extender portion. Therefore, the wave shape of the non-longitudinal motion will present nodal positions of transverse/torsional motion along the tissue effector while the net motion of the active blade along its tissue effector is non-zero (i.e. will have at least longitudinal motion along the length extending from its distal end, an antinode of longitudinal motion, to the first nodal position of longitudinal motion that is proximal to the tissue effector portion). Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments is defined solely by the claims. The features illustrated or described in connection with one exemplary embodiment may be combined with the features of other embodiments. Such modifications and variations are intended to be included within the scope of the claims.

FIG. 1 illustrates one embodiment of an ultrasonic system 10. One embodiment of the ultrasonic system 10 comprises an ultrasonic signal generator 12 coupled to an ultrasonic transducer 14, a hand piece assembly 60 comprising a hand piece housing 16, and an end effector 50. The ultrasonic transducer 14, which is known as a "Langevin stack", generally includes a transduction portion 18, a first resonator or end-bell 20, and a second resonator or fore-bell 22, and ancillary components. The ultrasonic transducer 14 is preferably an integral number of one-half system wavelengths (nλ/2) in length as will be described in more detail later. An acoustic assembly 24 includes the ultrasonic transducer 14, a mount 26, a velocity transformer 28, and a surface 30.

It will be appreciated that the terms "proximal" and "distal" are used herein with reference to a clinician gripping the hand piece assembly 60. Thus, the end effector 50 is distal with respect to the more proximal hand piece assembly 60. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The distal end of the end-bell 20 is connected to the proximal end of the transduction portion 18, and the proximal end of the fore-bell 22 is connected to the distal end of the transduction portion 18. The fore-bell 22 and the end-bell 20 have a length determined by a number of variables, including the thickness of the transduction portion 18, the density and modulus of elasticity of the material used to manufacture the end-bell 20 and the fore-bell 22, and the resonant frequency of the ultrasonic transducer 14. The fore-bell 22 may be tapered inwardly from its proximal end to its distal end to amplify the ultrasonic vibration amplitude as the velocity transformer 28, or alternately may have no amplification. A suitable vibrational frequency range may be about 20 Hz to 120 kHz and a well-suited vibrational frequency range may be about 30-70 kHz and one example operational vibrational frequency may be approximately 55.5 kHz.

Piezoelectric elements 32 may be fabricated from any suitable material, such as, for example, lead zirconate-titanate, lead meta-niobate, lead titanate, or other piezoelectric crystal material. Each of positive electrodes 34, negative electrodes 36, and the piezoelectric elements 32 has a bore extending through the center. The positive and negative electrodes 34 and 36 are electrically coupled to wires 38 and 40, respectively. The wires 38 and 40 are encased within a cable 42 and electrically connectable to the ultrasonic signal generator 12 of the ultrasonic system 10.

The ultrasonic transducer 14 of the acoustic assembly 24 converts the electrical signal from the ultrasonic signal generator 12 into mechanical energy that results in primarily longitudinal vibratory motion of the ultrasonic transducer 24 and the end effector 50 at ultrasonic frequencies. A suitable generator is available as model number GEN01, from Ethicon Endo-Surgery, Inc., Cincinnati, Ohio. When the acoustic assembly 24 is energized, a vibratory motion standing wave is generated through the acoustic assembly 24. The amplitude of the vibratory motion at any point along the acoustic assembly 24 may depend upon the location along the acoustic assembly 24 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node (i.e., where motion is usually maximal). The distance between an anti-node and its nearest node is one-quarter wavelength (λ/4).

The wires 38 and 40 transmit an electrical signal from the ultrasonic signal generator 12 to the positive electrodes 34 and the negative electrodes 36. The piezoelectric elements 32 are energized by the electrical signal supplied from the ultrasonic signal generator 12 in response to a foot switch 44 to produce an acoustic standing wave in the acoustic assembly 24. The electrical signal causes disturbances in the piezoelectric elements 32 in the form of repeated small displacements resulting in large compression forces within the material. The repeated small displacements cause the piezoelectric elements 32 to expand and contract in a continuous manner along the axis of the voltage gradient, producing longitudinal waves of ultrasonic energy. The ultrasonic energy is transmitted through the acoustic assembly 24 to the end effector 50 via a an ultrasonic transmission waveguide 104.

In order for the acoustic assembly 24 to deliver energy to the end effector 50, all components of the acoustic assembly 24 must be acoustically coupled to the end effector 50. The distal end of the ultrasonic transducer 14 may be acoustically coupled at the surface 30 to the proximal end of the ultrasonic transmission waveguide 104 by a threaded connection such as a stud 48.

The components of the acoustic assembly 24 are preferably acoustically tuned such that the length of any assembly is an integral number of one-half wavelengths (nλ/2), where the wavelength λ is the wavelength of a pre-selected or operating longitudinal vibration drive frequency $f_d$ of the acoustic assembly 24, and where n is any positive integer. It is also contemplated that the acoustic assembly 24 may incorporate any suitable arrangement of acoustic elements.

The ultrasonic end effector 50 may have a length substantially equal to an integral multiple of one-half system wavelengths (λ/2). A distal end 52 of the ultrasonic end effector 50 may be disposed near an antinode in order to provide the maximum longitudinal excursion of the distal end. When the transducer assembly is energized, the distal end 52 of the ultrasonic end effector 50 may be configured to move in the range of, for example, approximately 10 to 500 microns peak-to-peak, and preferably in the range of about 30 to 150 microns at a predetermined vibrational frequency.

The ultrasonic end effector 50 may be coupled to the ultrasonic transmission waveguide 104. The ultrasonic end effector 50 and the ultrasonic transmission guide 104 as illustrated are formed as a single unit construction from a material suitable for transmission of ultrasonic energy such as, for example, Ti6Al4V (an alloy of Titanium including Aluminum and Vanadium), Aluminum, Stainless Steel, or other known materials. Alternately, the ultrasonic end effector 50 may be separable (and of differing composition) from the ultrasonic transmission waveguide 104, and coupled by, for example, a stud, weld, glue, quick connect, or other suitable known methods. The ultrasonic transmission waveguide 104 may have a length substantially equal to an integral number of one-half system wavelengths ($\lambda/2$), for example. The ultrasonic transmission waveguide 104 may be preferably fabricated from a solid core shaft constructed out of material that propagates ultrasonic energy efficiently, such as titanium alloy (i.e., Ti-6Al-4V) or an aluminum alloy, for example.

The ultrasonic transmission waveguide 104 comprises a longitudinally projecting attachment post 54 at a proximal end to couple to the surface 30 of the ultrasonic transmission waveguide 104 by a threaded connection such as the stud 48. In the embodiment illustrated in FIG. 1, the ultrasonic transmission waveguide 104 comprises a plurality of stabilizing silicone rings or compliant supports 56 positioned at a plurality of nodes. The silicone rings 56 dampen undesirable vibration and isolate the ultrasonic energy from a removable sheath 58 assuring the flow of ultrasonic energy in a longitudinal direction to the distal end 52 of the end effector 50 with maximum efficiency.

As shown in FIG. 1, the removable sheath 58 is coupled to the distal end of the handpiece assembly 60. The sheath 58 generally includes an adapter or nose cone 62 and an elongated tubular member 64. The tubular member 64 is attached to the adapter 62 and has an opening extending longitudinally therethrough. The sheath 58 may be threaded or snapped onto the distal end of the housing 16. The ultrasonic transmission waveguide 104 extends through the opening of the tubular member 64 and the silicone rings 56 isolate the ultrasonic transmission waveguide 104 therein.

The adapter 62 of the sheath 58 is preferably constructed from Ultem®, and the tubular member 64 is fabricated from stainless steel. Alternatively, the ultrasonic transmission waveguide 104 may have polymeric material surrounding it to isolate it from outside contact.

The distal end of the ultrasonic transmission waveguide 104 may be coupled to the proximal end of the end effector 50 by an internal threaded connection, preferably at or near an antinode. It is contemplated that the end effector 50 may be attached to the ultrasonic transmission waveguide 104 by any suitable means, such as a welded joint or the like. Although the end effector 50 may be detachable from the ultrasonic transmission waveguide 104, it is also contemplated that the end effector 50 and the ultrasonic transmission waveguide 104 may be formed as a single unitary piece.

Figure 2:
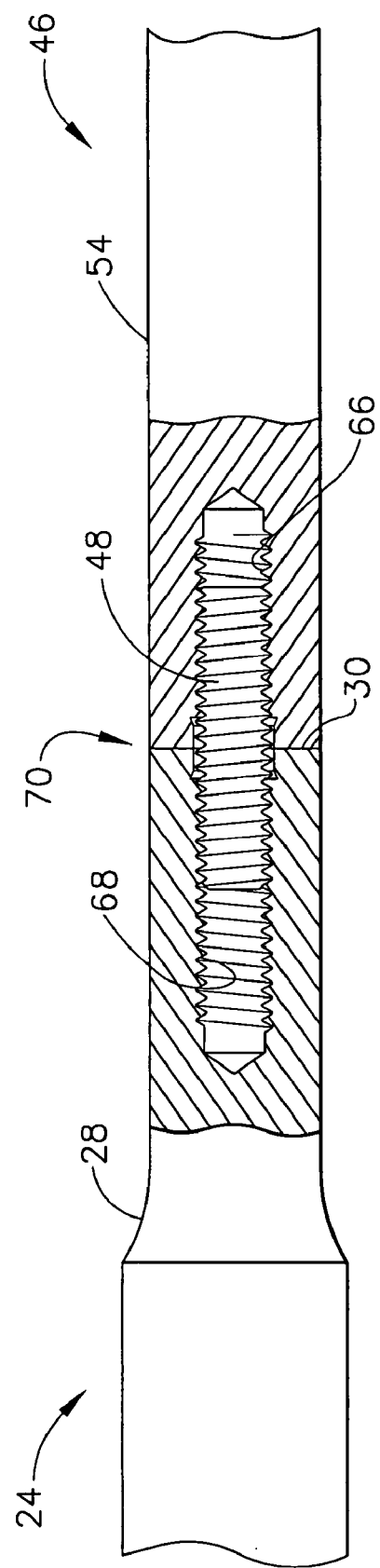
FIG. 2 illustrates one embodiment of a connection union/joint for an ultrasonic instrument.

FIG. 2 illustrates one embodiment of a connection union/joint 70 for an ultrasonic instrument. The connection union/joint 70 may be formed between the attachment post 54 of the ultrasonic transmission waveguide 104 and the surface 30 of the velocity transformer 28 at the distal end of the acoustic assembly 24. The proximal end of the attachment post 54 comprises a female threaded substantially cylindrical recess 66 to receive a portion of the threaded stud 48 therein. The distal end of the velocity transformer 28 also may comprise a female threaded substantially cylindrical recess 68 to receive a portion of the threaded stud 40. The recesses 66, 68 are substantially circumferentially and longitudinally aligned.

Figure 3:
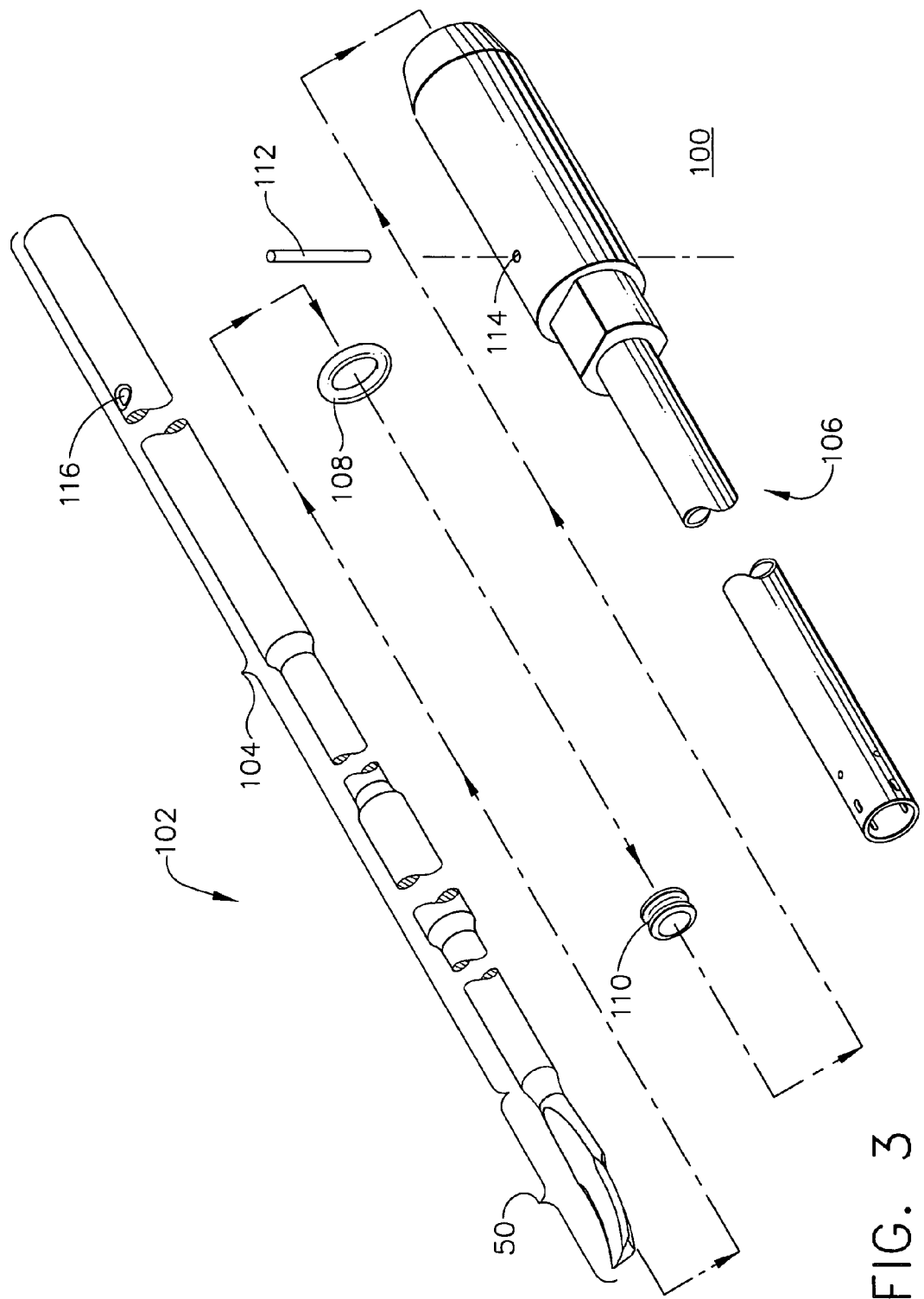
FIG. 3 illustrates an exploded perspective view of one embodiment of a sterile ultrasonic surgical instrument.

FIG. 3 illustrates an exploded perspective view of one embodiment of a sterile ultrasonic surgical instrument 100. The ultrasonic surgical instrument 100 may be employed with the above-described ultrasonic system 10. However, as described herein, those of ordinary skill in the art will understand that the various embodiments of the ultrasonic surgical instruments disclosed herein as well as any equivalent structures thereof could conceivably be effectively used in connection with other known ultrasonic surgical instruments without departing from the scope thereof. Thus, the protection afforded to the various ultrasonic surgical blade embodiments disclosed herein should not be limited to use only in connection with the exemplary ultrasonic surgical instrument described above.

The ultrasonic surgical instrument 100 may be sterilized by methods known in the art such as, for example, gamma radiation sterilization, Ethelyne Oxide processes, autoclaving, soaking in sterilization liquid, or other known processes. In the illustrated embodiment, an ultrasonic transmission assembly 102 includes an ultrasonic end effector, the generally designated ultrasonic end effector 50, and the ultrasonic transmission waveguide 104. The ultrasonic end effector 50 and the ultrasonic transmission waveguide 104 are illustrated as a single unit construction from a material suitable for transmission of ultrasonic energy such as, for example, Ti6Al4V (an alloy of Titanium including Aluminum and Vanadium), Aluminum, Stainless Steel, or other known materials. Alternately, the ultrasonic end effector 50 may be separable (and of differing composition) from the ultrasonic transmission waveguide 104, and coupled by, for example, a stud, weld, glue, quick connect, or other known methods. The ultrasonic transmission waveguide 104 may have a length substantially equal to an integral number of one-half system wavelengths ($n\lambda/2$), for example. The ultrasonic transmission waveguide 104 may be preferably fabricated from a solid core shaft constructed out of material that propagates ultrasonic energy efficiently, such as titanium alloy (i.e., Ti-6Al-4V) or an aluminum alloy, for example.

In the embodiment illustrated in FIG. 3, the ultrasonic transmission waveguide 104 is positioned in an outer sheath 106 by a mounting O-ring 108 and a sealing ring 110. One or more additional dampers or support members (not shown) also may be included along the ultrasonic transmission waveguide 104. The ultrasonic transmission waveguide 104 is affixed to the outer sheath 106 by a mounting pin 112 that passes through mounting holes 114 in the outer sheath 106 and a mounting slot 116 in the ultrasonic transmission waveguide 104.

FIGS. 4-19 illustrate various embodiments of ultrasonic blades, which may be considered different embodiments of the end effector 50 and are generally well-suited for cutting, coagulating, and reshaping tissue. In various embodiments, the ultrasonic blades may be configured as ultrasonic surgical elevator blades that are well-suited for separating muscle from bone, for example. The ultrasonic blades may be employed in the above-described ultrasonic surgical instruments 10, 100. Embodiments of the ultrasonic blades may be suitable in spine surgery, and more particularly, to assist in posterior access in removing muscle tissue from bone and coagulating the tissue. Accordingly, the ultrasonic blades may be employed to simultaneously reshape or remove muscle tissue from bone and to hemostatically seal the tissue as it is removed from the bone. The ultrasonic energy assists the cutting action of the ultrasonic blade and reduces the force required by a surgeon during an operation and thereby reduces surgeon fatigue, improves precision, and reduces unwanted tissue damage. The embodiments, however, are not limited in this context. Those skilled in the art will appreciate that although the various embodiments of the ultrasonic blades are well-suited for cutting, coagulating, and reshaping tissue, e.g., to separate muscle tissue from bone, these ultrasonic blades are multifunctional and may be employed in multiple numerous applications.

Figure 4:
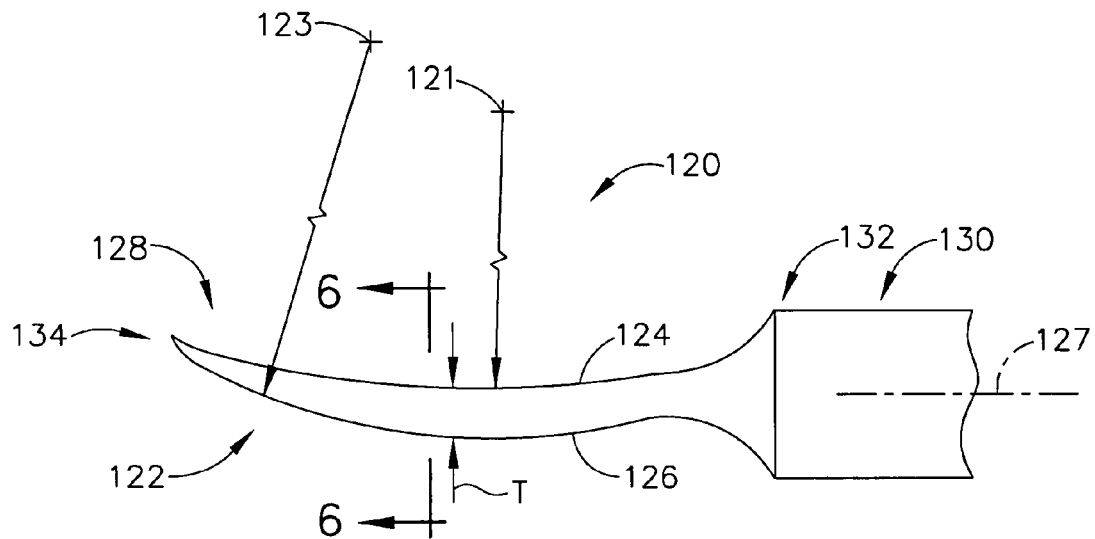
FIGS. 4-7 illustrate one embodiment of an ultrasonic blade, where.
Figure 5:
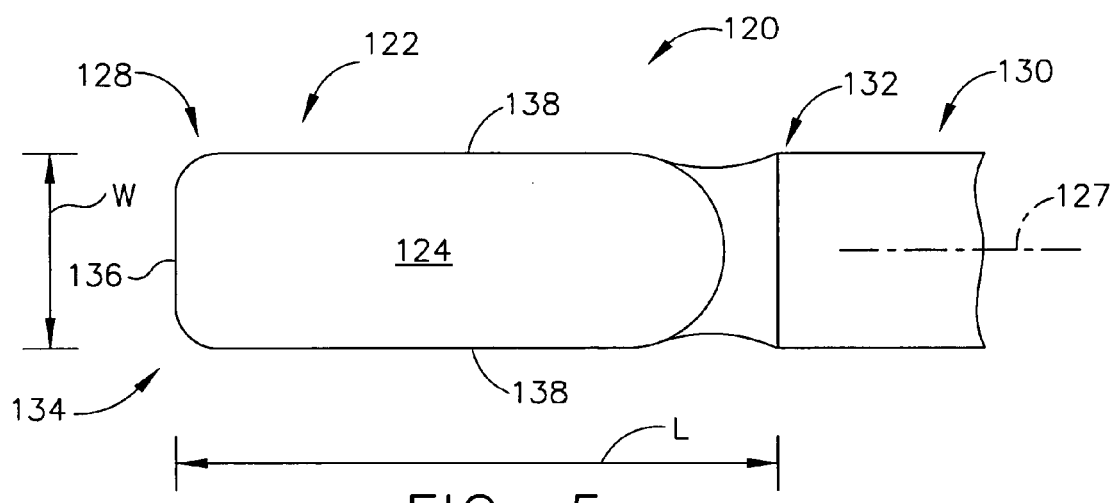
Figure 6:
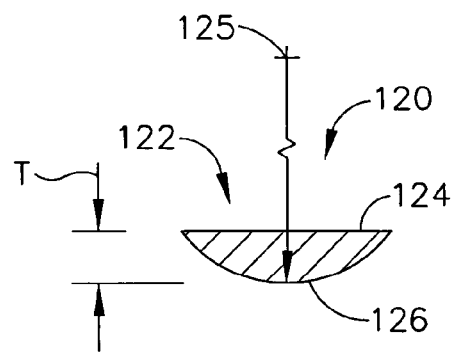
Figure 7:
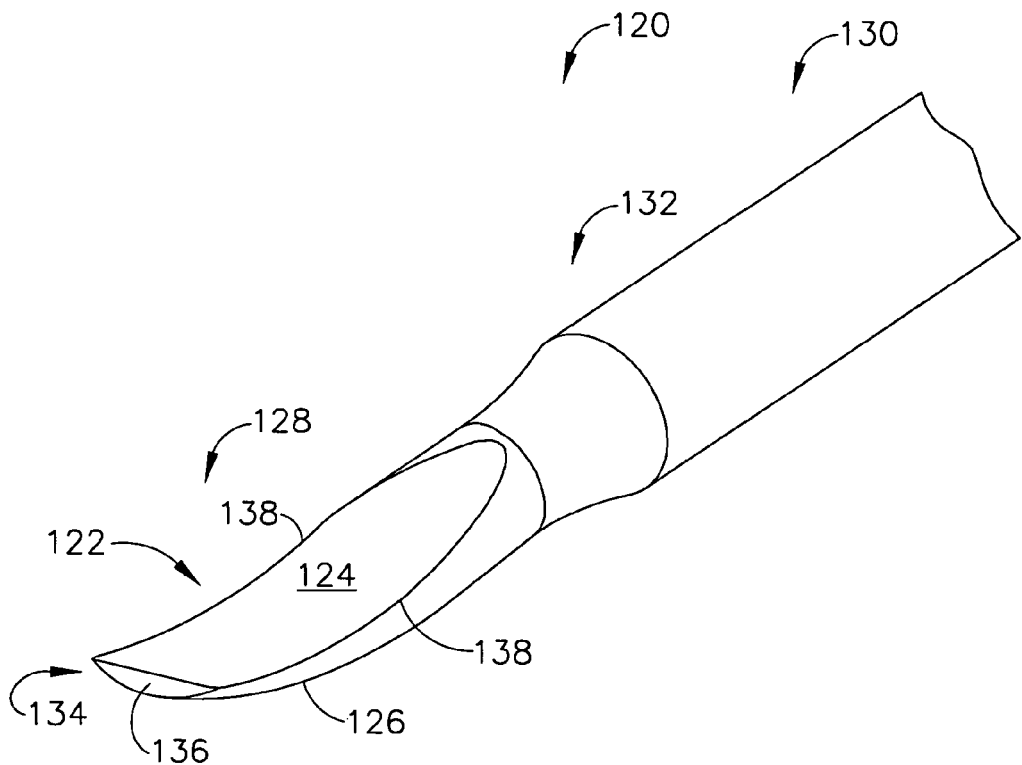

FIGS. 4-7 illustrate one embodiment of an ultrasonic blade 120. The ultrasonic blade 120 is generally well-suited for cutting, coagulating, and reshaping tissue. In one embodiment the ultrasonic blade 120 may be configured as an ultrasonic surgical elevator blade generally well-suited to separate muscle tissue from bone. Nevertheless, the ultrasonic blade 120 may be employed in various other therapeutic procedures. FIG. 4 is a side view of the ultrasonic blade 120. FIG. 5 is a top view of the ultrasonic blade 120. FIG. 6 is a cross-sectional view of the ultrasonic blade 120 taken along line 6-6 in FIG. 4. FIG. 7 is a top perspective view of the ultrasonic blade 120.

In the embodiment illustrated in FIGS. 4-7, the ultrasonic blade 120 comprises a blade body 122 having a generally flat top surface 124 that is substantially arcuate about a first axis 121 and a smooth generally round bottom surface 126 that is substantially arcuate about a second axis 123. As shown in the cross-sectional view of FIG. 6, the top surface 124 is generally flat and the bottom surface 126 is substantially arcuate with respect to a third axis 125. The blade body 122 extends along a longitudinal central axis 127. The blade body 122 may comprise a substantially elongated treatment region, generally designated as 128, and a neck or transition portion 130 that protrudes from a proximal end 132 of the treatment region 128. The neck portion 130 may be attached to the ultrasonic transmission waveguide 104 by a stud, weld, glue, quick connect, or other known attachment methods, for example. In alternative embodiments, the ultrasonic blade 120 and the ultrasonic transmission waveguide 104 may be formed as a single unitary body. In either configuration, the ultrasonic transmission waveguide 104 amplifies the mechanical vibrations transmitted to the ultrasonic blade 120 as is well known in the art. The ultrasonic blade 120 is adapted to couple to the ultrasonic surgical instrument 100, which may be employed with the above-described ultrasonic surgical instruments 10, 100.

The ultrasonic blade 120 comprises a treatment region 128 to effect tissue, such as, for example, cut, coagulate, reshape, scrape, and remove tissue. The treatment region 128 comprises the top surface 124 which is substantially arcuate about the first axis 121 and the smooth bottom surface 126 which is substantially arcuate about the second axis 123. As shown in the cross-sectional view in FIG. 6, the treatment region 128 the top surface 124 is generally flat and the bottom surface 126 is substantially arcuate about the third axis 125. A distal end 134 of the treatment region 128 also comprises a substantially flat tip with a cutting edge 136. The blade 120 and the distal cutting edge 136 define a broad top surface 124 for effecting tissue. The bottom surface 126 may be a surface for bone contact and atraumatic use along the bone region configured to prevent the cutting edge 136 from cutting into bone tissue. Due to its arcuate shape the bottom surface 126 may be employed to coagulate tissue. The top surface 124 of the blade 120 has a width "W" that is substantially greater than a thickness "T" of the blade 120. Additional cutting edges 138 may be positioned laterally along both sides of the treatment region 128. In one embodiment, the cutting edges 138 extend from the proximal end 132 to the distal end 134 of the treatment region 128. In one example, the flat tip cutting edge 136 or the lateral cutting edges 138 of the ultrasonic blade 120 are suitable to remove muscle tissue from bone while the smooth generally round substantially arcuate bottom surface 126 acts as an atraumatic surface that glides against the bone.

The ultrasonic blade 120 may be fabricated from a material suitable for transmission of ultrasonic energy such as, for example, Ti6Al4V (an alloy of Titanium including Aluminum and Vanadium), Aluminum, Stainless Steel, or other known materials.

Figure 8:
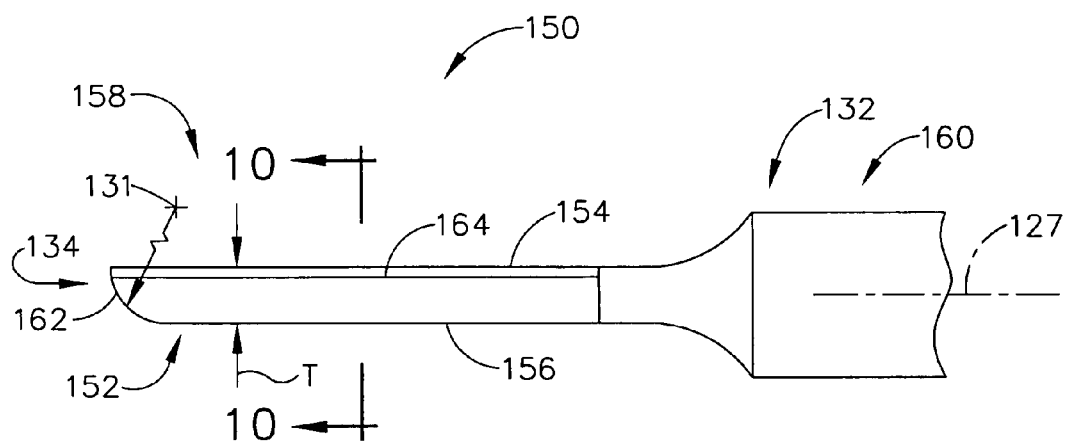
FIGS. 8-11 illustrate one embodiment of an ultrasonic blade, where.
Figure 9:
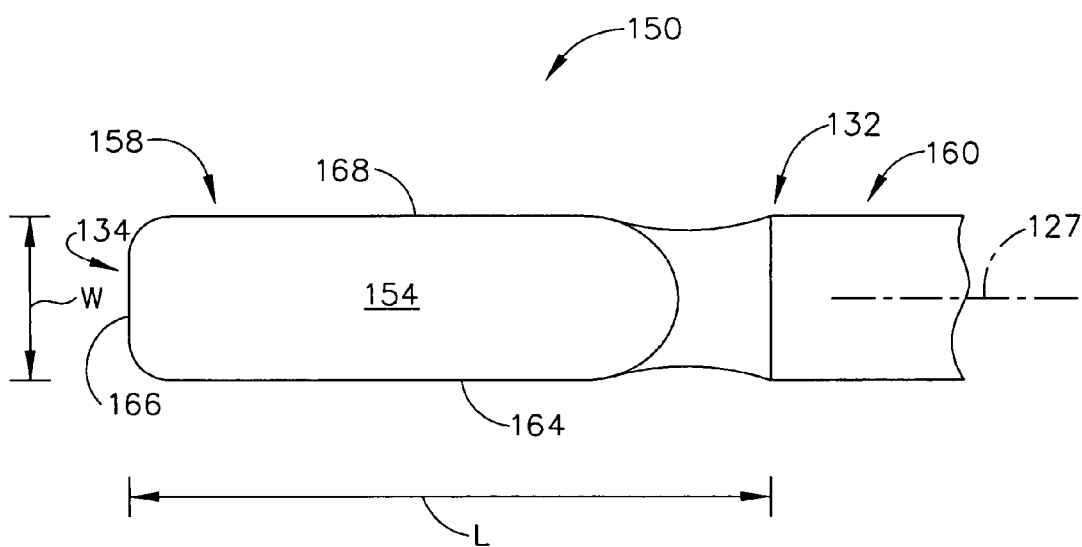
Figure 10:
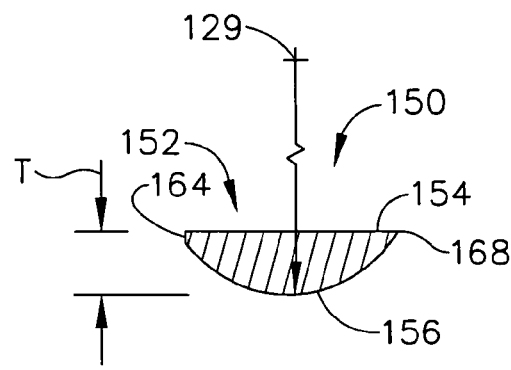
Figure 11:
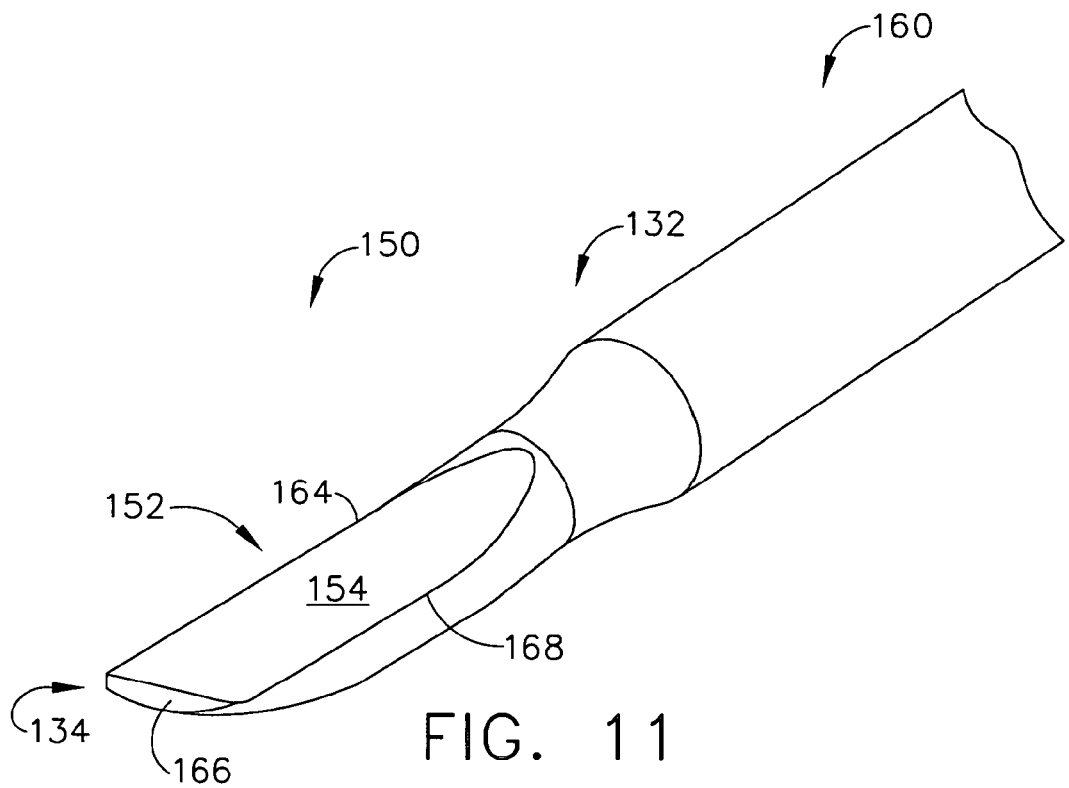

FIGS. 8-11 illustrate one embodiment of an ultrasonic blade 150. The ultrasonic blade 150 is generally well-suited for cutting, coagulating, and reshaping tissue. In one embodiment the ultrasonic blade 150 may be configured as an ultrasonic surgical elevator blade generally well-suited to separate muscle tissue from bone. Nevertheless, the ultrasonic blade 150 may be employed in various other therapeutic procedures. FIG. 8 is a side view of the ultrasonic blade 150. FIG. 9 is a top view of the ultrasonic blade 150. FIG. 10 is a cross-sectional view of the ultrasonic blade 150 taken along line 10-10 in FIG. 8. FIG. 11 is a top perspective view of the ultrasonic blade 150.

In the embodiment illustrated in FIGS. 8-11, the ultrasonic blade 150 comprises a blade body 152 having a generally flat planar top surface 154 and a smooth substantially arcuate bottom surface 156. The top and bottom surfaces 154, 56 extend along the longitudinal central axis 127. As shown in the cross-sectional view of FIG. 10, the top surface 154 is generally flat and planar and the bottom surface 156 is substantially arcuate about axis 129. The blade body 152 may comprise a substantially elongated treatment region, generally designated as 158, and a neck or transition portion 160 that protrudes from a proximal end 132 of the treatment region 158. The neck portion 160 may be attached to the ultrasonic transmission waveguide 104 by a stud, weld, glue, quick connect, or other known attachment methods, for example. In alternative embodiments, the ultrasonic blade 150 and the waveguide 104 may be formed as a single unitary body. In either configuration, the ultrasonic transmission waveguide 104 amplifies the mechanical vibrations transmitted to the ultrasonic blade 150 as is well known in the art. The ultrasonic blade 150 is adapted to couple to the ultrasonic surgical instrument 100, which may be coupled to above-described ultrasonic system 10. In one embodiment, the ultrasonic blade 150 and the ultrasonic transmission waveguide 104 may be formed as a single unitary body.

The ultrasonic blade 150 comprises the substantially straight planar treatment region 158 to effect tissue. The treatment region 158 comprises the generally flat planar top surface 154 and the smooth substantially arcuate bottom surface 156. The bottom surface 156 comprises a smooth atraumatic surface 162 that is substantially arcuate about axis 131 at a distal end 134 of the treatment region 158 for bone contact and atraumatic use along the bone region. The distal end 134 of the treatment region 158 also comprises a substantially flat tip with a distal cutting edge 166. The atraumatic surface 162 is configured to prevent the distal cutting edge 166 from cutting into bone tissue. The atraumatic surface 162 extends from the bottom surface 156 to the top surface 154 and is intended to contact and slidingly engage the bone as the cutting edge 166 removes muscle tissue from the bone without cutting into bone tissue. A cutting edge 168 is positioned laterally along one side of the treatment region 158. The blade 150 and the distal cutting edge 166 define a broad top surface 154 for effecting tissue. The broad top surface 154 of the blade 150 has a width "W" that is substantially greater than a thickness "T". In one embodiment, the cutting edge 168 extends from the proximal end 132 to the distal end 134 of the treatment region 158. The blade 150 also comprises a dull, smooth, or curved lateral coagulating edge 164 positioned laterally along the side of the treatment region 158 opposite the lateral cutting edge 168. In one embodiment, the coagulating edge 164 extends from the proximal end 132 to the distal end 134 of the treatment region 158. The coagulating edge 164 may be used for different tissue effects other than coagulation, for example. In one example, the flat tip distal cutting edge 166 or the lateral cutting edge 168 of the ultrasonic blade 150 is suitable to remove muscle tissue from bone while the atraumatic surface 162 glides against the bone. The clinician may select either one of the cutting edges 166, 168 or the atraumatic surface 162 for different tissue effects. The ultrasonic blade 150 may be fabricated from a material suitable for transmission of ultrasonic energy as previously described with respect to the ultrasonic blade 120.

Figure 12:
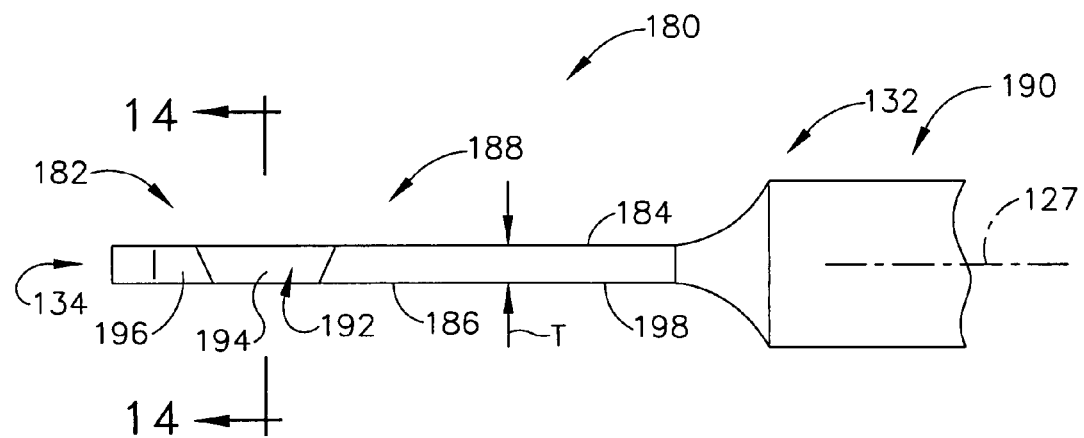
FIGS. 12-15 illustrate one embodiment of an ultrasonic blade, where.
Figure 13:
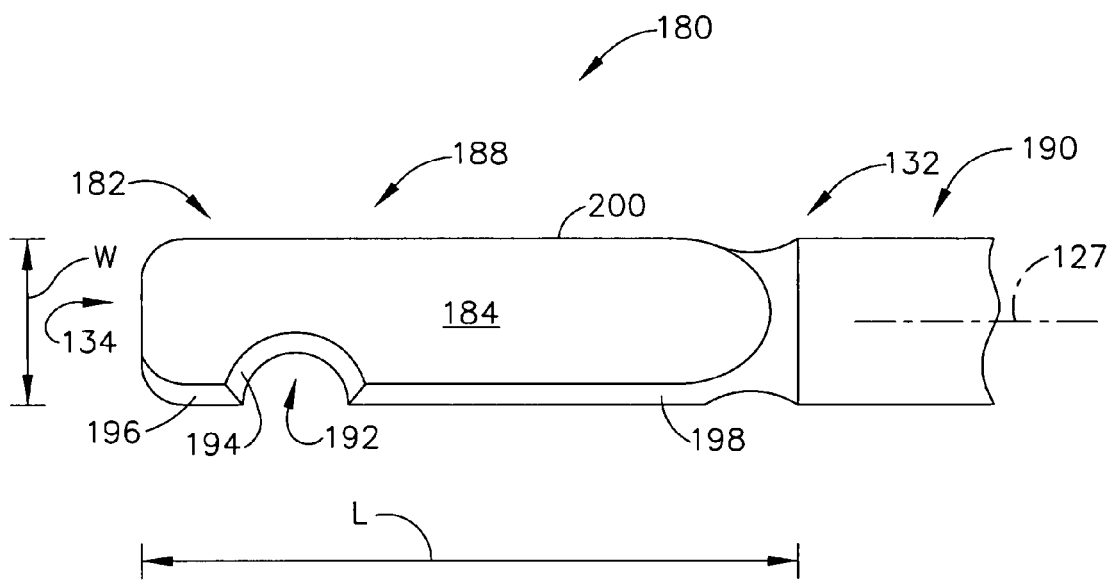
Figure 14:
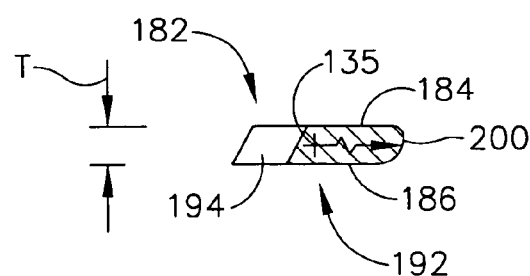
Figure 15:
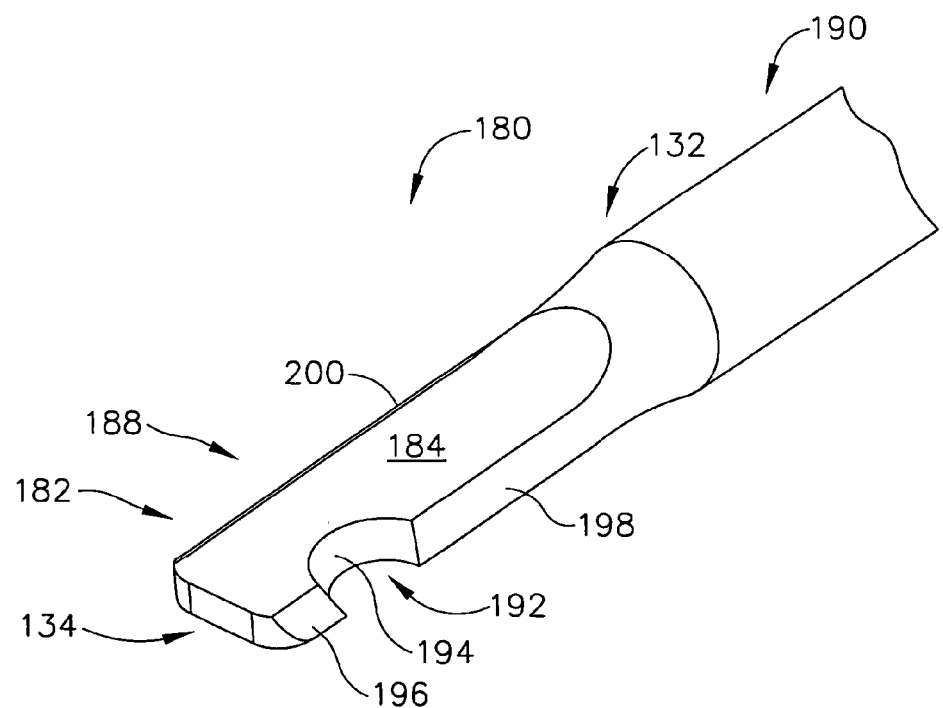

FIGS. 12-15 illustrate one embodiment of an ultrasonic blade 180. The ultrasonic blade 180 is generally well-suited for cutting, coagulating, and reshaping tissue. In one embodiment the ultrasonic blade 180 may be configured as an ultrasonic surgical elevator blade generally well-suited to separate muscle tissue from bone. Nevertheless, the ultrasonic blade 180 may be employed in various other therapeutic procedures. FIG. 12 is a side view of the ultrasonic blade 180. FIG. 13 is a top view of the ultrasonic blade 180. FIG. 14 is a cross-sectional view of the ultrasonic blade 180 taken along line 14-14 in FIG. 12. FIG. 15 is a top perspective view of the ultrasonic blade 180.

In the embodiment illustrated in FIGS. 12-15, the ultrasonic blade 180 comprises a blade body 182 having a generally flat planar top surface 184 and a generally flat planar bottom surface 186. The top and bottom surfaces 184, 186 are substantially parallel and extend along the longitudinal central axis 127. The blade body 182 may comprise a substantially elongated treatment region, generally designated as 188, and a neck or transition portion 190 that protrudes from a proximal end 132 of the treatment region 188. The neck portion 190 may be attached to the ultrasonic transmission waveguide 104 by a stud, weld, glue, quick connect, or other known attachment methods, for example. In alternative embodiments, the ultrasonic blade 180 and the ultrasonic transmission waveguide 104 may be formed as a single unitary body. In either configuration, the ultrasonic transmission waveguide 104 amplifies the mechanical vibrations transmitted to the ultrasonic blade 180 as is well known in the art. Accordingly, the ultrasonic blade 180 is adapted to couple to the ultrasonic surgical instrument 100, which may be employed with the above-described ultrasonic surgical instruments 100, which may be employed in the above-described ultrasonic system 10. In one embodiment, the ultrasonic blade 180 and the ultrasonic transmission waveguide 104 may be formed as a single unitary body.

The ultrasonic blade 180 comprises the substantially flat planar treatment region 188 to effect tissue. The treatment region 188 comprises the generally flat planar top surface 184 and the generally flat planar bottom surface 186. A notch 192 (hook shaped in the illustrated embodiment) is defined at the distal end 134 of the treatment region 188. The notch 192 extends inwardly into the blade body 182. The notch 192 comprises a cutting edge 194. A first straight lateral cutting edge 196 is positioned on the distal end 134 of the treatment region 188. A second straight lateral cutting edge 198 is positioned laterally along the along the side of the treatment region 188 between the notch 192 and the proximal end 132. A dull, smooth, or curved coagulating edge 200 is positioned laterally along the side of the treatment region 188 opposite the lateral cutting edge 198. The dull, smooth, or curved coagulating edge 200 is substantially arcuate about axis 135. The blade 180 and the lateral cutting edge 198 define a broad top surface 184. The broad top surface 184 of the blade 184 has a width "W" that is substantially greater than a thickness "T". In one embodiment, the curved edge 200 extends from the proximal end 132 to the distal end 134 of the treatment region 188. The coagulating edge 200 may be used different tissue effects other than coagulation, for example. In one example, the cutting edges 194, 196, 198 of the ultrasonic blade 180 may be employed to remove muscle tissue from bone while the coagulating edge 200 may be used for coagulation. The notch cutting edge 194 assists in cutting tissue. For example, the notch cutting edge 194 allows for faster tissue cutting in avascular tissue or may aid in entering joint capsules. The ultrasonic blade 180 may be fabricated from a material suitable for transmission of ultrasonic energy as previously described with respect to the ultrasonic blade 120.

Figure 16:
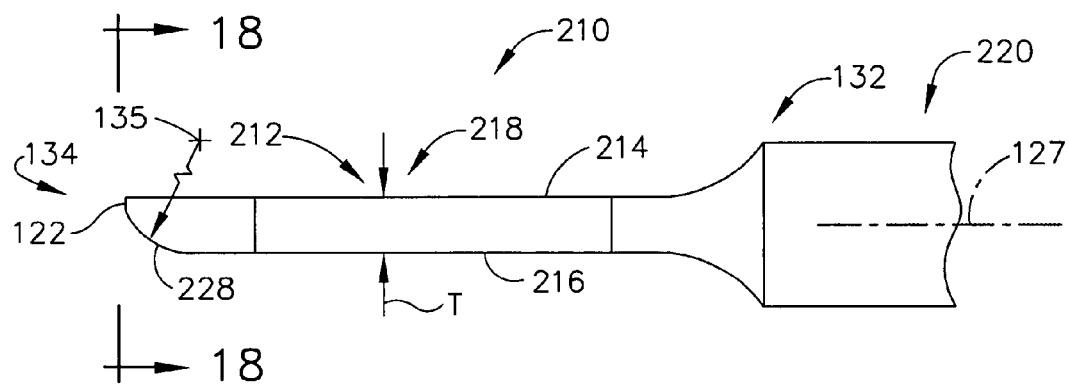
FIGS. 16-19 illustrate one embodiment of an ultrasonic blade, where.
Figure 17:
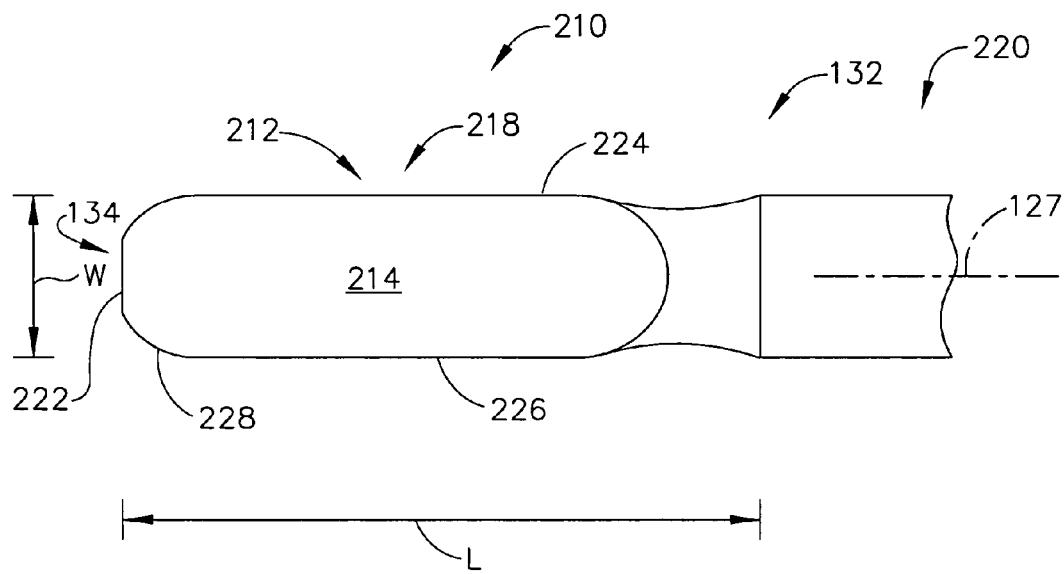
Figure 18:
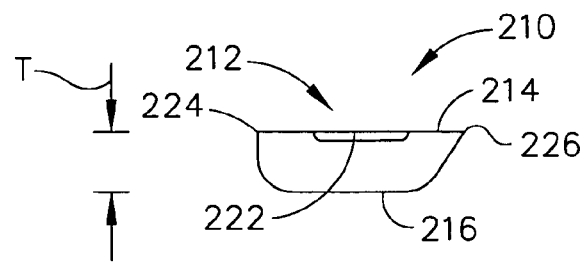
Figure 19:
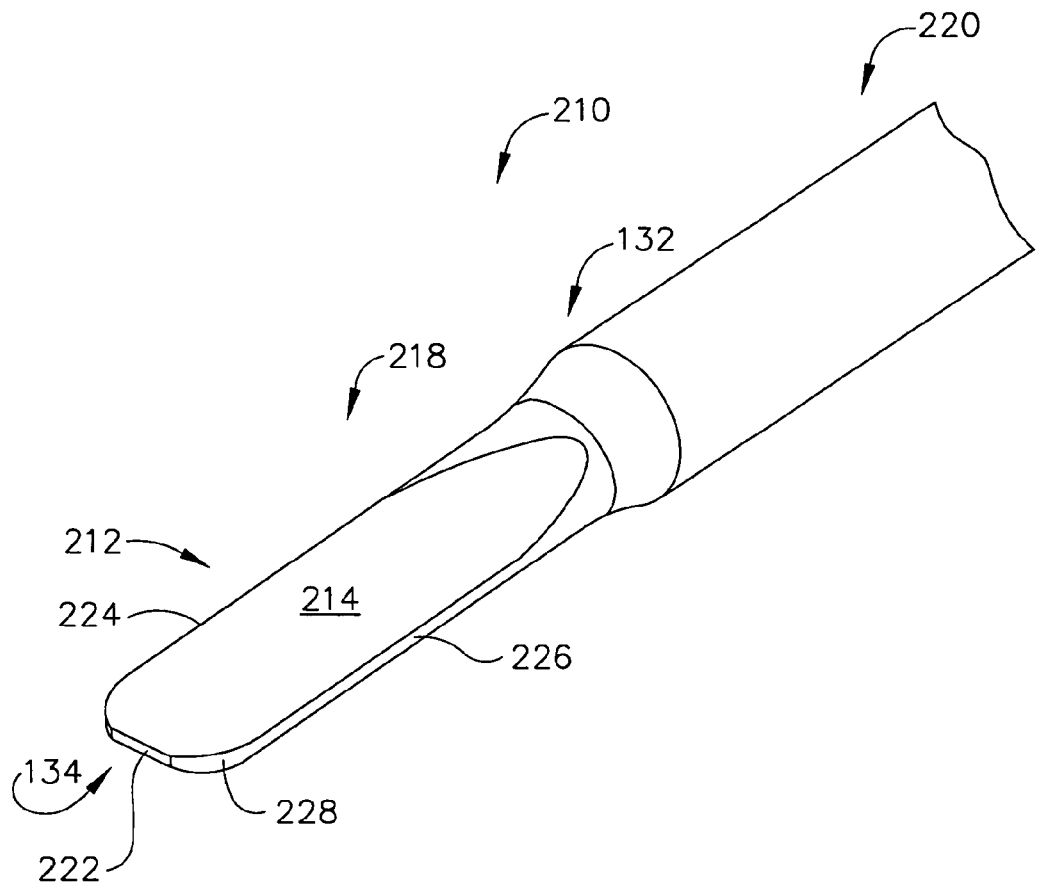

FIGS. 16-19 illustrate one embodiment of an ultrasonic blade 210. The ultrasonic blade 210 is generally well-suited for cutting, coagulating, and reshaping tissue. In one embodiment the ultrasonic blade 210 may be configured as an ultrasonic surgical elevator blade generally well-suited to separate muscle tissue from bone. Nevertheless, the ultrasonic blade 210 may be employed in various other therapeutic procedures. FIG. 16 is a side view of the ultrasonic blade 210. FIG. 17 is a top view of the ultrasonic blade 210. FIG. 18 is an end-sectional view of the ultrasonic blade 210 taken along line 18-18 in FIG. 16. FIG. 19 is a top perspective view of the ultrasonic blade 210.

In the embodiment illustrated in FIGS. 16-19, the ultrasonic blade 210 comprises a blade body 212 having a generally flat planar top surface 214 and a generally flat planar bottom surface 216. The top and bottom surfaces 212, 214 are substantially parallel and extend along the longitudinal central axis 127. The blade body 212 may comprise a substantially elongated treatment region, generally designated as 218, and a neck or transition portion 220 that protrudes from a proximal end 132 of the treatment region 218. The neck portion 220 may be attached to the ultrasonic transmission waveguide 104 by a stud, weld, glue, quick connect, or other known attachment methods, for example. In alternative embodiments, the ultrasonic blade 210 and the waveguide 104 may be formed as a single unitary body. In either configuration, the ultrasonic transmission waveguide 104 amplifies the mechanical vibrations transmitted to the ultrasonic blade 210 as is well known in the art. Accordingly, the ultrasonic blade 210 is adapted to couple to the ultrasonic transmission waveguide 104 of the surgical instrument 100, which may be employed with the above-described ultrasonic system 10. In one embodiment, the ultrasonic blade 210 and the ultrasonic transmission waveguide 104 may be formed as a single unitary body.

The ultrasonic blade 210 comprises the substantially flat planar treatment region 218 to effect tissue. The treatment region 218 comprises the generally flat planar top surface 214 and the generally flat planar bottom surface 216. A first atraumatic flat edge 222 may be positioned on the tip at the distal end 134 of the ultrasonic blade 210 for bone contact and atraumatic use along the bone region as well as to characterize the blade 210. The blade 210 and the distal atraumatic edge 222 define a broad top surface 214 for effecting tissue. The top surface 214 of the blade 210 has a width "W" that is substantially greater than a thickness "T" of the blade 210. The flat atraumatic edge 222 at the tip of the distal end 134 of the ultrasonic blade 210 may be normal to the longitudinal central axis 127 of the ultrasonic blade 210 and may be employed for benchmarking measurements of the displacement of the distal end 134, for example. This may be employed to make measurements and to characterize the ultrasonic blade 210. A smooth atraumatic surface 228 that is substantially arcuate about axis 135 may be provided at the distal end 134 for bone contact and atraumatic use along the bone region. Cutting edges 224, 226 may be disposed laterally along both sides of the treatment region 218. The ultrasonic blade 210 may be fabricated from a material suitable for transmission of ultrasonic energy as previously described with respect to the ultrasonic blade 120.

Figure 20:
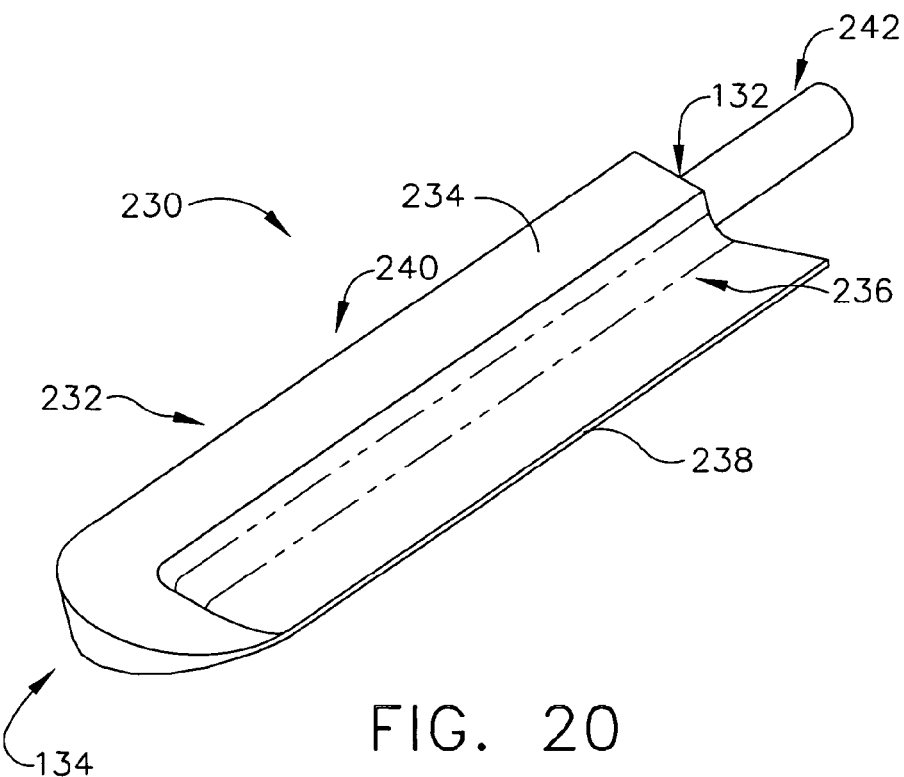
FIG. 20 is a top perspective view of one embodiment of an ultrasonic blade.

FIG. 20 is a top perspective view of one embodiment of an ultrasonic blade 230. The ultrasonic blade 230 is generally well-suited for cutting, coagulating, and reshaping tissue. In one embodiment the ultrasonic blade 230 may be configured as an ultrasonic surgical elevator blade generally well-suited to separate muscle tissue from bone. Nevertheless, the ultrasonic blade 230 may be employed in various other therapeutic procedures. The ultrasonic blade 230 has a blade body 232 that has a generally flat planar tapered top surface portion 234, a generally flat planar bottom surface 238 (FIG. 21), and an offset edge portion 236 with a cutting edge 239 well-suited for dissecting tissue against bone. The ultrasonic blade 230 may be fabricated from a material suitable for transmission of ultrasonic energy as previously described with respect to the ultrasonic blade 120. The blade body 232 may comprise a substantially elongated treatment region, generally designated as 240, and a neck or transition portion 242 that protrudes from a proximal end 132 of the treatment region 240. The neck portion 242 may be attached to the ultrasonic transmission waveguide 104 by a stud, weld, glue, quick connect, or other known attachment methods, for example. In alternative embodiments, the ultrasonic blade 230 and the waveguide 104 may be formed as a single unitary body. In either configuration, the ultrasonic transmission waveguide 104 amplifies the mechanical vibrations transmitted to the ultrasonic blade 230 as is well known in the art. Accordingly, the ultrasonic blade 230 is adapted to couple to the ultrasonic surgical instrument 100, which may be employed with the above-described ultrasonic system 10.

Figure 21:
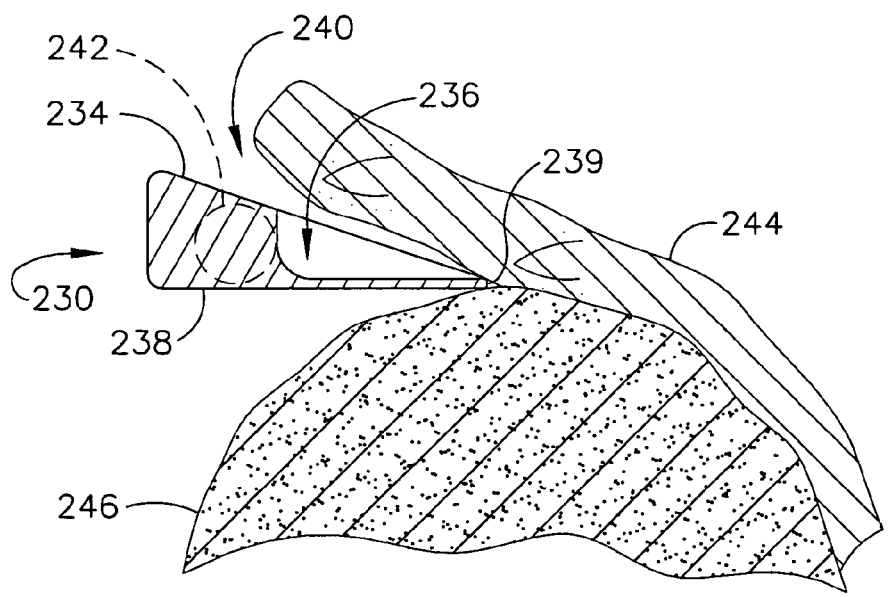
FIG. 21 illustrates a use of one embodiment of the ultrasonic blade shown in FIG. 20.

FIG. 21 illustrates a use of one embodiment of the ultrasonic blade 230 shown in FIG. 20. The ultrasonic blade 230 comprises the generally planar treatment region 240 with a generally flat planar top surface 234, a generally flat planar bottom surface 238, and an offset edge portion 236 with a cutting edge 239. The cutting edge 239 is suitable to dissect muscle tissue 244 from a bone 246.

The ultrasonic blades 120, 150, 180, 210, 230 described above each have a length "L" that is substantially equal to an integral multiple of one-half system wavelengths ($\lambda/2$). The distal end 134 of the ultrasonic blades 120, 150, 180, 210, 230 may be disposed near an antinode in order to provide the maximum longitudinal excursion of the distal end 134. When the transducer assembly is energized, the distal end 134 of the ultrasonic blade 120, 150, 180, 210, 230 may be configured to move in the range of, for example, approximately 10 to 500 microns peak-to-peak, and preferably in the range of about 30 to 150 microns at a predetermined vibrational frequency range. As previously discussed, a suitable vibrational frequency range may be about 20 Hz to 120 kHz and a well-suited vibrational frequency range may be about 30-70 kHz and one example operational vibrational frequency may be approximately 55.5 kHz.

Other embodiments may comprise multiple end effectors 50 attached distally to a common ultrasonic transmission waveguide 104. The end effectors 50 may provide a variety of tissue effects that are similar to those discussed above with respect to the ultrasonic blades 120, 150, 180, 210, 230. As discussed above, the ultrasonic blades 120, 150, 180, 210, 230 may be separable (and of differing composition) from the waveguide 104, and coupled by, for example, a stud, weld, glue, quick connect, or other known methods. A quick connect coupling may provide lower cost and ease of use of multiple ultrasonic blades 120, 150, 180, 210, 230 in one procedure.

As described above, an end effector or blade of an ultrasonic surgical instrument can be vibrated along a longitudinal axis to treat tissue, for example. In various circumstances, such instruments can be preferably configured such that they do not vibrate in any other direction, such as axes which are transverse to the longitudinal axis, for example. Such transverse vibration may make the surgical instrument inefficient and may require additional power to operate the surgical instrument, for example. In at least one circumstance, such transverse vibration may be created and/or amplified by an imbalanced asymmetrical configuration of the blade. In various embodiments of the present invention, an end effector or blade of an ultrasonic surgical instrument can be configured such that such transverse vibration is reduced or eliminated. For example, in at least one embodiment, the blade can include an asymmetrical configuration which can be balanced with respect to at least one axis which is transverse to the longitudinal vibrational axis of the surgical instrument, as described in greater detail below.

In various embodiments, referring to FIGS. 56-59, an ultrasonic surgical instrument blade, such as blade 680, for example, can include blade body 682 having a generally flat top surface, or side, 684 and a generally flat bottom surface, or side, 686. Although surfaces, or sides, 684 and 686 can be generally flat or planar, they can comprise any suitable configuration including curved and/or curvilinear configurations, for example. The top and bottom surfaces 684, 686 can be substantially parallel and can extend along the longitudinal or central axis 127. The blade body 682 may comprise a substantially elongated treatment region, generally designated as 688, and a neck or transition portion 690 that protrudes from a proximal end 632 of the treatment region 688. The neck portion 690 may be attached to the ultrasonic transmission waveguide 104 (FIG. 1) by a stud, weld, glue, quick connect, or other known attachment methods, for example. In alternative embodiments, the ultrasonic blade 680 and the ultrasonic transmission waveguide 104 may be formed as a single unitary body. In either configuration, the ultrasonic transmission waveguide 104 can amplify the mechanical vibrations transmitted to the ultrasonic blade 680 as is well known in the art.

Figure 57:
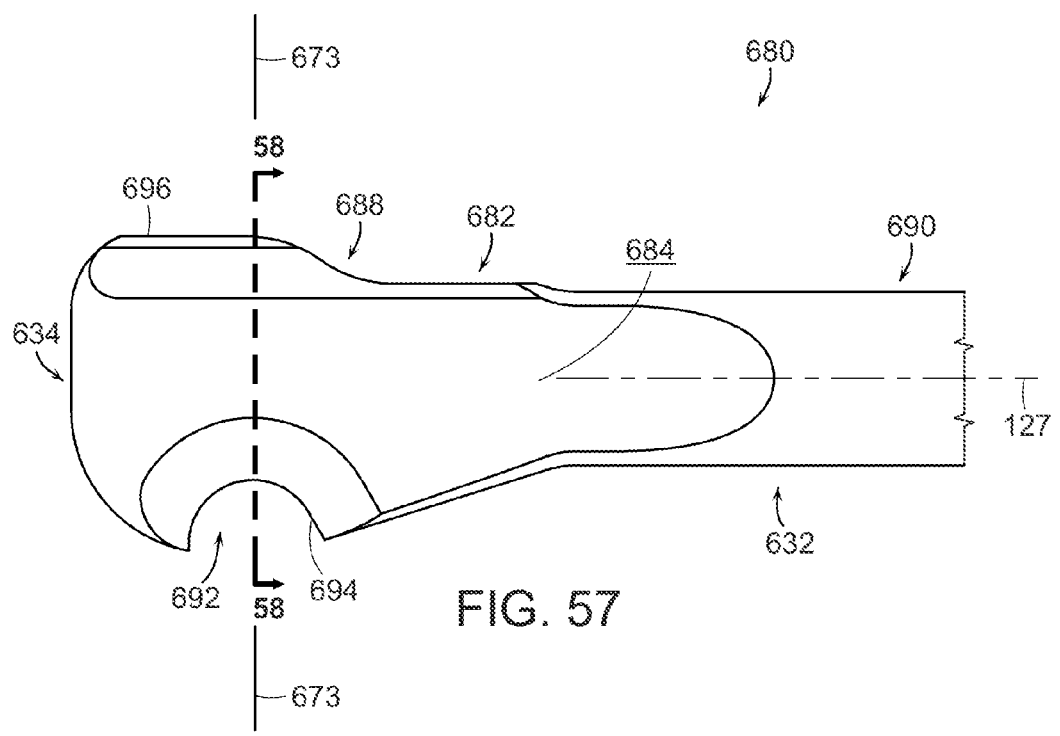
Figure 58:
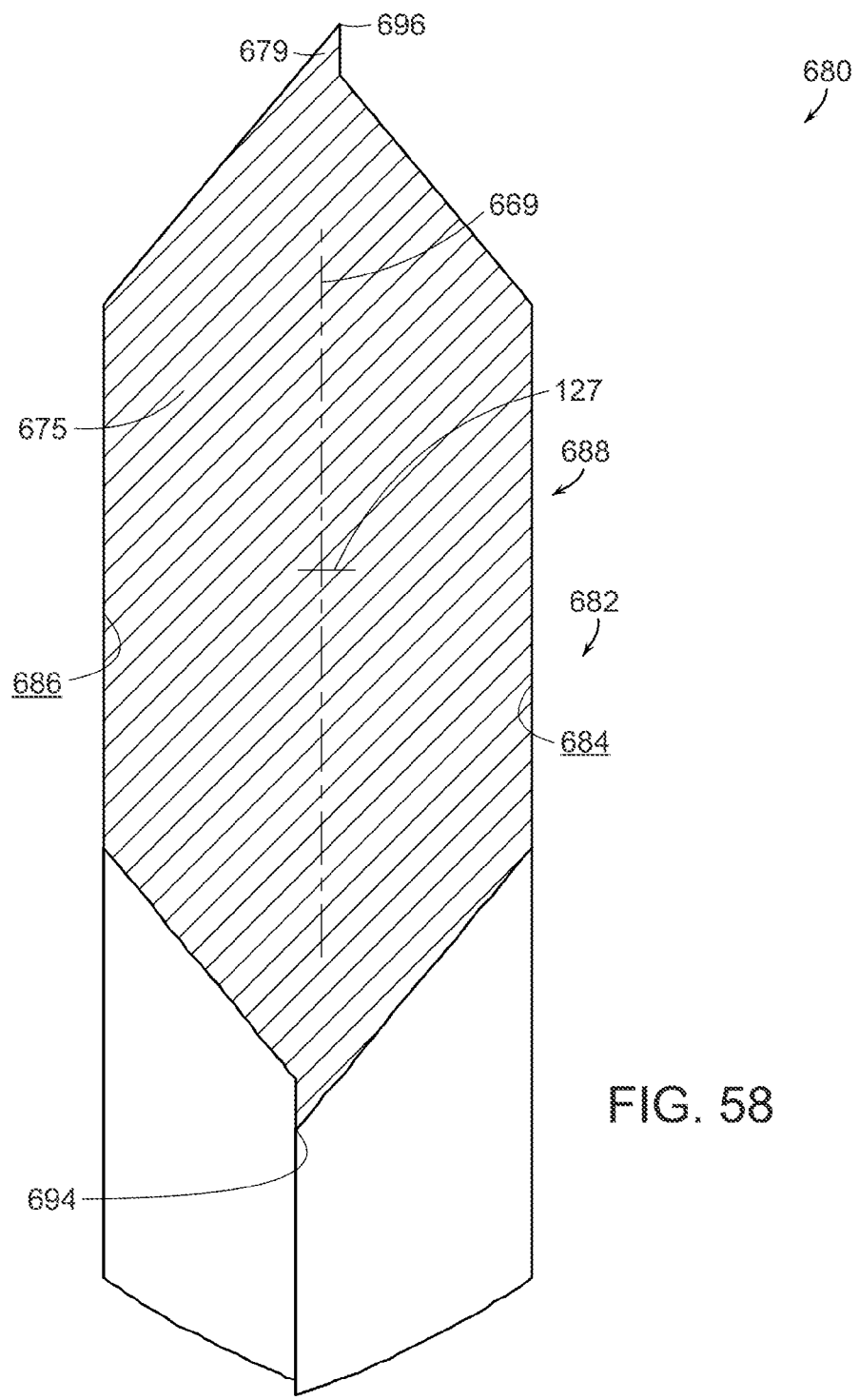
Figure 59:
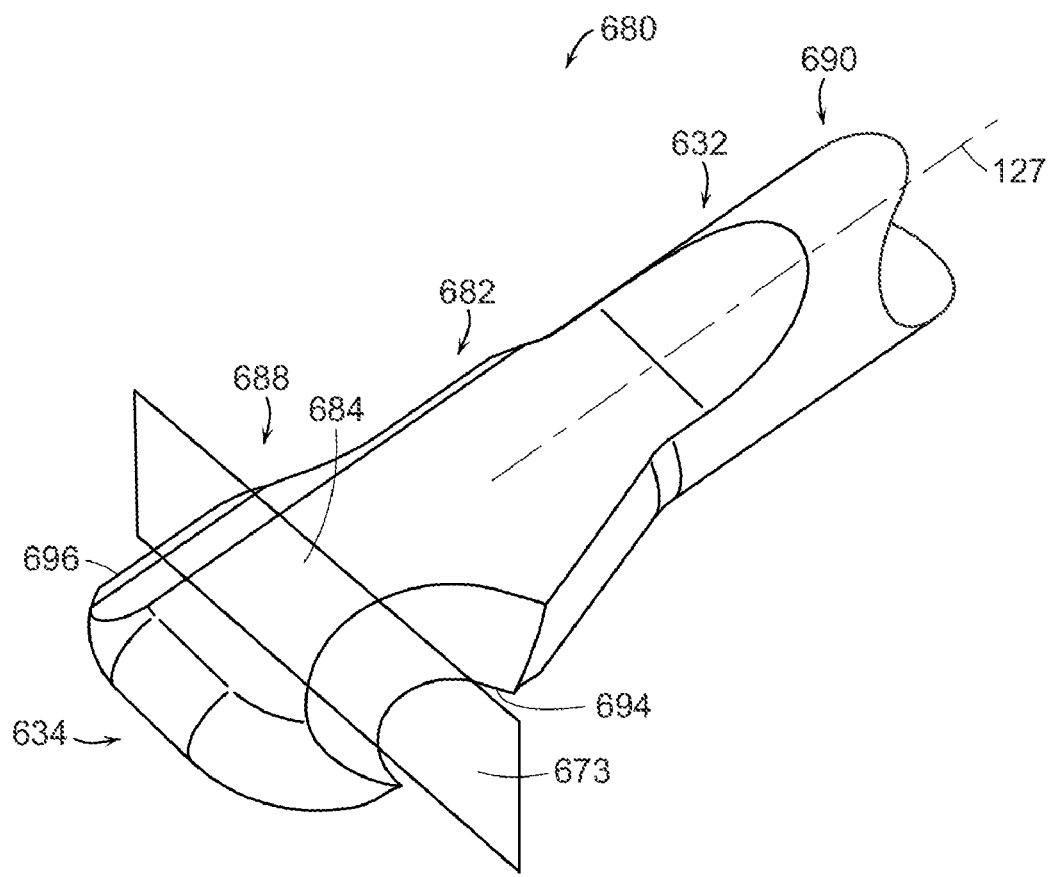

In various embodiments, blade 680 can include a notch 692 (hook shaped in the illustrated embodiment) which is defined at the distal end 634 of the treatment region 688. The notch 692 can extend inwardly into the blade body 682, as illustrated in FIGS. 57 and 59, wherein the notch 692 can comprise a cutting edge 694 configured to incise tissue, for example. In various embodiments, referring to FIG. 58, the blade 680 can further include cutting edge 696 which can also be configured to incise tissue, for example. In at least one embodiment, the cross-section of blade 680, again referring to FIG. 58, can be configured such that blade 680 is balanced, or at least substantially balanced, with respect to axis 669. In various embodiments, the cross-section can be defined by a plane, such as plane 673, for example, wherein plane 673 can be perpendicular to longitudinal axis 127 and wherein axis 669 can lie within the plane 673. In at least one embodiment, the cross-section of blade 680 can include a body, or central, portion 675 and a cutting, or step, portion 679, extending from central portion 675. In various embodiments, axis 669 may be referred to as a centerline of the blade, or a portion of the blade, although such use is not intended to communicate that the blade, or a portion of the blade, is necessarily symmetrical. Often, such a reference can be used to refer to an axis, or datum, which is utilized to determine or measure whether a symmetrical and/or asymmetrical blade, or a portion of a blade, is balanced with respect thereto.

Figure 60:
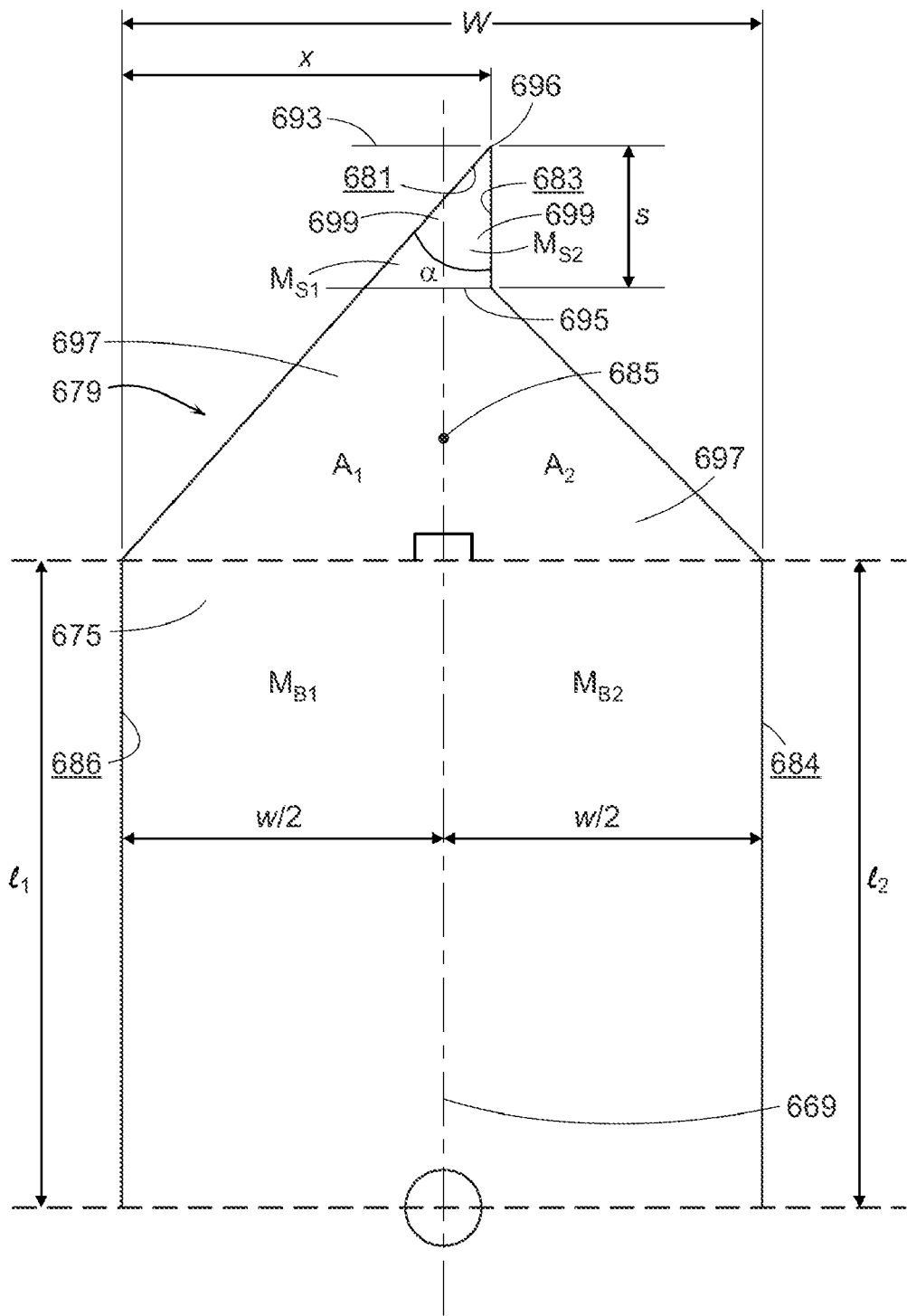
FIG. 60 is a schematic of parameters of a cross-section of a blade which can be used to balance the blade.

In various embodiments, referring to the cross-section of blade 680 illustrated in FIG. 60, the sides of central portion 675 can be defined by surfaces 684 and 686, for example, wherein surfaces 684 and 686 can define a width (w) therebetween. Although the width of central portion 675 is substantially constant in the illustrated exemplary embodiment, the width of central portion 675 can have any suitable configuration, including configurations which comprise identical, or at least substantially identical, portions on the opposite sides of transverse axis 669, for example. In at least one such embodiment, central portion 675 can include a first mass $M_{B1}$ positioned on a first side of transverse axis 669 and a second mass $M_{B2}$ positioned on a second side of said transverse axis, wherein $M_{B1}$ can be equal, or at least substantially equal, to $M_{B2}$. In various embodiments, again referring to FIG. 60, $M_{B1}$ can comprise the area defined by $l_1$ and w/2 and, similarly, $M_{B2}$ can comprise the area defined by $l_2$ and w/2. In at least one embodiment, $l_1$ can equal, or at least substantially equal, $l_2$. In various alternative embodiments, however, $M_{B1}$ may not be equal to $M_{B2}$. In at least one such embodiment, $l_1$ may not equal $l_2$. In various embodiments, though, the mass of blade 680 may be balanced in another manner as described in greater detail below.

In various embodiments, referring to FIG. 60, step portion 679 of the cross-section can comprise first surface 681 and second surface 683, wherein cutting edge 696 can be positioned intermediate first surface 681 and second surface 683. In at least one embodiment, step portion 679 can include, similar to the above, a first mass $M_{S1}$, defined by $A_1$, positioned on the first side of axis 669 and a second mass $M_{S2}$, defined by $A_2$, positioned on the opposite, or second, side of axis 669, wherein $M_{S1}$ can be equal, or at least substantially equal, to $M_{S2}$. In at least one such embodiment, step portion 679 can include a center of gravity 685, wherein center of gravity 685 can be positioned along transverse axis 669. Although various embodiments having a symmetrical step portion 679 are possible, step portion 679 can include an asymmetric configuration with respect to transverse axis 669. In at least one such embodiment, cutting edge 696 may not lie along, or be co-planar with, axis 669 wherein, as a result, blade 680 can include a cutting edge which is positioned closer to one of sides 684 and 686 without creating a mass imbalance with respect to axis 669. In at least one embodiment, referring to FIG. 60, cutting edge 696 can be positioned a distance x with respect to second side 686, for example, such that blade 680 is balanced as described in greater detail below. Owing to the closer proximity of the cutting edge with respect to one side of the blade, the cutting edge may be more visible to the surgeon thereby facilitating the proper use of the surgical instrument.

In various embodiments, further to the above, $M_{S1}$ may not be equal to $M_{S2}$. In at least one such embodiment, though, the masses of central portion 675 and step portion 679, for example, can be arranged such that the mass of blade 680 is still balanced with respect to transverse axis 669, for example. More particularly, $M_{S1}$, $M_{S2}$, $M_{B1}$, and $M_{B2}$ can be selected such that $M_{B1}+M_{S1}$ is equal, or at least substantially equal, to $M_{B2}+M_{S2}$. In such embodiments, as a result, the total mass of blade 680 on the first side of axis 669 can be equal, or at least substantially equal, to the total mass of blade 680 on the second side of axis 669. Furthermore, in various embodiments, the mass of blade 680 can be arranged such that the moment of force and the moment of inertia of masses $M_{S1}$, $M_{S2}$, $M_{B1}$, and $M_{B2}$ are balanced as well. Generally, the moment of force of a mass is proportional to the product of the mass and the distance between the center of gravity of the mass and a datum, or axis. Also, generally, the moment of inertia of a mass is proportional to the product of the mass and the square of the distance between the center of gravity of the mass and a datum, or axis. Referring to the illustrated embodiment of FIG. 60, masses $M_{S1}$, $M_{S2}$, $M_{B1}$, and $M_{B2}$ can be positioned so as to balance, or at least substantially balance, the moment of force and the moment of inertia of blade 680 with respect to transverse axis 669, for example.

Figure 60A:
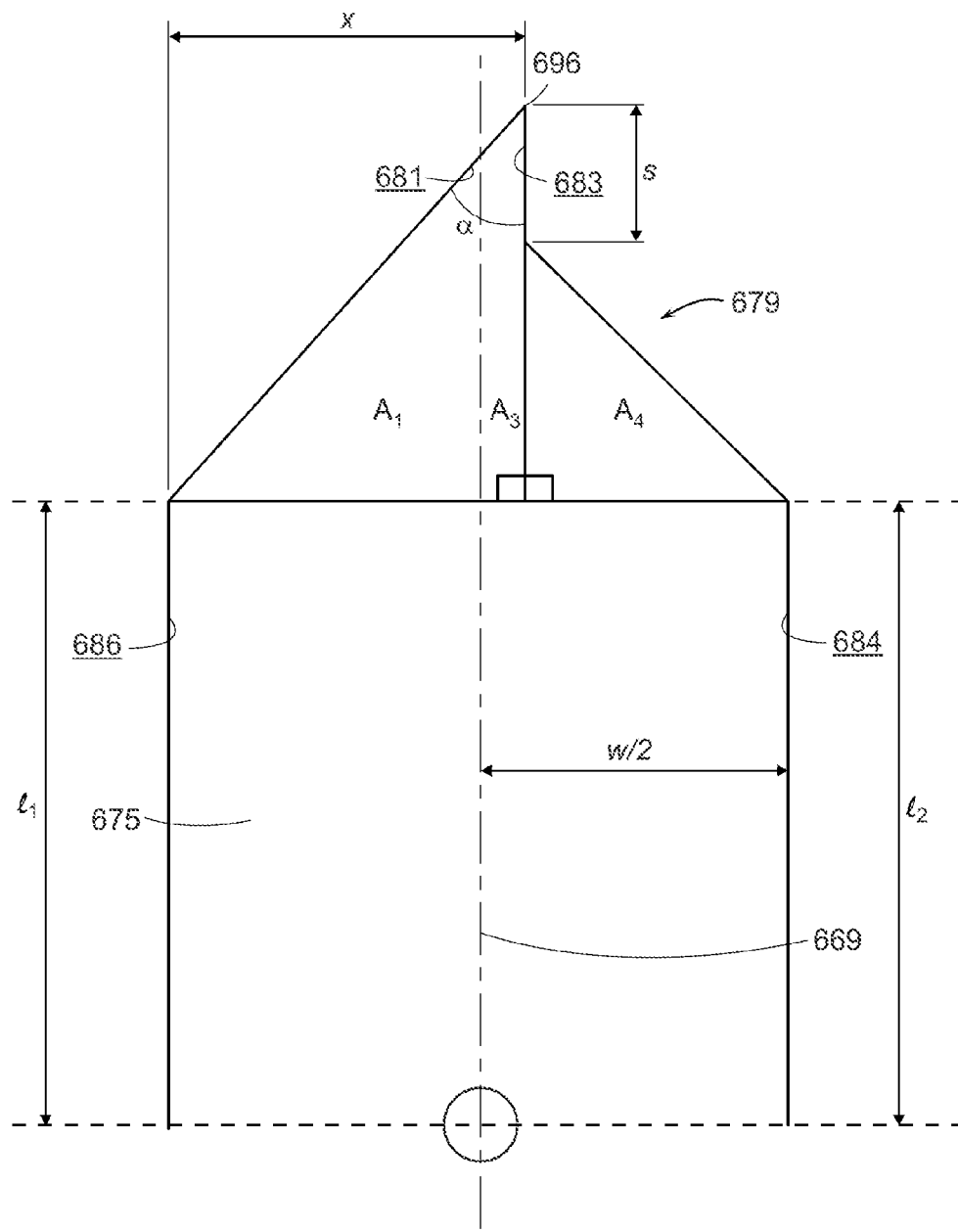
FIG. 60A is an additional schematic of the cross-section of FIG. 60

In various embodiments, again referring to FIG. 60, step portion 679, as described above, can include first and second surfaces and a cutting edge 696 positioned therebetween. In at least one embodiment, step portion 679 can further include an edge height, s, which can define the distance between cutting edge 696 and first portion 697 of step portion 679. More particularly, in at least one embodiment, step portion 679 can include first portion 697 and cutting portion 699 which are separated by datum 695, wherein edge height s can define the distance between the top of first portion 697, i.e., cutting edge 696, and datum 695. Stated another way, referring to FIG. 60A, edge height s can be defined as the distance between the top of a right triangle defined by area $A_4$ and the top of a right triangle defined by the combined areas of $A_1$ and $A_3$. In at least one embodiment, further to the above, $A_1$ can equal $A_2$, and $A_2$ can equal $A_3+A_4$. In various embodiments where second surface 683 is parallel to axis 669, the edge height s can equal the length of second surface 683. In various other embodiments where second surface 683 is not parallel to axis 669, the edge height s can equal the length of the projection of second surface 683 onto axis 669. In various embodiments, cutting edge 696 can lie in a first plane 693, datum 695 can lie in a second plane which is parallel to the first plane, and wherein the step height s can define the distance between the first and second planes.

In various embodiments, first surface 681 and second surface 683 can be arranged such that an angle α, or edge angle, is defined therebetween wherein the edge angle can be any suitable angle such as approximately 35 degrees or approximately 65 degrees, for example. During various experimental uses of such surgical blades, it was observed that surgical blades having smaller edge angles, i.e., angles closer to zero degrees, transected tissue faster than surgical blades having larger edge angles, i.e., angles closer to 90 degrees. It was also observed, though, that such blades were to able to seal, or produce hemostasis within, the edges of the tissue as the tissue was being transected regardless of the edge angle selected. Such a result was deemed to be surprising and, advantageously, it is believed that the edge angle of the blades disclosed herein can be selected to facilitate a desired cutting rate without affecting the hemostasis of the tissue. Furthermore, it was also determined by the experimental uses of such surgical blades that a relationship for producing hemostasis within porcine tissue can comprise:

$$1.26-0.0102*a-1.14*h+8.14w$$

wherein a represents the longitudinal amplitude of the blade, wherein w represents the width of the blade, similar to the above, and wherein h represents the height of the blade. In various embodiments, this relationship for producing hemostasis can be equated to zero, values for two of variables a, h, and w can be selected or input into the relationship, and the relationship can then be utilized to determine a value for the third variable. In at least one circumstance, this relationship was used to determine a suitable range of widths for the blade, w, which can be between approximately 0.040" and approximately 0.070", depending on the level of hemostasis required from a particular blade. A width of approximately 0.060" was selected for one actual example.

In at least one embodiment, second surface 683 of step portion 679 can be parallel, or at least substantially parallel, to first side 684 and/or second side 686 of central portion 675. In various embodiments, first surface 681 can lie within a plane which is transverse to second surface 683 and first side 684, for example. Although portions of the exemplary embodiment of step portion 679 in FIG. 60 are illustrated as right triangles having straight sides, step portion 679 can include any suitable configuration which is balanced, or at least substantially balanced, with respect to transverse axis 669, for example. In at least one embodiment, such balancing can be achieved by positioning the center of gravity of the step portion along the centerline of the blade. In various embodiments, a blade, such as blade 680, for example, can be balanced such that the relationship of:

$$\frac{x^2}{2*\tan\alpha} + \frac{(w-x)}{2}\left(\frac{x}{\tan\alpha} - s\right) - \left(\frac{w}{2}\right)^2 \frac{1}{\tan\alpha} \text{ or, correspondingly:} \quad (1)$$

$$\frac{x^2}{2}*\tan^{-1}\alpha + \frac{(w-x)}{2}(x*\tan^{-1}\alpha - s) - \left(\frac{w}{2}\right)^2 \tan^{-1}\alpha$$

is equal to, or at least substantially equal to, zero, wherein w is the width of the body portion of the blade, such as central portion 675, for example, wherein α is the edge angle defined between the first and second surfaces of the step portion, such as surfaces 681 and 683, for example, wherein s is the edge height of the step portion which can be defined as outlined above, and wherein x is the distance between a side of the body portion, such as second side 686, and the cutting edge of the step portion, such as cutting edge 696, for example.

In various embodiments, suitable values for variables w, s, and α can be selected and relationship (1) can be manipulated to determine a value for variable x. In at least one such embodiment, relationship (1) is equated to zero and the selected values for variables w, s, and α are substituted into relationship (1) to determine the value for variable x. In such circumstances, variable x is dependent upon the selection of the values for w, s, and α. If a blade, such as blade 680, for example, is constructed in accordance with the selected values of w, s, and α and the determined value for x, then blade 680 will be balanced, or at least substantially balanced, with respect to transverse axis 669, for example. As outlined above, the values for variables w, s, and α can be selected for various reasons. For example, the value for variable w, i.e., the width of the body portion of the blade, can be selected such that the blade can fit through an endoscope, for example. In various embodiments, the value for variables s and α, i.e., the height and edge angle of step portion 679, can be selected to improve or optimize the manufacturability of the blade. In addition to or in lieu of the above, the values for variable w, s, and/or α can be selected to optimize the cutting performance of the blade, for example.

Although relationship (1) may be utilized to set variable x as a dependent variable, relationship (1) may be utilized to set at least one of the other above-described variables as a dependent variable. In at least one such embodiment, for example, relationship (1) can be equated to zero and selected values for variables w, s, and x can be substituted into relationship (1) to determine a value for variable α. Similarly, relationship (1) can be equated to zero and selected values for variables w, α, and x can be substituted into relationship (1) to determine a value for variable s, for example. A similar approach can be undertaken to determine a value for variable w. Further to the above, in various embodiments, an ultrasonic surgical blade can be configured such that, for any given values of s and w, the relationship of:

$$A*x^2*\tan^{-1}\alpha + B*x*\tan^{-1}\alpha + C*\tan^{-1}\alpha + D*x + E \quad (2)$$

is equal, or at least substantially equal, to zero, wherein A, B, C, D, and E are constants. In various alternative embodiments, an ultrasonic surgical blade can be configured such that, for any given values of s and α, the relationship of:

$$A*x^2 + B*x + C*x*w + D*w + E*w^2 + F \quad (3)$$

is equal, or at least substantially equal, to zero, wherein A, B, C, D, E, and F are constants. In various further embodiments, an ultrasonic surgical blade can be configured such that, for any given values of w and α, the relationship of:

$$A*x^2 + B*x + C*x*s + D*s + E \quad (4)$$

is equal, or at least substantially equal, to zero, wherein A, B, C, D, and E are constants.

In various embodiments, the above-described approaches for balancing an ultrasonic surgical blade can be utilized to balance, or at least substantially balance, various alternative surgical blades as outlined in greater detail below. In at least one embodiment, owing to the relationship between mass and kinetic energy, the energy imparted by such blades can also be balanced. More specifically, if the mass of a blade is balanced with respect to a datum or centerline of a blade, the kinetic energy produced by the blade, when it is motivated, will also be balanced with respect to the datum or centerline. In such circumstances, as a result, the surgical blade can be configured to deliver a uniform energy profile to the targeted tissue, for example. In various embodiments, a balanced, or at least substantially balanced, blade can provide a uniform, or at least substantially uniform, pressure profile to the targeted tissue. In at least one embodiment, a blade can be considered to be substantially balanced if the mass on the first side of the cross-section centerline is within approximately 10 percent of the mass on the second side of the centerline. In such embodiments, although the blade is not mass balanced, any transverse vibrations produced by the unbalanced blade may not substantially affect the performance of the blade. In at least one embodiment, a blade can be considered substantially balanced if the cutting edge, such as cutting edge 696, for example, is positioned within approximately 10 percent of the calculated distance for x, for example. Further to the above, although methods of balancing the mass of a blade with respect to one axis have been described herein, such methods can be utilized to balance the mass of a blade with respect to two or more axes.

Figure 62:
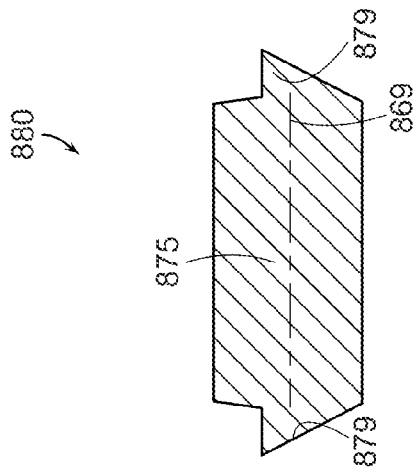
FIG. 62 is a cross-sectional view of another ultrasonic blade.
Figure 64:
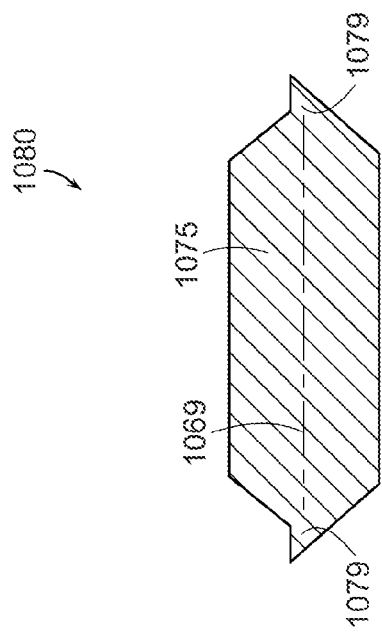
FIG. 64 is a cross-sectional view of a further ultrasonic blade.
Figure 61:
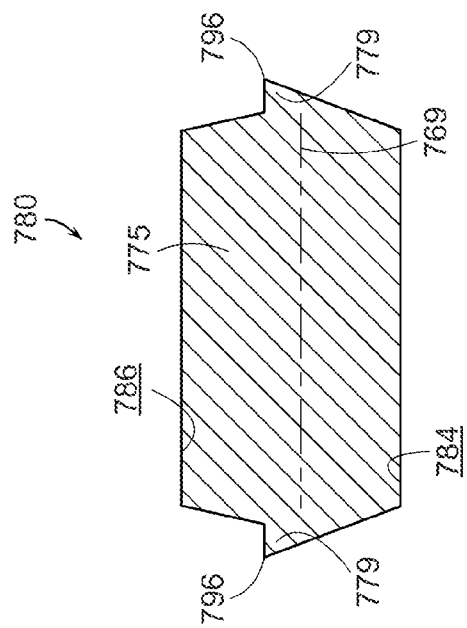
FIG. 61 is a cross-sectional view of an ultrasonic blade.
Figure 63:
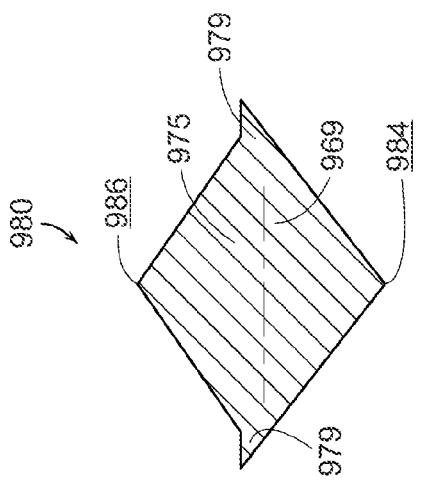
FIG. 63 is a cross-sectional view of an additional ultrasonic blade.

In at least one embodiment, referring to FIG. 61, blade 780 can include a central portion 775 having first side 784 and second side 786. Blade 780 can further include two step portions 779 which, in various embodiments, can be positioned on opposite sides of central portion 775. In such embodiments, as a result, blade 780 can comprise two cutting edges 796 which can be configured to transect tissue, for example. In various embodiments, further to the above, each step portion 779 can be balanced with respect to axis 769, wherein axis 769 can be transverse to longitudinal axis 127. In various alternative embodiments, although not illustrated, step portions 779 can be arranged such that, although each step portion 779 may be imbalanced with respect to axis 769, step portions 779 can balance, or offset, one another. In at least one additional embodiment, referring to FIG. 62, blade 880 can include central portion 875 and two step portions 879 wherein, similar to the above, portions 875 and 879 can be balanced with respect to transverse axis 869. In at least one further embodiment, referring to FIG. 63, blade 980 can include a central portion 975 having first side 984 and second side 986. Blade 980 can further include two step portions 979 wherein, similar to the above, portions 975 and 979 can be balanced with respect to transverse axis 969. In at least one more embodiment, referring to FIG. 64, blade 1080 can include central portion 1075 and two step portions 1079 wherein portions 1075 and 1079 can be balanced with respect to transverse axis 1069.

Figure 24:
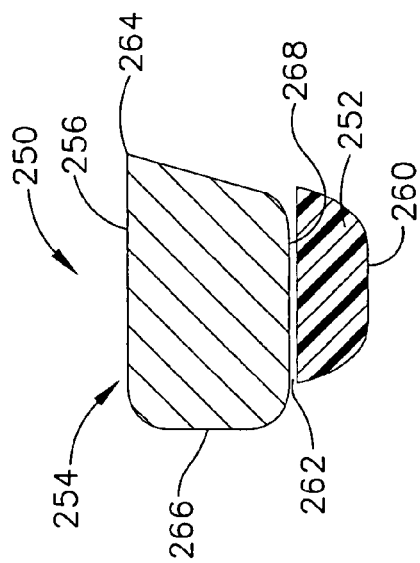
FIGS. 22-24 illustrate one embodiment of an ultrasonic blade comprising a protective sheath, where.
Figure 22:
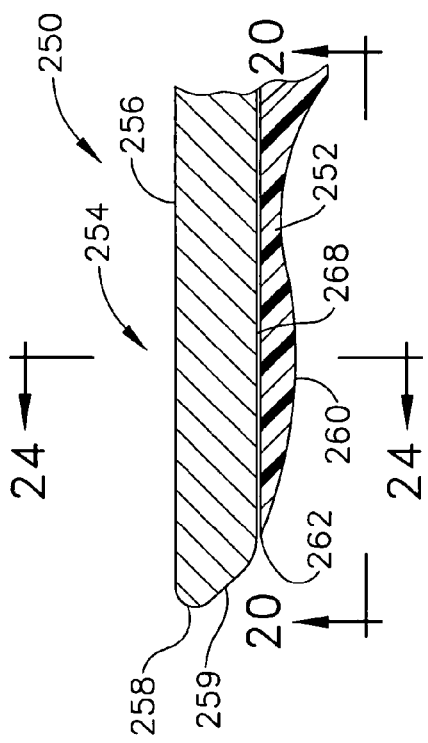
Figure 23:
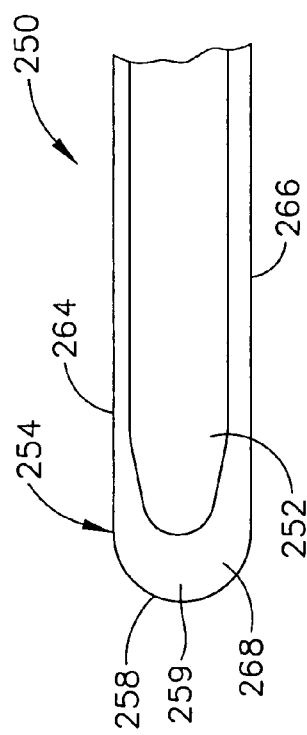

FIGS. 22-24 illustrate one embodiment of an ultrasonic blade 250 comprising a protective sheath 252. The ultrasonic blade 250 is generally well-suited for cutting, coagulating, and reshaping tissue. The protective sheath 252 is generally well suited for glidingly engaging the surface of the bone to prevent damage to the bone and the ultrasonic blade 250 while the ultrasonic blade 250 removes muscle tissue from the bone and to dissipate thermal energy generated by the ultrasonic blade 250. FIG. 22 illustrates a partial cross-sectional view of one embodiment of an ultrasonic blade 250 comprising a protective sheath 252 taken along the longitudinal axis. FIG. 23 is a bottom view of the ultrasonic blade 250 taken along line 23-23. FIG. 24 is a cross-sectional view of the ultrasonic blade 250 and the protective sheath 252. The ultrasonic blade 250 comprises a body 254 having a substantially planar top surface 256 a generally rounded cutting edge 258 and an atraumatic surface 259 for bone contact and atraumatic use along the bone region configured to prevent the cutting edge 136 from cutting into bone tissue. In one embodiment the cutting edge 258 may be configured as an ultrasonic surgical elevator blade generally well-suited to separate muscle tissue from bone. A lateral cutting edge 264 suitable for dissecting tissue is positioned on one side of the body 254 and an atraumatic edge 266 suitable to coagulate tissue may be positioned laterally along an opposite side of the body 254. The body also comprises a generally flat planar bottom surface 268 adjacent to the protective sheath 252. An air gap 262 may separate the bottom surface 268 from the protective sheath 252 for cooling purposes, for example. The protective sheath 252 comprises a substantially arcuate lateral bottom surface 260 with a flat portion in the center thereof.

Figure 25:
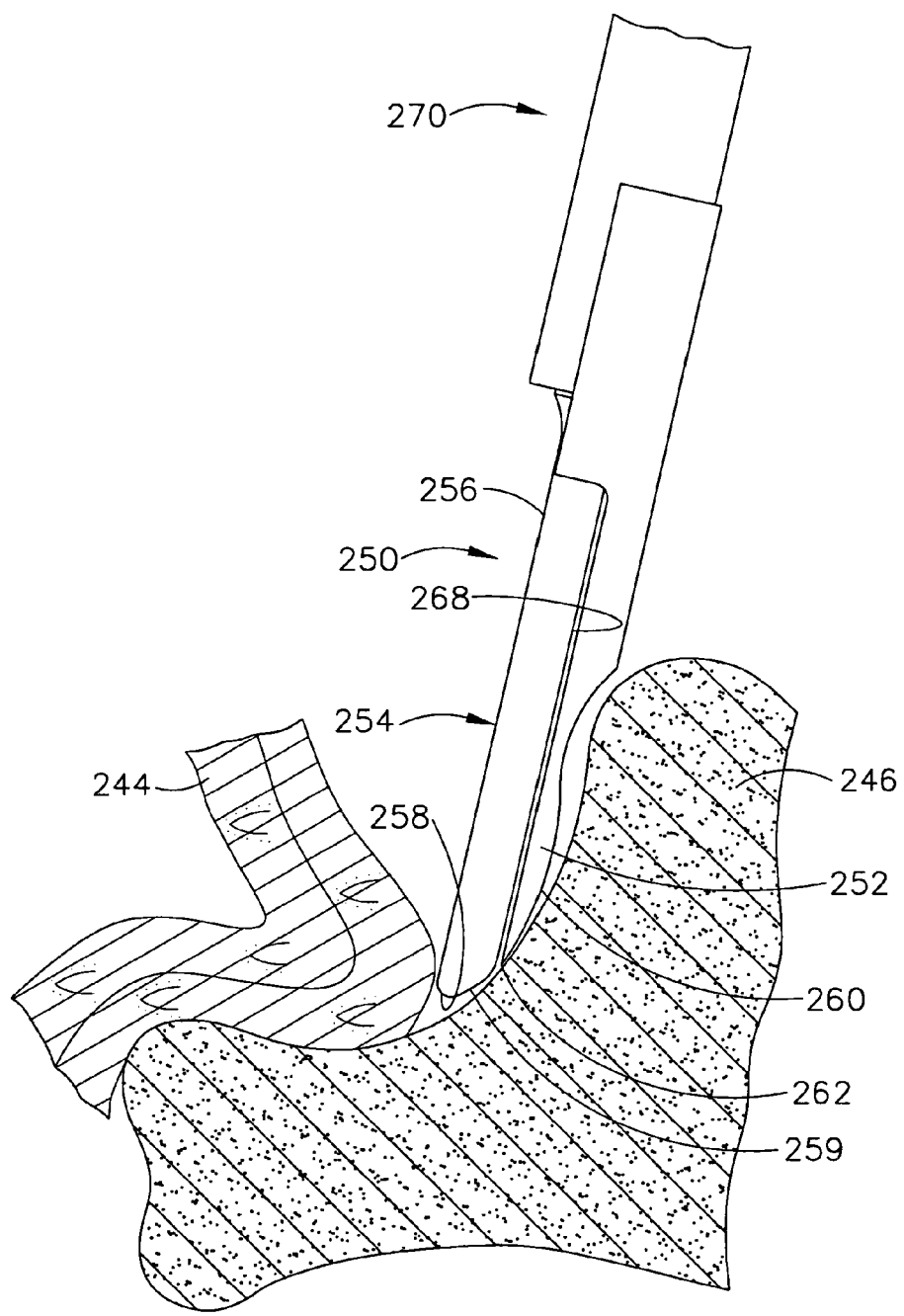
FIG. 25 illustrates a use of one embodiment of an ultrasonic surgical instrument removing muscle tissue from bone.

FIG. 25 illustrates a use of one embodiment of an ultrasonic surgical instrument 270 removing muscle tissue 244 from bone 246. The ultrasonic surgical instrument 270 comprises the ultrasonic blade 250 described above. The ultrasonic blade 250 comprises the atraumatic bone protective sheath 252. As used herein, atraumatic means designed to avoid injury. In one embodiment, the atraumatic bone protective sheath 252 extends longitudinally below the ultrasonic blade 250 to the handpiece housing of the ultrasonic surgical instrument 270 to act between the bottom surface of the ultrasonic blade 268 and the bone 246 to avoid injuring the bone 246 while coagulating, reshaping, or removing muscle tissue 244 from the bone 246 as described above. The air gap 262 provides a path for irrigation fluid to pass between the bottom surface 268 of the ultrasonic blade 250 and the protective sheath 252 to dissipate thermal energy generated by the ultrasonic blade 250 while cutting. In one embodiment, the protective sheath 252 may be rigidly and fixedly attached or mounted to the bottom surface 268 of the ultrasonic blade 250 in any suitable manner to reduce design complexity and cost. In other embodiments, the protective sheath 252 may be fixedly mounted to other substantially rigid portions of the ultrasonic surgical instrument 270. In alternative embodiments, the protective sheath 252 may be user deployable (e.g., retractable).

The protective sheath 252 reduces thermal heating effects that may result from the ultrasonic blade 250 contacting the bone 246. The process of removing the muscle tissue 244 from the bone 246 during posterior spine access may be a lengthy procedure. Accordingly, there is a concern that the high temperatures may build and cause breakage of the ultrasonic blade 250, spread of excessive lateral thermal heating, damage to the bone 246, damage to the muscle 244, and/or damage to nerve tissue. Accordingly, the bottom surface 268 of the ultrasonic blade 250 is shielded or protected by the protective sheath 252 and can rest against the surface of the bone 246 while the active portion or the cutting edge 258 of the ultrasonic blade 250 applies energy to the muscle tissue 244, resulting in good surgical technique of dissecting muscle tissue from bone (e.g., the spine). This protective sheath 252 also shields the ultrasonic blade 250 from contacting metal retractors and thus minimizes the risk of breaking the blade 250. Reducing the risk of breaking the ultrasonic blade 250 reduces instrument exchange during a surgical procedure because there is less concern for retracting instruments to avoid breaking the ultrasonic blade 250. In addition, the protective sheath 252 may enable more directed energy between the blade and a clamp arm (not shown).

The protective sheath 252 may be formed of any suitable polymeric material and may be formed on or attached to the ultrasonic blade 250 using a variety of techniques. Generally, the protective sheath 252 may be formed of any material suitable to shield the ultrasonic blade 250 from contacting bone or metal objects while cutting and minimizing the risk that of breaking the ultrasonic blade 250. In addition, the protective sheath 252 may be formed of a material and may be attached to the ultrasonic blade 250 in a manner that is suitable to decrease the thermal energy created by the ultrasonic blade 250 to spread from the bottom surface 268 thereof. In one embodiment, the protective sheath 252 may be formed by coating the bottom surface 268 of the ultrasonic blade 250 with a polymeric material. The protective sheath 252 may be formed of a variety of high temperature lubricious polymers. For example, the protective sheath 252 may be formed of any number of fluorinated polymers such as Tetrafluoroethylene or Polytetrafluoroethylene, such as Teflon® by DuPont. In another embodiment, the protective sheath 252 may be formed as separate rigid polymeric component permanently attached (e.g., affixed, mounted) to the bottom surface 268 of the ultrasonic blade 250. The protective sheath 252 may be attached to the bottom surface 268 of the ultrasonic blade 250 with physical snaps, adhesives, and/or insert/molding. In yet another embodiment, the protective sheath 252 may be formed as a separate rigid polymeric component mounted to a rigid portion of the ultrasonic instrument 270 and shield the bottom surface 268 of the ultrasonic blade 250 without physically contacting the bottom surface 268 of the ultrasonic blade 250. This provides the air gap 262 between the bottom surface 268 of the ultrasonic blade 250 and the separate rigid polymeric protective sheath 252. The air gap 262 enables irrigation fluid to travel between the protective sheath 252 and the bottom surface 268 of the ultrasonic blade 250 to assist in cooling the blade. In one embodiment, irrigation may be provided within the protective sheath to assist in cooling the ultrasonic blade 250 from ultrasonically induced thermal effects. For example, in one embodiment a protective sheath may be configured to act as an irrigation conduit along the bottom surface of the ultrasonic blade to provide directed irrigation for surgical regions as well as providing a cooling effect to the ultrasonic blade during use (FIGS. 52-55). In various other embodiments, the protective sheath 252 may be user deployable and/or retractable by the user. Thus the user may deploy the protective sheath 252 to shield the bottom surface 268 of the ultrasonic blade 150 from the bone 246 or may retract the protective sheath 252 when desired to enable back-cutting. In other embodiments, the protective sheath 252 may be configured to assist in the mechanical dissection or removal of the muscle tissue 244 from the bone 246. For example, the protective sheath 252 may be configured in the shape and style to accommodate a conventional curette or cobb blade with sharp cutting edges 258, 264. The sheath also may be employed as a fulcrum along the bottom surface 268 of the ultrasonic blade 250 while still enabling distal and lateral tissue effects by exposing the cutting edge 258 of the ultrasonic blade 250.

Figure 26:
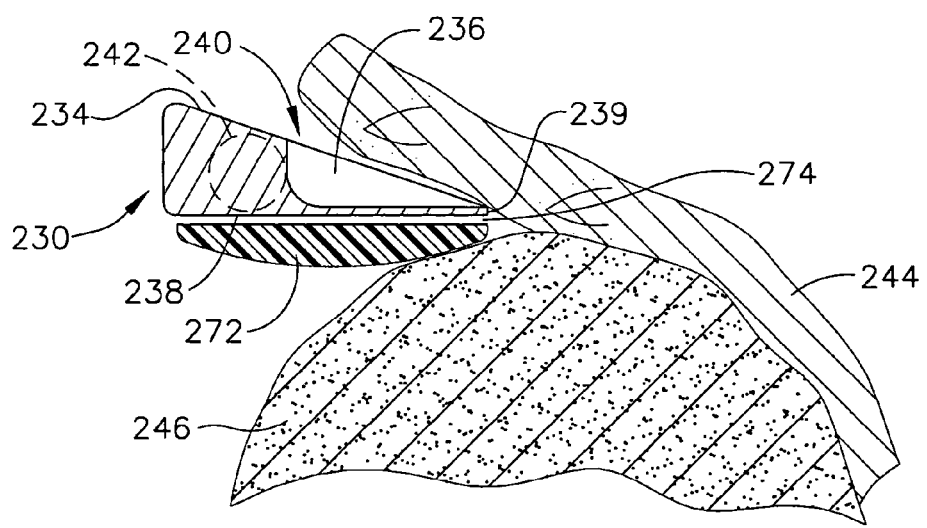
FIG. 26 illustrates a use one embodiment of the ultrasonic surgical blade shown in FIGS. 20, 21 comprising one embodiment of a protective sheath.

FIG. 26 illustrates a use of one embodiment of the ultrasonic surgical blade 230 shown in FIGS. 20, 21 comprising one embodiment of a protective sheath 272. The protective sheath 272 is positioned adjacent to the bottom surface 238 of the ultrasonic surgical blade 230. The protective sheath 272 protects the bone 246 as the cutting edge 239 dissects the muscle tissue 244 from the bone 246. An air gap 274 between the protective sheath 272 and the bottom surface 238 of the ultrasonic blade 230 provides a path for irrigation fluid to pass therebetween to dissipate thermal energy generated by the ultrasonic blade 230 while cutting. The protective sheath 272 may be formed of any polymeric material as previously discussed with respect to FIGS. 22-25.

Figure 27:
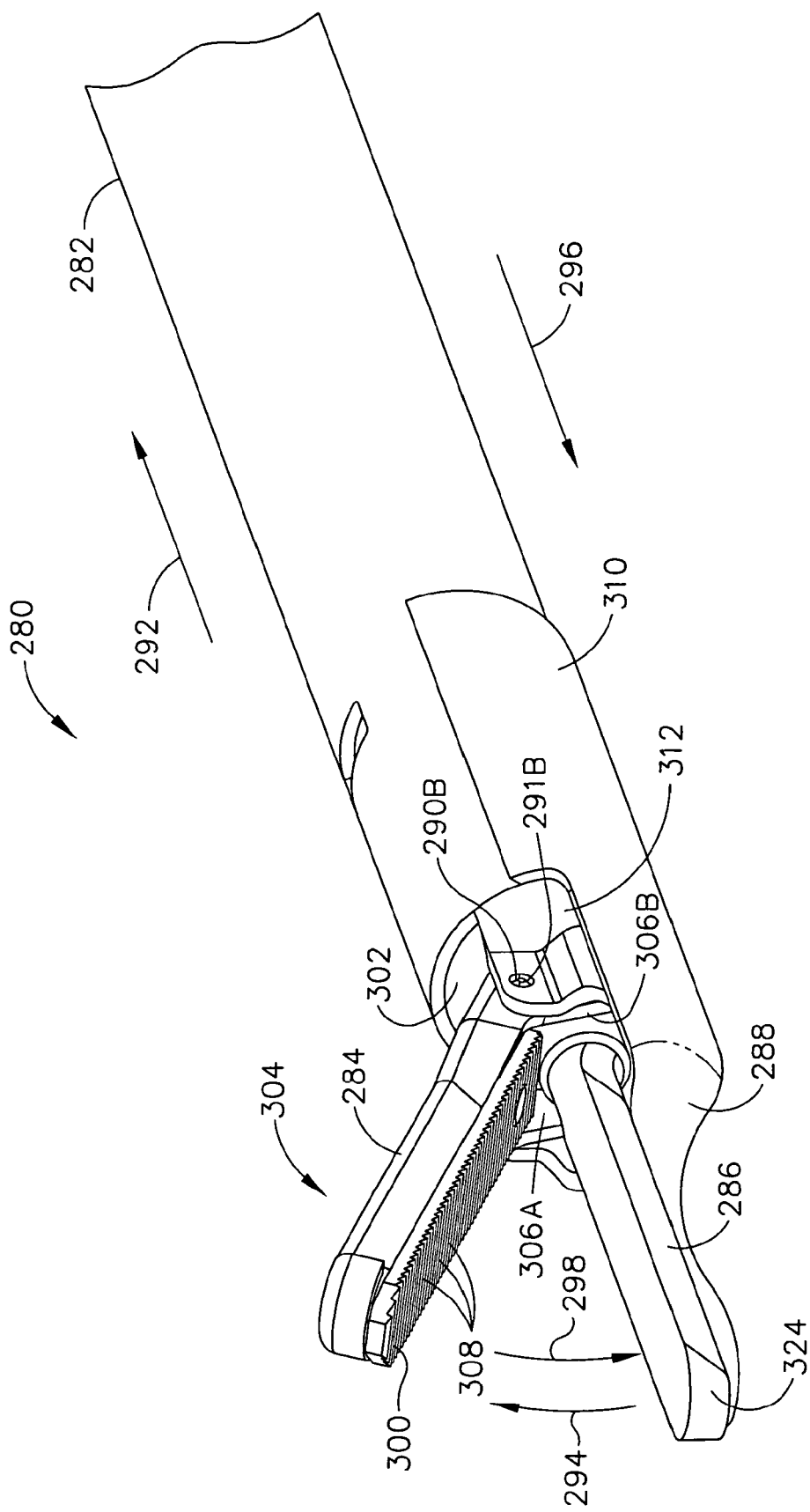
Figure 30:
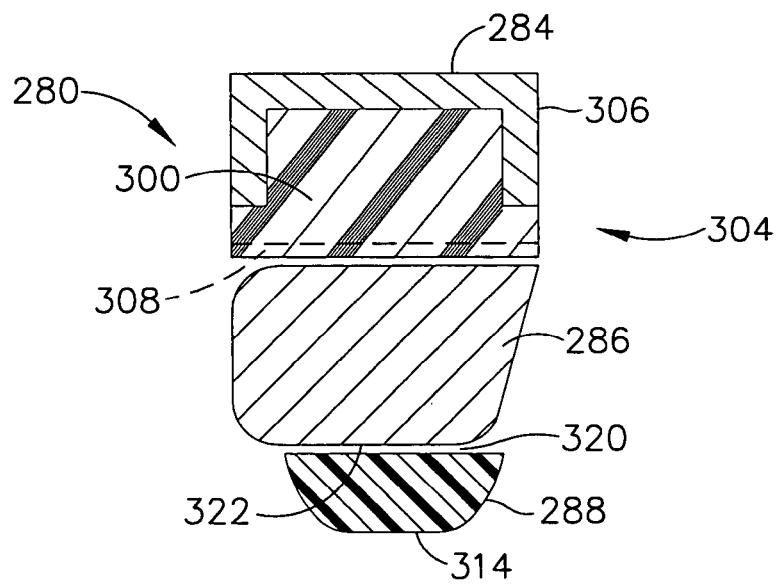
Figure 31:
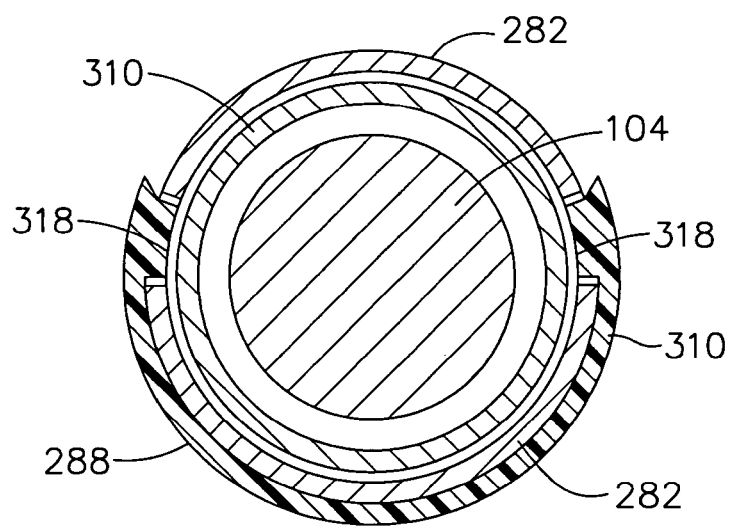

FIGS. 27-31 illustrate one embodiment of an ultrasonic surgical instrument 280 comprising an end effector 304. FIG. 27 is a top perspective view of one embodiment of the ultrasonic surgical instrument 280. FIG. 28 is a cross-sectional view of the ultrasonic surgical instrument 280 shown in FIG. 27 taken along the longitudinal axis of the ultrasonic surgical instrument 280. FIG. 29 is a bottom view of the ultrasonic surgical instrument 280 taken along lines 29-29. FIG. 30 is a cross-sectional view of the ultrasonic surgical instrument 280 taken along lines 30-30. FIG. 31 is cross-sectional view of the ultrasonic surgical instrument 280 taken along lines 31-31. With reference now to FIGS. 27-31, the ultrasonic surgical instrument 280 comprises an outer tubular member or outer tube 282 that extends from the handpiece assembly 456 (FIGS. 41-44). The outer tube 282 has a substantially circular cross-section and a longitudinal opening or aperture 302 to receive an inner tubular member or inner tube 312. The outer tube 282 has a substantially circular cross-section and may be fabricated from stainless steel. It will be recognized that the outer tube 282 may be constructed from any suitable material and may have any suitable cross-sectional shape. Located at the distal end of the ultrasonic surgical instrument 280 is an end effector 304 for performing various tasks, such as, for example, grasping tissue, cutting tissue and the like. It is contemplated that the end effector 304 may be formed in any suitable configuration.

The end effector 304 comprises a non-vibrating clamp arm assembly 284, an ultrasonic blade 286, and a protective sheath 288. The clamp arm assembly 284 comprises a tissue pad 300. The non-vibrating clamp arm assembly 284 is to grip tissue or compress tissue against the ultrasonic blade 286, for example.

The ultrasonic blade 286 is generally well-suited for cutting, coagulating, and reshaping tissue. In one embodiment the ultrasonic blade 286 may be configured as an ultrasonic surgical elevator blade generally well-suited to separate muscle tissue from bone. Nevertheless, the ultrasonic blade 286 may be employed in various other therapeutic procedures. The ultrasonic blade 286 comprises a cutting edge 324 at a distal portion and in other embodiments may comprise one or more lateral cutting edges and/or lateral atraumatic dull, smooth or curved edges. The ultrasonic blade 286 comprises a bottom surface 322 adjacent to the protective sheath 288 such that the protective sheath 288 shields the bottom surface 322 from contacting other surfaces. The ultrasonic blade 286 may be coupled to the ultrasonic transmission waveguide 104 or may be formed as a unitary piece therewith. The ultrasonic instrument 280 may be employed with the ultrasonic system 10.

The protective sheath 288 is generally well suited for glidingly engaging the surface of the bone to prevent damage to the bone while the ultrasonic blade 286 removes muscle tissue from bone and to dissipate thermal energy generated by the ultrasonic blade 286 while cutting. In the embodiment, the protective sheath 288 may be fixedly coupled to the ultrasonic blade 286 or to the outer tube 282 and is not user deployable. An air gap 320 between the bottom surface 322 of the ultrasonic blade 286 and the protective sheath 288 provides a path for irrigation fluid to pass therebetween to dissipate thermal energy generated by the ultrasonic blade 286. The protective sheath 288 comprises the proximal partially circumferentially extending portion 310 that overlaps and fixedly engages the outer tube 282. As previously discussed, the proximal partially circumferentially extending portion 310 comprises multiple projections 318 to engage apertures 316 formed in the outer tube 282. In one embodiment, the protective sheath 288 may be fixedly attached to the outer sheath 282 by way of the multiple projections 318 engaging the apertures 316 formed in the outer tube 282. As shown in FIG. 30, the protective sheath 288 comprises a curved substantially arcuate bottom surface 314 to slidingly engage bone. The curved bottom surface 314 comprises a convex portion 315 at a distal end and a concave portion 317 at a proximal end. The protective sheath 288 may be formed of any polymeric material as previously discussed with respect to FIGS. 22-25.

The end effector 304 is illustrated in a clamp open position. The clamp arm assembly 284 is preferably pivotally mounted to the distal end of the outer tube 282 at pivot points 290A, B such that the clamp arm assembly 284 can rotate in the direction shown by arrows 294, 298. The clamp arm assembly 284 preferably includes clamp arms 306A, B and corresponding pivot pins 291A, B on either side to engage the pivot points 290A, B. The distal end of the inner tube 312 comprises fingers or flanges 313A and 313B (not shown) that extend therefrom. The fingers 313A, B have corresponding openings 313A and 313B (not shown) to receive posts 315A and 315B (not shown) of the clamp arms 306A, B. When the inner tube 312 is moved axially, the fingers 313A, B move axially forwardly or rearwardly and engage the corresponding posts 315A, B of the clamp arms 306A, B to open and close the clamp arm assembly 284. For example, when the inner tube 312 moves axially rearwardly or is retracted towards the proximal end in the direction indicated by arrow 292, the clamp arm assembly 284 opens in the direction indicated by arrow 294. When the inner tube 312 moves axially or is advanced towards to the distal end in the direction indicated by arrow 296 the clamp arm assembly 284 closes in the direction indicated by arrow 298. The outer tube 282 remains fixed and the apertures 316 are configured to receive the projecting members 318 from the partially circumferentially extending portion 310 of the protective sheath 288. The proximal partially circumferentially extending portion 310 of the protective sheath 288 is thus fixedly mounted to the outer tube 282. In one embodiment, the proximal partially circumferentially extending portion 310 of the protective sheath 288 may be formed of similar materials as the protective sheath 288 or may be formed of other substantially rigid materials.

The clamp arm 306 includes the tissue pad 300 attached thereto for squeezing tissue between the ultrasonic blade 286 and the clamp arm assembly 300. The tissue pad 300 is preferably formed of a polymeric or other compliant material and engages the ultrasonic blade 286 when the clamp arm 306 is in its closed position. Preferably, the tissue pad 300 is formed of a material having a low coefficient of friction but which has substantial rigidity to provide tissue-grasping capability, such as, for example, TEFLON, a trademark name of E. I. Du Pont de Nemours and Company for the polymer polytetraflouroethylene (PTFE). The tissue pad 300 may be mounted to the clamp arm 300 by an adhesive, or preferably by a mechanical fastening arrangement. Serrations 308 are formed in the clamping surfaces of the tissue pad 300 and extend perpendicular to the axis of the ultrasonic blade 286 to allow tissue to be grasped, manipulated, coagulated and cut without slipping between the clamp arm 306 and the ultrasonic blade 286.

FIGS. 32-35 are cross-sectional views of various embodiments of ultrasonic surgical instruments 350, 352, 354, 356 taken along the longitudinal axis. The ultrasonic surgical instruments 350, 352, 354, 356 comprise respective fixedly attached protective sheaths 358, 364, 370, 376. As previously discussed, fixedly attached means that the protective sheaths are not deployable and remain in the position shown in FIGS. 32-35 during use of the instruments 350, 352. As shown in FIGS. 32-35, the ultrasonic surgical instrument 350, 352, 354, 356 each comprise the outer tube 282 that extends from a handpiece assembly (e.g., the handpiece assembly 60 shown in FIG. 1). The outer tube 282 has a substantially circular cross-section and a longitudinal opening or aperture 302 to receive the inner tube 312. Located at the distal end of the ultrasonic surgical instrument 350 is an end effector 304 for performing various tasks, such as, for example, grasping tissue, cutting tissue and the like. It is contemplated that the end effector 304 may be formed in any suitable configuration. The ultrasonic surgical instrument 350, 352, 354, 356 may be employed with the ultrasonic system 10.

The end effector 304 comprises the non-vibrating clamp arm assembly 284, an ultrasonic blade 286, and a protective sheath 354. The clamp arm assembly 284 is preferably pivotally attached to the distal end of the outer tube 282 at the pivot point 290. The clamp arm assembly 284 comprises a tissue pad 300. As previously discussed, the ultrasonic blade 286 may be coupled to the ultrasonic transmission waveguide 104 or may be formed as a unitary piece therewith and may be actuated by the ultrasonic system 10.

The protective sheaths 358, 364, 370, 376 are generally well suited for glidingly engaging the surface of the bone to prevent damage to the bone while the ultrasonic blade 286 removes muscle tissue from the bone and to dissipate thermal energy generated by the ultrasonic blade 286 while cutting. The protective sheaths 358, 364, 370, 376 may be fixedly coupled to the ultrasonic blade 286 or to the outer tube 282 and are not user deployable. An air gap 320 between the bottom surface 322 of the ultrasonic blade 286 and the fixed protective sheaths 358, 364, 370, 376 provides a space for irrigation fluid to pass therebetween to dissipate thermal energy generated by the ultrasonic blade 286 while cutting. In the embodiments illustrated in FIGS. 32-35, the fixedly mounted protective sheaths 358, 364, 370, 376 each comprise the proximal partially circumferentially extending portion 310 that overlaps and fixedly engages the outer tube 282. As previously discussed, the proximal partially circumferentially extending portion 310 comprises multiple projections 318 to engage the apertures 316 formed in the outer tube 282 and thus the protective sheaths 358, 364, 370, 376 are fixedly secured within the outer tube 282. The alternative embodiments, the fixed protective sheaths 358, 364, 370, 376 may be attached to an inner tube positioned within the outer tube 282.

The fixed protective sheaths 358, 364, 370, 376 each comprise a distal portion comprising respective tapered bodies 384, 388, 392, 398 that extend longitudinally beyond the distal portion of the ultrasonic blade 286 to protect the distal cutting edge 324 of the ultrasonic blade 286. In other embodiments, the tapered bodies 384, 388, 392, 398 may extend laterally to protect longitudinal portions of the ultrasonic blade 286. The fixed protective sheaths 358, 364, 370, 376 each comprise respective substantially planar sheet portions 359, 365, 371, 377 extending longitudinally between the distal tapered bodies 384, 388, 392, 398 and the proximal partially circumferentially extending portion 310 to shield the bottom surface 322 of the ultrasonic blade 286. The protective sheaths 358, 364, 370, 376 may be formed of any polymeric material as previously discussed with respect to FIGS. 22-25.

As shown in FIG. 32, the fixed protective sheath 358 comprises the tapered body 360 at a distal end that extends longitudinally beyond the distal end of the ultrasonic blade 286. The tapered body 360 comprises a substantially planar top surface 362 and a substantially planar bottom surface 382 that taper from a proximate end to a blunt distal end 384.

As shown in FIG. 33, the fixed protective sheath 364 comprises the tapered body 366 at a distal end that extends longitudinally beyond the distal end of the ultrasonic blade 286. The tapered body 366 comprises a substantially planar top surface 368 and a substantially planar bottom surface 386 that taper from a proximate end to a blunt distal end 388. The substantially planar top and bottom surfaces 368, 386 have corresponding radiused contoured surfaces that meet the blunt surface 388.

As shown in FIG. 34, the fixed protective sheath 370 comprises the tapered body 378 at a distal end that extends longitudinally beyond the distal end of the ultrasonic blade 286. The tapered body 378 comprises a curved top surface 374 and a curved bottom surface 390 that taper from a proximate end to a sharp distal end 392.

As shown in FIG. 35, the fixed protective sheath 376 comprises the tapered body 378 at a distal end that extends longitudinally beyond the distal end of the ultrasonic blade 286. The tapered body 378 comprises a substantially planar top surface 396 and a substantially curved bottom surface 394 that taper from a proximate end to a sharp distal end 398.

FIGS. 36-37 are cross-sectional views of one embodiment of an ultrasonic surgical instrument 400 taken along the longitudinal axis. The ultrasonic surgical instrument 400 may be employed with the ultrasonic system 10. The ultrasonic surgical instrument 400 comprises a deployable protective sheath 402. In one embodiment, the deployable protective sheath 402 may be deployed by a user during a surgical procedure. Deployable means that the deployable protective sheath 402 may be advanced to a distal end in the direction indicated by arrow 404 to be put into use and may be retracted to a proximate end in the direction indicated by arrow 406 when it is to be taken out of use. The deployable protective sheath 402 comprises a distal portion 401 that substantially shields the bottom surface 322 of the ultrasonic blade 286 when it is deployed. The deployable protective sheath 402 comprises a proximate portion 403 that extends to the handpiece assembly (e.g., the handpiece assembly 60 shown in FIG. 1) where it is coupled to a protective sheath deploying and retracting mechanism. The distal portion 401 may be formed slightly thicker then the proximal portion 403. The deployable protective sheath 402 may be formed of any polymeric material as previously discussed with respect to FIGS. 22-25. In one embodiment, the proximal portion 403 may be formed of the same material as the distal portion 401 of the deployable protective sheath 402. In other embodiments, the proximal portion 403 may be formed of a different more durable material than the distal portion 401 of the deployable protective sheath 402 to withstand repeated deployments and retractions. For example, the proximal portion 403 may be formed of metal or other durable material to withstand the moderate forces required to hold the deployable protective sheath 402 in place during deployment, retraction, and use.

The ultrasonic surgical instrument 400 comprises the outer tube 282 that extends from the handpiece assembly 456. The outer tube 282 has a substantially circular cross-section and a longitudinal opening or aperture 302 to receive the inner tube 312. Located at the distal end of the ultrasonic surgical instrument 350 is an end effector 304 for performing various tasks, such as, for example, grasping tissue, cutting tissue and the like. It is contemplated that the end effector 304 may be formed in any suitable configuration. The end effector 304 comprises the non-vibrating clamp arm assembly 284, an ultrasonic blade 286, and the deployable protective sheath 402. The clamp arm assembly 284 is preferably pivotally attached to the distal end of the outer tube 282 at the pivot point 290. The clamp arm assembly 284 comprises a tissue pad 300. As previously discussed, the ultrasonic blade 286 may be coupled to the ultrasonic transmission waveguide 104 or may be formed as a unitary piece therewith.

When the deployable protective sheath 402 is advanced in the direction indicated by arrow 404, it is generally well suited for glidingly engaging the surface of the bone to prevent damage to the bone while the ultrasonic blade 286 removes muscle tissue from the bone and to dissipate thermal energy generated by the ultrasonic blade 286 while cutting. The deployable protective sheath 402 also is well suited to shield the bottom surface of the blade 322 from contact with other objects. The deployable protective sheath 402 may be retracted in the direction indicated by arrow 406 when it is not needed. When the deployable protective sheath 402 is deployed, the air gap 320 between the bottom surface 322 of the ultrasonic blade 286 and the protective sheath 402 provides a space for irrigation fluid to pass therebetween to dissipate thermal energy generated by the ultrasonic blade 286 while cutting. In one embodiment, the deployable protective sheath 402 may retract within the inner tube 312.

FIGS. 38-39 are cross-sectional views of one embodiment of an ultrasonic surgical instrument 410 taken along the longitudinal axis. The ultrasonic surgical instrument 410 comprises a deployable protective sheath 412. In one embodiment, the deployable protective sheath 412 may be deployed by a user during a surgical procedure. Deployable means that the deployable protective sheath 412 may be advanced to a distal end in the direction indicated by arrow 404 to be put in use and may be retracted to a proximate end in the direction indicated by arrow 406 to be put out of use. The deployable protective sheath 402 comprises a distal portion 407 that substantially covers the bottom surface 418 of the ultrasonic blade 414 when it is deployed. The deployable protective sheath 412 comprises a proximate portion 405 that extends to a handpiece assembly (e.g., the handpiece assembly 60 shown in FIG. 1) where it is coupled to a protective sheath deploying and retracting mechanism. The distal portion 407 may be formed slightly thicker then the proximal portion 405. The distal portion comprises a vertically extending projection 420 to protect the cutting edge 416 of the ultrasonic blade 414. The projection 420 is adapted to engage and compress the bottom surface of the ultrasonic blade 414 when it is retracted. The deployable protective sheath 402 may be formed of any polymeric material as previously discussed with respect to FIGS. 22-25. In one embodiment, the proximal portion 405 may be formed of the same material as the distal portion 407 of the deployable protective sheath 412. In other embodiments, the proximal portion 405 may be formed of a different more durable material than the distal portion 407 of the deployable protective sheath 412 to withstand repeated deployments and retractions. For example, the proximal portion 405 of the deployable protective sheath 412 may be formed of metal or other durable material to withstand the moderate forces required to hold the deployable protective sheath 412 in place during deployment, retraction, and use.

The ultrasonic surgical instrument 410 comprises the outer tube 282 that extends from the handpiece assembly 456. The outer tube 282 has a substantially circular cross-section and a longitudinal opening or aperture 302 to receive the inner tube 312. Located at the distal end of the ultrasonic surgical instrument 350 is an end effector 304 for performing various tasks, such as, for example, grasping tissue, cutting tissue and the like. It is contemplated that the end effector 304 may be formed in any suitable configuration. The end effector 304 comprises the non-vibrating clamp arm assembly 284, an ultrasonic blade 414 with a distal chisel-shaped cutting edge 416, and the deployable protective sheath 412. The clamp arm assembly 284 is preferably pivotally attached to the distal end of the outer tube 282 at the pivot point 290. The clamp arm assembly 284 comprises a tissue pad 300. As previously discussed, the ultrasonic blade 286 may be coupled to the ultrasonic transmission waveguide 104 or may be formed as a unitary piece therewith.

When the deployable protective sheath 412 is advanced in the direction indicated by arrow 404, it is generally well suited for gliding along the surface of the bone to prevent damage to the bone while the ultrasonic blade 414 removes muscle tissue from the bone. The deployable protective sheath 412 may be retracted in the direction indicated by arrow 406 when it is not needed. When the deployable protective sheath 412 is deployed, the air gap 320 between the bottom surface 418 of the ultrasonic blade 414 and the protective deployable sheath 412 provides a space for irrigation fluid to pass therebetween. The protective deployable sheath 412 retracts inside the inner tube 312.

Figure 40:
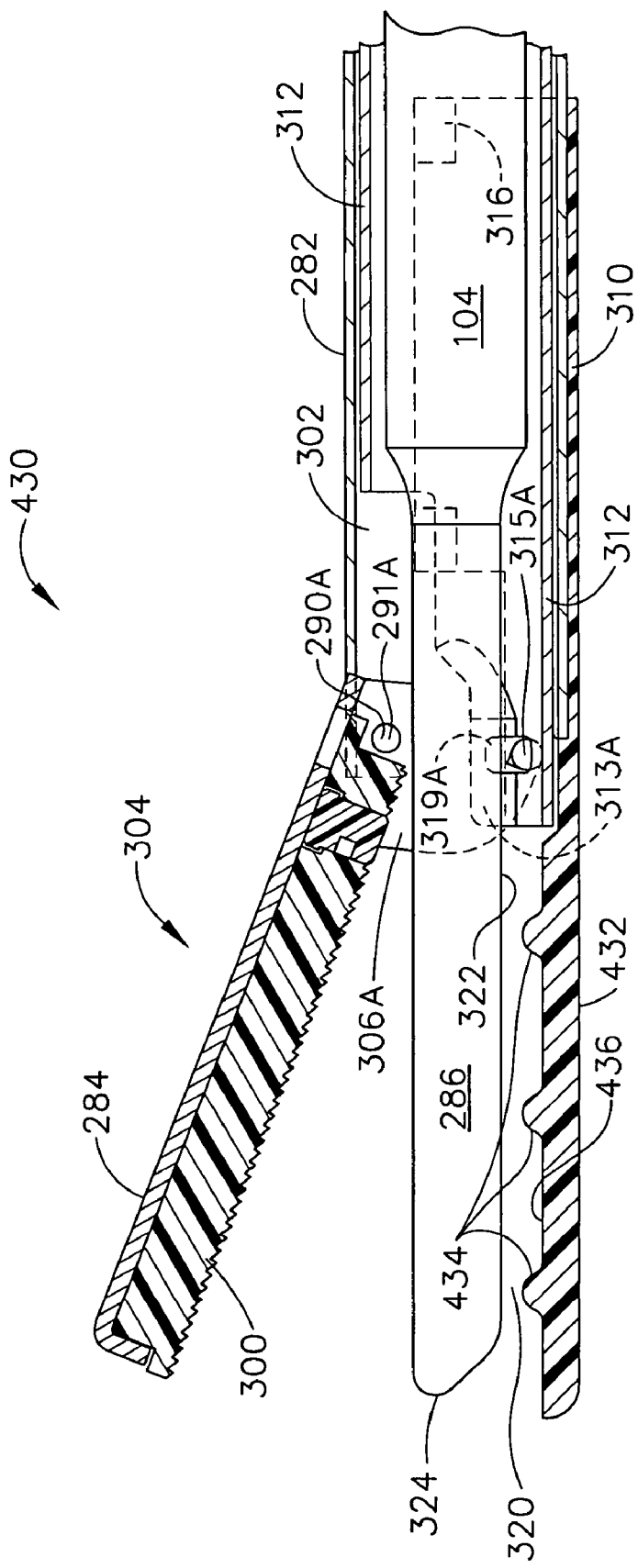
FIG. 40 is cross-sectional view of one embodiment of an ultrasonic surgical instrument taken along the longitudinal axis.

FIG. 40 is cross-sectional view of one embodiment of an ultrasonic surgical instrument 430 taken along the longitudinal axis. The ultrasonic surgical instrument 430 may be employed with the ultrasonic system 10. The ultrasonic surgical instrument 430 comprises a fixedly attached protective sheath 432. As previously discussed, fixedly attached means that the protective sheath is not deployable and remains in the position shown in FIG. 40 for the usable life of the instrument 430. As shown in FIG. 40, the ultrasonic surgical instrument 430 comprises the outer tube 282 that extends from the handpiece assembly 456. The outer tube 282 has a substantially circular cross-section and a longitudinal opening or aperture 302 to receive the inner tube 312. Located at the distal end of the ultrasonic surgical instrument 350 is an end effector 304 for performing various tasks, such as, for example, grasping tissue, cutting tissue and the like. It is contemplated that the end effector 304 may be formed in any suitable configuration.

The end effector 304 comprises the non-vibrating clamp arm assembly 284, an ultrasonic blade 286, and a protective sheath 432. The clamp arm assembly 284 is preferably pivotally attached to the distal end of the outer tube 282 at the pivot points 290A, B. The clamp arm assembly 284 comprises a tissue pad 300. As previously discussed, the ultrasonic blade 286 may be coupled to the ultrasonic transmission waveguide 104 or may be formed as a unitary piece therewith.

The protective sheath 432 is generally well suited for glidingly engaging the surface of the bone to prevent damage to the bone while the ultrasonic blade 286 removes muscle tissue from the bone and to dissipate thermal energy generated by the ultrasonic blade 286 while cutting. The protective sheath 432 is also well suited to shield the bottom surface 322 of the blade 286. The protective sheath 432 may be fixedly coupled to the ultrasonic blade 286 or to the outer tube 282 by way of projections 318 (FIGS. 27-31) and apertures 316 and is not user deployable. An air gap 320 between the bottom surface 322 of the ultrasonic blade 286 and the fixed protective sheath 432 provides a space for irrigation fluid to pass therebetween to dissipate thermal energy generated by the ultrasonic blade 286 while cutting. The fixed protective sheath 432 comprises the proximal partially circumferentially extending portion 310 that overlaps and fixedly engages the outer tube 282. As previously discussed, the proximal partially circumferentially extending portion 310 comprises the multiple projections 318 to engage the apertures 316 formed in the outer tube 282. The fixed protective sheath 432 is attached to the outer tube 282. The fixed protective sheath 432 comprises discrete projections or bumps 434 formed on a top surface 436 thereof. There may be one or multiple bumps 434 formed on the top surface 436 of the protective sheath 432. The bumps 434 decrease the contact surface area between the ultrasonic blade 286 and the protective sheath 432, which may occur during a procedure when the protective sheath is used as a fulcrum. This may reduce the heat or thermal energy generated by the ultrasonic blade 286 and the load on the ultrasonic blade 286. The protective sheath 432 may be formed of any polymeric material as previously discussed with respect to FIGS. 22-25.

Figure 41:
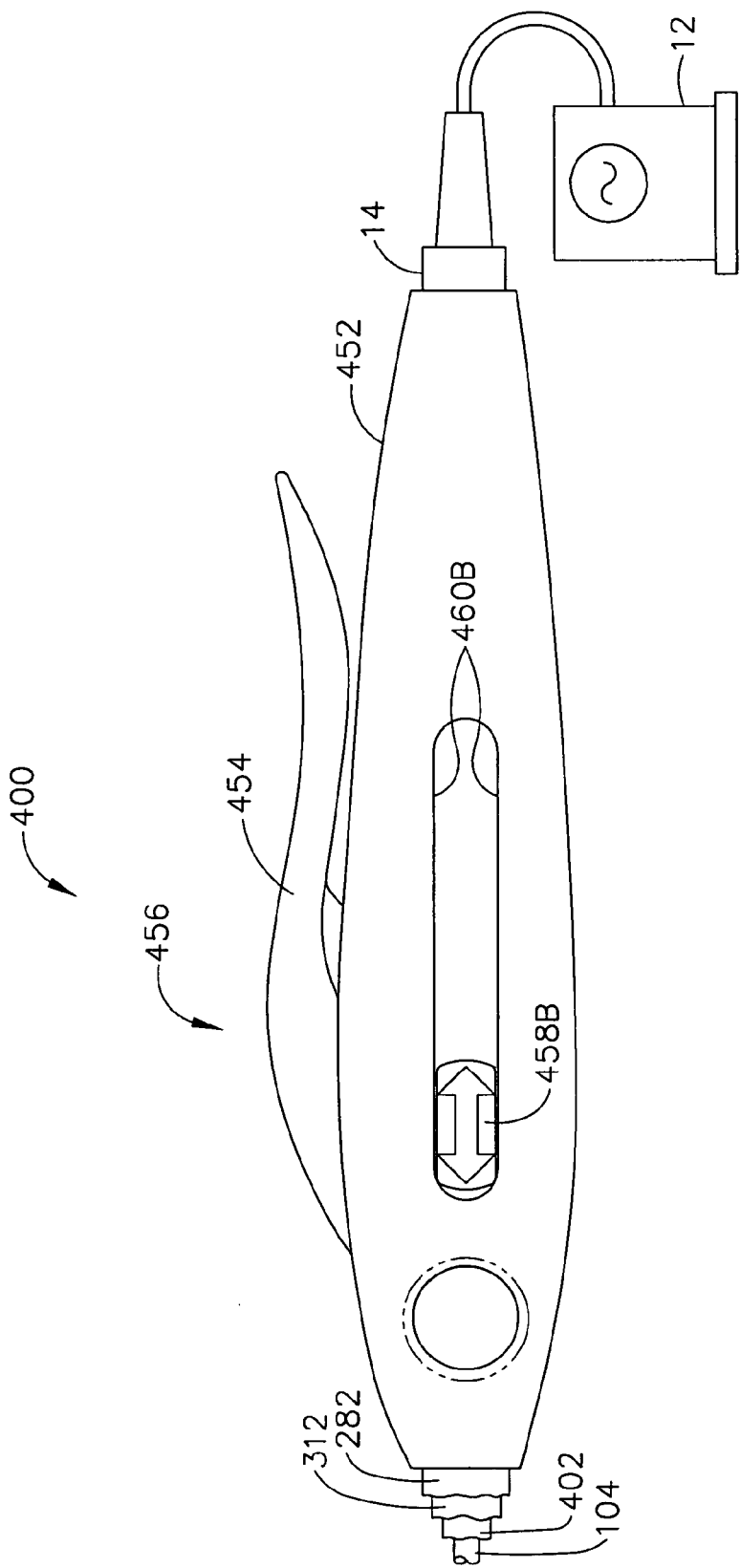
FIGS. 41-43 illustrate one embodiment of an ultrasonic system, where.
Figure 42:
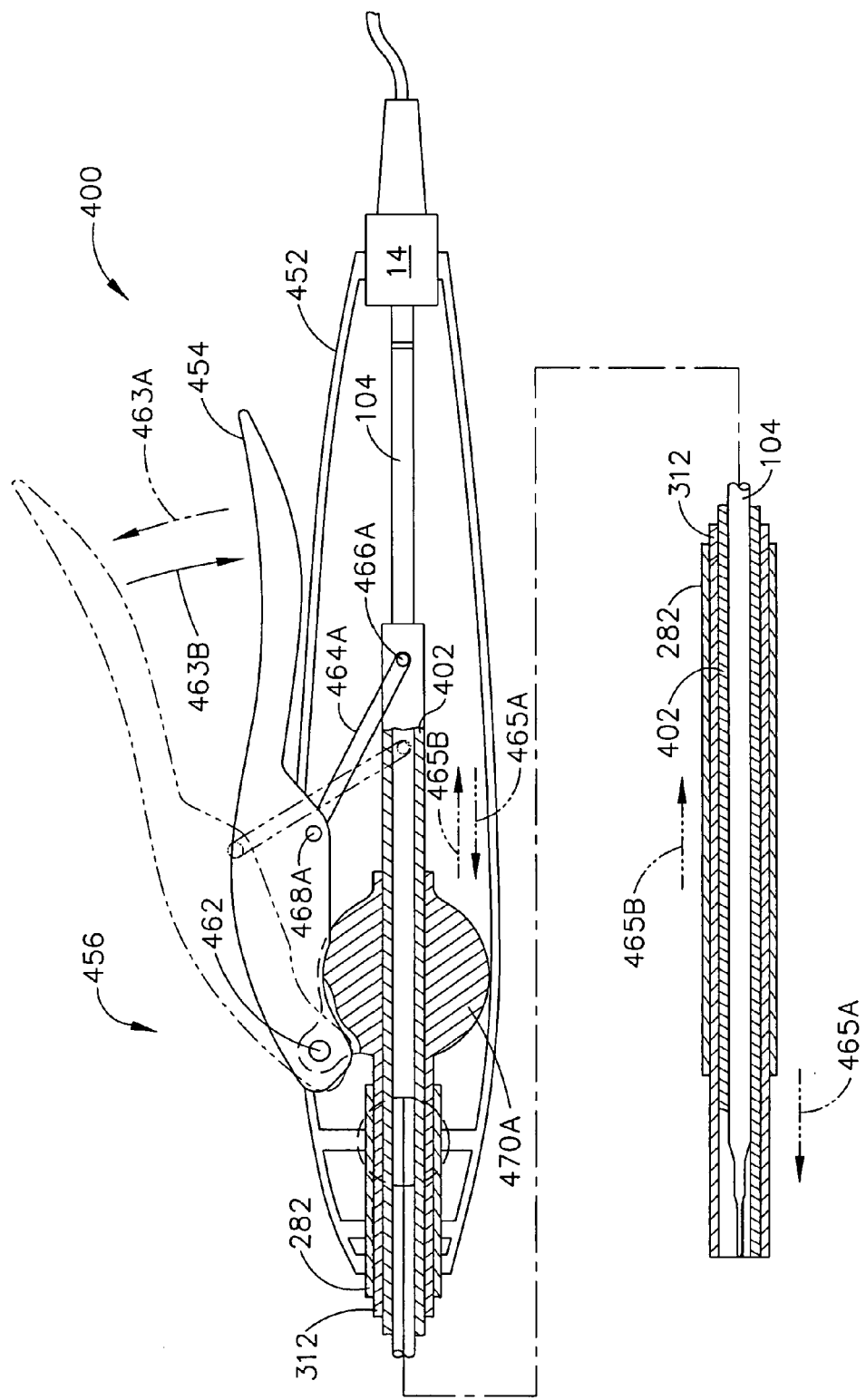
Figure 43:
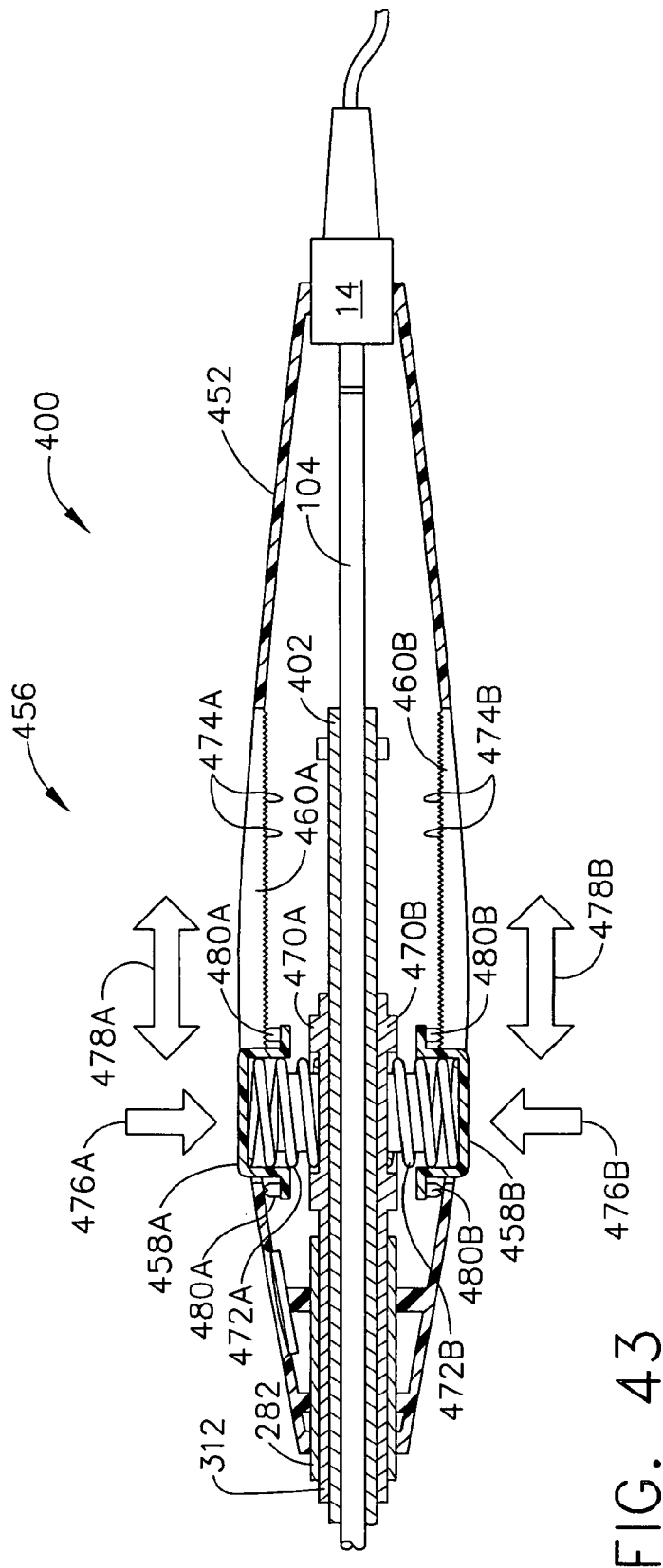

FIGS. 41-43 illustrate one embodiment of an ultrasonic system 400. FIG. 41 is a side view of the ultrasonic system 400. One embodiment of the ultrasonic system 400 comprises the ultrasonic signal generator 12 coupled to the ultrasonic transducer 14, a hand piece housing 452, and an end effector 304 (shown in FIG. 27) forming an ultrasonic instrument 456. The ultrasonic instrument 456 comprises a curved lever member 454 coupled to the protective sheath 402 to move the protective sheath 402 axially. The ultrasonic instrument 456 also comprises a slideable member 458B coupled to the inner tube 312. The slideable member 458B moves axially within a slot that defines walls 460B formed in the hand piece housing 452 to actuate the end effector 304.

FIG. 42 is a cross-sectional side view of the ultrasonic system 456 shown in FIG. 41 and a cross-sectional view of various tube assemblies to couple the hand piece housing 452 with an end effector. As shown in FIG. 42, the curved lever member 454 is pivotally mounted to the hand piece housing 452 at pivot point 462 such that it can rotate in the direction indicated by arrows 463A, B. Link members 464A and 464B (not shown) are pivotally coupled at a proximate end to pivot points 466A and 466B (not shown) and at a distal end to pivot points 468A and 468B (not shown). When the curved lever member 454 is rotated about the pivot point 462 in the direction indicated by arrow 463A the sheath 402 moves axially in the direction indicated by arrow 465A in its deployed position. When the curved lever member 454 is moved in the direction indicated by arrow 463B the sheath 402 moves axially in the direction indicated by arrow 465B n its retracted position.

FIG. 43 is a bottom cross-sectional view of the ultrasonic instrument 456 shown in FIG. 41. As shown in FIG. 43, the slideable members 458A, B are held in a locked position by respective springs 472A, B which engage and compress the slideable members 458A, B against an interior portion of the hand piece housing 452. The interior portion of the hand piece housing 452 comprises rows of serrated edges 474A, B formed along inner portions of the walls 460A, B defined by the slot. Notched members 480A, B are mounted to flanges formed on the slideable members 458A, B and are configured to engage the respective serrated edges 474A, B formed in the respective walls 460A, B. Bodies 470A, B are formed integrally with the inner tube 312 or are attached to thereto. When a force is applied in the direction indicated by arrows 476, B against the respective springs 472A, B, the slideable members 458A, B can be moved axially as indicated by arrows 478A, B. Thus the inner tube 312 moves axially to actuate the clamp arm assembly 284 of the end effector 304.

In alternative embodiments, the ultrasonic instrument 456 may be adapted and configured such that the curved lever member 454 is coupled to the inner tube 312 and the slideable members 458A, B are coupled to the protective sheath 402. Accordingly, rotating the curved lever member 454 moves the inner tube 312 axially to actuate the end effector 304. And the slideable members 458A, B can be used to axially deploy and retract the protective sheath 402.

FIGS. 44-51 illustrate one embodiment of an ultrasonic system 500. FIG. 44 is a side view of the ultrasonic instrument 506 with the deployable protective sheath 402 in a stowed or retracted position. FIG. 45 is a top view of the ultrasonic instrument 506 with the deployable protective sheath 402 in the stowed or retracted position taken along line 45-45 in FIG. 44. FIG. 46 is a side view of the ultrasonic instrument 506 with the deployable protective sheath 402 in a deployed position. FIG. 47 is a top view of the ultrasonic instrument 506 in the deployed position taken along line 47-47 in FIG. 46.

With reference to FIGS. 44-47, one embodiment of the ultrasonic instrument 500 is coupled to an ultrasonic signal generator 12 and comprises an ultrasonic transducer 14, a hand piece housing 502, and an end effector 504 forming an ultrasonic instrument 506. The ultrasonic instrument 506 comprises a slideable member 508 coupled to the deployable protective sheath 402 in any suitable manner as previously discussed. The slideable member 508 moves axially within a slot 510 formed in the hand piece housing 502 to actuate or deploy/retract the deployable protective sheath 402. The slideable member 508 is shown in the deployable protective sheath 402 retracted or stowed position. When the slideable member 508 moves axially in the direction indicated by arrow 514 the deployable protective sheath 402 also moves axially in the same direction to its retracted or stowed position. When the slideable member 508 moves axially in the direction indicated by arrow 516 the deployable protective sheath 402 also moves axially in the same direction to its deployed position. Once deployed, the deployable protective sheath 402 may be locked in place with any suitable locking mechanism. An air gap 518 provides a path for irrigation fluid to cool the ultrasonic blade 512 while cutting. The end effector 504 comprises an ultrasonic blade 512 coupled to the ultrasonic transducer 14 by the ultrasonic transmission waveguide 104 as previously discussed. The fixed outer tube 282 (or sheath) shields the surgeon and the patient from unintended contact with the ultrasonic blade 512 and the ultrasonic transmission waveguide 104.

FIG. 48 is a more detailed side view of the ultrasonic instrument 506 with the deployable protective sheath 402 in a stowed or retracted position. FIG. 49 is a more detailed top view of the ultrasonic instrument 506 with the protective sheath 402 in the stowed or retracted position taken along line 49-49 in FIG. 48. FIG. 50 is a more detailed side view of the ultrasonic instrument 506 with the deployable protective sheath 402 in a deployed position. FIG. 51 is a more detailed top view of the ultrasonic instrument 506 in the deployed position taken along line 51-51 in FIG. 50.

With reference to FIGS. 44-51, the deployable protective sheath 402 is user deployable by moving the slideable member 508 in the direction indicated by arrow 516. The distal end of the deployable protective sheath 402 may be formed of any polymeric material as previously discussed with respect to FIGS. 22-25. The proximal end of the deployable protective sheath 402 may be formed of metal or other durable material to withstand the moderate forces required to hold the deployable protective sheath 402 in place during deployment, retraction, and use.

FIG. 50 shows the deployable protective sheath 402 in the deployed position in a substantially relaxed state as indicated by the air gap 518 between the deployable protective sheath 402 and the ultrasonic blade 512. Thus, in a stress free state, the deployable protective sheath 402 does not contact the ultrasonic blade 512. When the deployable protective sheath 402 is used as a fulcrum, however, it may contact the ultrasonic blade 512 for some period of time. However, when the pressure is released on the ultrasonic instrument 500, the deployable protective sheath 402 is sufficiently resilient to return to its initial position, thus restoring the air gap 518 between the protective sheath 412 and the ultrasonic blade 512. If needed, a separate spring may be added to the deployable protective sheath 402 to ensure that it no longer contacts the ultrasonic blade 512 once the pressure is released. In the illustrated embodiment, the deployable protective sheath 402 is shown to be smaller than the outline of the ultrasonic blade 512. This enables the user to cut tissue with the distal tip and both edges of the ultrasonic blade 512 when the deployable protective sheath 402 is deployed. In alternate embodiments, the deployable protective sheath 402 may also cover some or all of the three edges of the ultrasonic blade 512.

Figure 52:
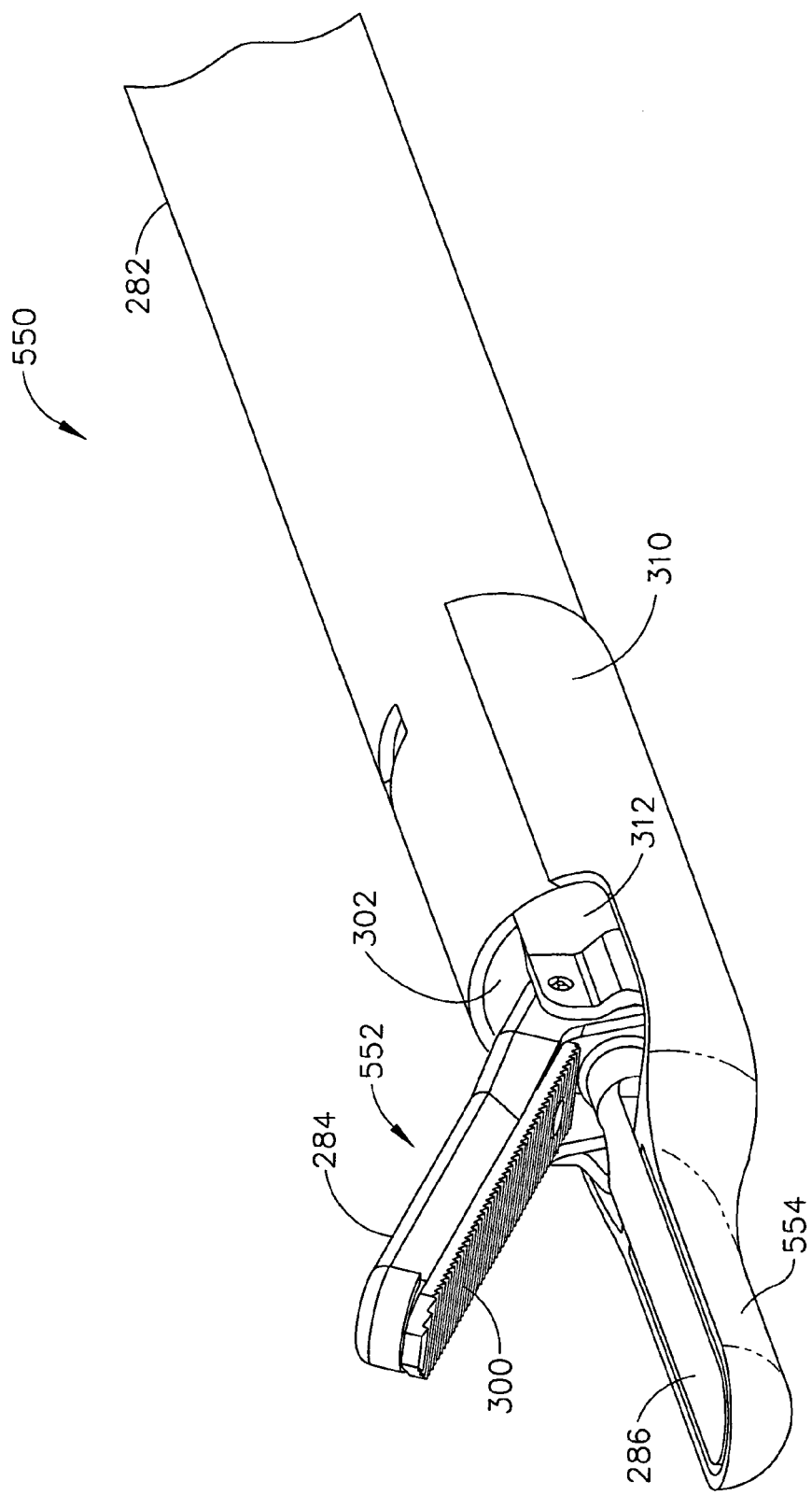
Figure 53:
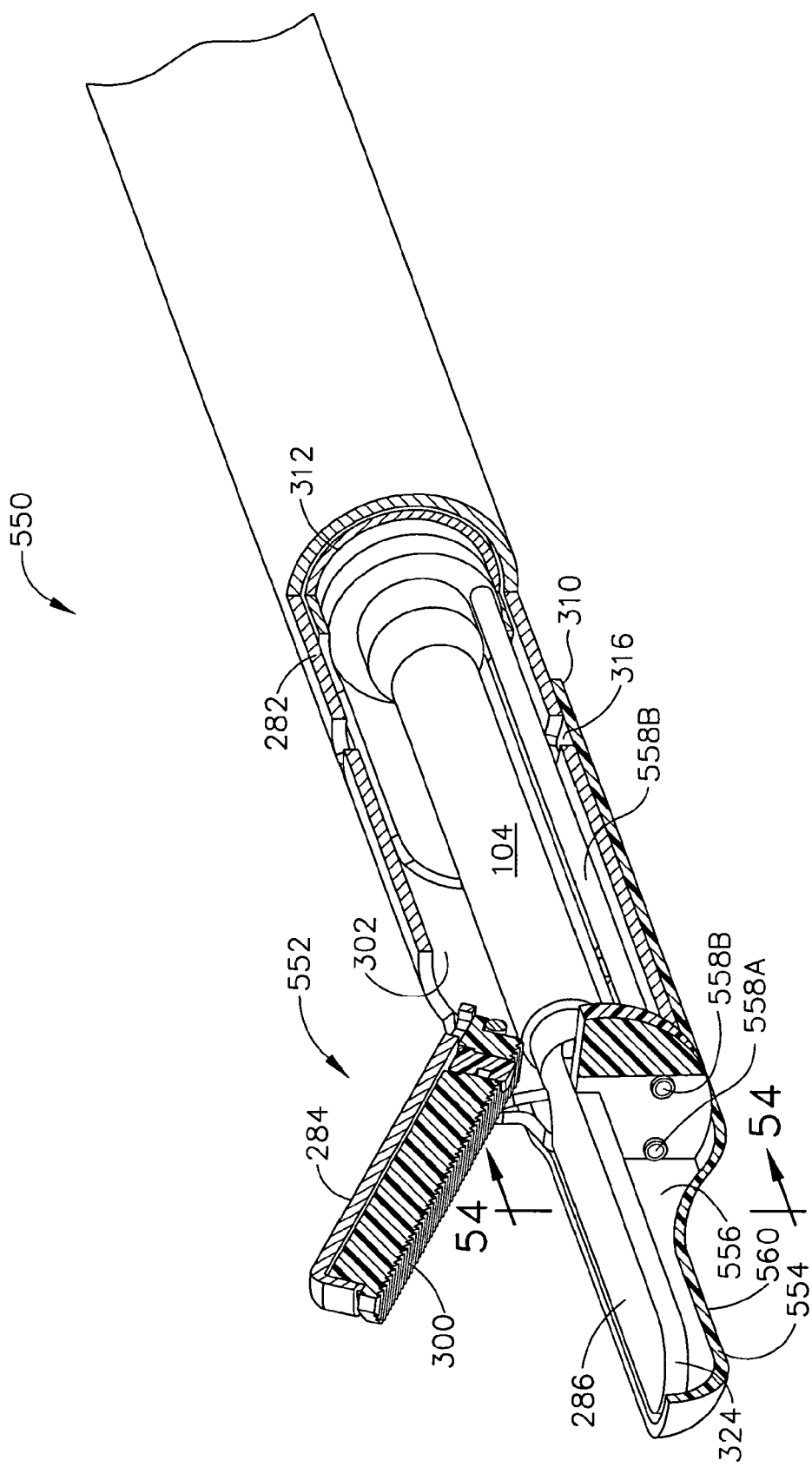
Figure 56:
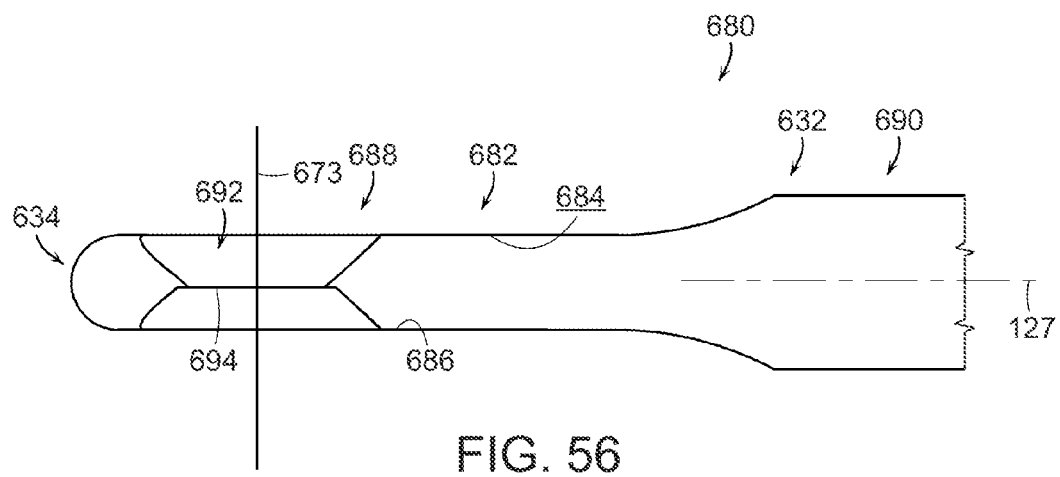
FIGS. 56-59 illustrate one embodiment of an ultrasonic blade, where.

FIGS. 52-55 illustrate one embodiment of an ultrasonic surgical instrument 550 comprising an end effector 552. The ultrasonic surgical instrument may be employed with the ultrasonic system 10. FIG. 52 is a top perspective view of one embodiment of the ultrasonic surgical instrument 550. FIG. 53 is a partial cross-sectional view of the ultrasonic surgical instrument 550 shown in FIG. 52 taken along the longitudinal axis of the ultrasonic surgical instrument 550. FIG. 54 is a cross-sectional view of the ultrasonic surgical instrument 550 taken along lines 54-54 shown in FIG. 53. FIG. 55 is a top view of the ultrasonic surgical instrument 550.

With reference now to FIGS. 52-55, the ultrasonic surgical instrument 550 comprises an outer member or outer tube 282 that extends from the handpiece assembly 60 or 456 (FIG. 1 or FIGS. 41-44). The outer tube 282 has a substantially circular cross-section and a longitudinal opening or aperture 302 to receive an inner member or an inner tube 312. The outer tube 282 has a substantially circular cross-section and may be fabricated from stainless steel. It will be recognized that the outer tube 282 may be constructed from any suitable material and may have any suitable cross-sectional shape. Located at the distal end of the ultrasonic surgical instrument 550 is an end effector 552 for performing various tasks, such as, for example, grasping tissue, cutting tissue and the like. It is contemplated that the end effector 304 may be formed in any suitable configuration.

The end effector 552 comprises a non-vibrating clamp arm assembly 284, an ultrasonic blade 286, and a protective sheath 554. The end effector 552 is illustrated in a clamp open position and operates in a manner discussed above. The clamp arm assembly 284 comprises a tissue pad 300. The non-vibrating clamp arm assembly 284 is to grip tissue or compress tissue against the ultrasonic blade 286, for example. The protective sheath 552 defines a chamber 556 in fluid communication with irrigation channels or tubes 558A, B to receive irrigation fluid from the irrigation channels 558A, B. The irrigation channels 558A, B couple to conventional irrigation devices by way of ports 560A, B (not shown) at the proximate end of the ultrasonic instrument 550. The irrigation channels 558A, B deliver irrigation fluid to the chamber 556 to dissipate thermal energy generated by the ultrasonic blade 286 while cutting and carrying away pieces cut bone and tissue. Irrigation may be controlled manually by way of a control button on the handpiece or automatically wherein each time the ultrasonic instrument 550 is powered on a irrigation fluid release cam may be activated to release the irrigation fluid.

The ultrasonic blade 286 is generally well-suited for cutting, coagulating, and reshaping tissue. In one embodiment the ultrasonic blade 286 may be configured as an ultrasonic surgical elevator blade generally well-suited to separate muscle tissue from bone. Nevertheless, the ultrasonic blade 286 may be employed in various other therapeutic procedures. The ultrasonic blade 286 comprises a cutting edge 324 at a distal portion and may comprise cutting edges extending longitudinally along the sides of the ultrasonic blade 286. The ultrasonic blade 286 comprises a bottom surface 322 adjacent to the protective sheath 554. The ultrasonic blade 286 may be coupled to the ultrasonic transmission waveguide 104 or may be formed as a unitary piece therewith.

The protective sheath 554 is generally well suited for glidingly engaging the surface of the bone to prevent damage to the bone while the ultrasonic blade 286 removes muscle tissue from the bone and to dissipate thermal energy generated by the ultrasonic blade 286 while cutting. The protective sheath 554 may be fixedly coupled to the ultrasonic instrument 550 or may be user deployable. In the illustrated embodiment, the protective sheath 550 is fixedly mounted to the outer tube 282 as previously discussed. The protective sheath 288 comprises the proximal partially circumferentially extending portion 310 that overlaps and fixedly engages the outer tube 282. As previously discussed, the proximal partially circumferentially extending portion 310 comprises multiple projections to engage the apertures 316 formed in the outer tube 282. When fixedly attached, the protective sheath 554 may be attached to the outer tube 282. When the protective sheath 554 is deployed, it may be attached to an inner tube received within the inner tube 312 that is slidingly engaged to a deployment mechanism on the handpiece portion of the ultrasonic instrument 550 as previously discussed. The protective sheath 554 comprises a bottom surface 560 to slidingly engage bone. The protective sheath 554 may be formed of any polymeric material as previously discussed with respect to FIGS. 22-25.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical blade for a surgical instrument, the surgical instrument having a transducer configured to produce vibrations along a longitudinal axis at a predetermined frequency, the surgical blade comprising:
a body portion comprising a first side, a second side, and a width defined between said first and second sides, wherein said body portion further comprises a center of gravity and a centerline extending through said center of gravity;
a step portion extending from said body portion, wherein said step portion comprises a first surface, a second surface, and a cutting edge situated intermediate said first and second surfaces, wherein said second surface faces away from said centerline, wherein said first surface extends at an angle through said centerline between a first plane including said cutting edge and a second plane which is parallel to said first plane, wherein said first surface is not parallel to said second surface, wherein said first and second surfaces are oriented such that there is an angle defined therebetween, wherein said blade is configured such that the relationship of:

$$\frac{x^2}{2}*\tan^{-1}\alpha + \frac{(w-x)}{2}(x*\tan^{-1}\alpha - s) - \left(\frac{w}{2}\right)^2 \tan^{-1}\alpha$$

is substantially equal to zero;
wherein w is said width of said body portion;
wherein s is the distance between said first plane and said second plane;
wherein α is said angle defined between said first and second surfaces of said step portion; and
wherein x is the distance between said second side of said body portion and said cutting edge.

2. The surgical blade of claim 1, wherein said step portion includes a center of gravity positioned along said centerline, and wherein said cutting edge is not positioned along said centerline.

3. The surgical blade of claim 2, wherein said second surface is substantially parallel to said centerline.

4. The surgical blade of claim 1, wherein said step portion includes a center of gravity positioned along said centerline, and wherein said step portion is asymmetric with respect to said centerline.

5. The surgical blade of claim 1, wherein said relationship is equal to zero.

6. A surgical blade for a surgical instrument, the surgical instrument having a transducer configured to produce vibrations along a longitudinal axis at a predetermined frequency, the surgical blade comprising:
a body portion comprising a first side, a second side, and a width (w) defined between said first and second sides, wherein said body portion further comprises a center of gravity and a centerline extending through said center of gravity;
a step portion extending from said body portion, wherein said step portion comprises a first surface, a second surface, and a cutting edge situated intermediate said first and second surfaces, wherein said second surface faces away from said centerline, wherein said first surface extends at an angle through said centerline between a first plane including said cutting edge and a second plane which is parallel to said first plane, wherein said first plane and said second plane are separated by a distance s, wherein said first surface is not parallel to said second surface, wherein said first and second surfaces are oriented such that there is an angle (α) defined therebetween, and wherein a second distance (x) is defined between said second side of said body portion and said cutting edge.

7. The surgical blade of claim 6, wherein said blade is configured such that, for any given values of s and w, the relationship of:

$$A*x^2*\tan^{-1}\alpha + B*x*\tan^{-1}\alpha + C*\tan^{-1}\alpha + D*x + E$$

is substantially equal to zero, and wherein A, B, C, D, and E are constants.

8. The surgical blade of claim 6, wherein said blade is configured such that, for any given values of s and α, the relationship of:

$$A*x^2 + B*x + C*x*w + D*w + E*w^2 + F$$

is substantially equal to zero, and wherein A, B, C, D, E, and F are constants.

9. The surgical blade of claim 6, wherein said blade is configured such that, for any given values of w and α, the relationship of:

$$A*x^2 + B*x + C*x*s + D*s + E$$

is substantially equal to zero, and wherein A, B, C, D, and E are constants.

10. A surgical blade for a surgical instrument, the surgical instrument having a transducer configured to produce vibrations along a longitudinal axis at a predetermined frequency, the surgical blade comprising:
a distal end;
a proximal end; and a cross-section situated intermediate said distal end and said proximal end, wherein said cross-section is defined by a plane which is perpendicular to the longitudinal axis, wherein said cross-section is further defined by a centerline which lies in the plane, and wherein said cross-section comprises:

a center portion; and a cutting portion extending from said center portion, wherein said cutting portion comprises a center of gravity which is positioned along said centerline, wherein said cutting portion further comprises a cutting edge which is not positioned along said centerline, wherein said cutting edge is positioned intermediate a first face and a first face of said cutting portion, and wherein said second face is oriented away from said centerline and said second face extends through said centerline.

11. The surgical blade of claim 10, wherein said first face is not parallel to said second face, wherein said first and second faces are oriented such that there is an angle defined therebetween.

12. The surgical blade of claim 11, wherein said center portion includes a first side, a second side, and a width defined between said first and second sides, wherein said second face of said cutting portion extends between a first plane including said cutting edge and a second plane which is parallel to said first plane, wherein said blade is configured such that the relationship of:

$$\frac{x^2}{2} * \tan^{-1}\alpha + \frac{(w-x)}{2}(x * \tan^{-1}\alpha - s) - \left(\frac{w}{2}\right)^2 \tan^{-1}\alpha$$

is substantially equal to zero;

wherein w is said width of said center portion;

wherein s is the distance between said first plane and said second plane;

wherein $\alpha$ is said angle defined between said first and second faces of said cutting portion; and wherein x is the distance between said second side of said center portion and said cutting edge.

13. The surgical blade of claim 12, wherein said relationship is equal to zero.

14. A surgical blade for a surgical instrument, the surgical instrument having a transducer configured to produce vibrations along a longitudinal axis at a predetermined frequency, the surgical blade comprising:

a distal end;

a proximal end; and a cross-section situated intermediate said distal end and said proximal end, wherein said cross-section is defined by a plane which is perpendicular to the longitudinal axis, wherein the plane is at least partially defined by a transverse axis which is perpendicular to the longitudinal axis, and wherein the cross-section comprises:

a body portion having a first mass ($M_{B1}$) positioned on a first side of said transverse axis and a second mass ($M_{B2}$) positioned on a second side of said transverse axis; and a step portion having a first mass ($M_{S1}$) positioned on said first side and a second mass ($M_{S2}$) positioned on said second side, wherein $M_{B1}+M_{S1}$ is substantially equal to $M_{B2}+M_{S2}$, wherein said step portion further includes a cutting edge, wherein said cutting edge is not positioned along said transverse axis, wherein said cutting edge is positioned intermediate a first surface and a second surface of said step portion, and wherein said second surface is oriented away from said transverse axis and said first surface extends through said transverse axis.

15. The surgical blade of claim 14, wherein $M_{B1}+M_{S1}$ is equal to $M_{B2}+M_{S2}$.

* * * * *